US009610258B2

(12) United States Patent
McWherter et al.

(10) Patent No.: US 9,610,258 B2
(45) Date of Patent: Apr. 4, 2017

(54) METHODS OF STABILIZING THE EXTRACELLULAR MATRIX AND COMPOSITIONS THEREFOR

(71) Applicant: MD MATRIX HEALTH LLC, Colleyville, TX (US)

(72) Inventors: Joseph F. McWherter, Keller, TX (US); Uzzi Reiss, Los Angeles, CA (US)

(73) Assignee: MD MATRIX HEALTH LLC, Colleyville, TX (US)

( * ) Notice: Subject to any disclaimer, the term of this patent is extended or adjusted under 35 U.S.C. 154(b) by 0 days.

(21) Appl. No.: 15/147,715

(22) Filed: May 5, 2016

(65) Prior Publication Data

US 2016/0243057 A1     Aug. 25, 2016

Related U.S. Application Data

(63) Continuation of application No. 14/054,578, filed on Oct. 15, 2013, now abandoned, which is a continuation-in-part of application No. PCT/US2012/033659, filed on Apr. 13, 2012.

(60) Provisional application No. 61/476,148, filed on Apr. 15, 2011.

(51) Int. Cl.

| | |
|---|---|
| *A61K 36/82* | (2006.01) |
| *A61K 31/121* | (2006.01) |
| *A61K 31/05* | (2006.01) |
| *A61K 31/09* | (2006.01) |
| *A61K 31/26* | (2006.01) |
| *A61K 31/353* | (2006.01) |
| *A61K 36/752* | (2006.01) |
| *A61K 36/9066* | (2006.01) |
| *A61K 36/31* | (2006.01) |
| *A61K 36/53* | (2006.01) |
| *A61K 36/61* | (2006.01) |
| *A61K 9/00* | (2006.01) |
| *A61K 31/12* | (2006.01) |
| *A61K 31/122* | (2006.01) |
| *A61K 31/355* | (2006.01) |
| *A61K 31/4045* | (2006.01) |
| *A61K 31/593* | (2006.01) |
| *A61K 36/324* | (2006.01) |
| *A61K 31/385* | (2006.01) |
| *A61K 31/404* | (2006.01) |
| *A61K 36/00* | (2006.01) |
| *A61K 36/185* | (2006.01) |
| *A61K 9/06* | (2006.01) |

(52) U.S. Cl.
CPC ......... *A61K 31/121* (2013.01); *A61K 9/0014* (2013.01); *A61K 9/0041* (2013.01); *A61K 31/05* (2013.01); *A61K 31/09* (2013.01); *A61K 31/12* (2013.01); *A61K 31/122* (2013.01); *A61K 31/26* (2013.01); *A61K 31/353* (2013.01); *A61K 31/355* (2013.01); *A61K 31/385* (2013.01); *A61K 31/404* (2013.01); *A61K 31/4045* (2013.01); *A61K 31/593* (2013.01); *A61K 36/00* (2013.01); *A61K 36/185* (2013.01); *A61K 36/31* (2013.01); *A61K 36/324* (2013.01); *A61K 36/53* (2013.01); *A61K 36/61* (2013.01); *A61K 36/752* (2013.01); *A61K 36/82* (2013.01); *A61K 36/9066* (2013.01); *A61K 9/06* (2013.01)

(58) Field of Classification Search
CPC ...... A61K 36/82; A61K 33/06; A61K 31/202; A61K 31/05; A61K 31/355; A61K 31/195; A61K 31/28; A61K 31/122; A61K 36/9066; A61K 36/324; A61K 31/201; A61K 31/59; A61K 36/31; A61K 36/752

See application file for complete search history.

(56) References Cited

U.S. PATENT DOCUMENTS

| | | |
|---|---|---|
| 6,827,945 B2 | 12/2004 | Rosenbloom |
| 7,351,739 B2 | 4/2008 | Ho et al. |
| 2006/0052438 A1 | 3/2006 | Ho et al. |
| 2007/0003536 A1 | 1/2007 | Zimmerman et al. |
| 2012/0014883 A1 | 1/2012 | Scott et al. |

OTHER PUBLICATIONS

International Search Report and Written Opinion of the International Searching Authority dated Jul. 13, 2012, issued in International Application No. PCT/US2012/033659, 11 pages.

*Primary Examiner* — Nannette Holloman
(74) *Attorney, Agent, or Firm* — Haynes and Boone, LLP

(57) ABSTRACT

Disclosed are prophylactic and therapeutic methods, as well as dosing regimens and medicaments for use in preventing chronic disease, for treating acute or long-term inflammatory-mediated conditions in affected or at-risk subjects, and for stabilizing one or more components of the mammalian extracellular matrix. Also disclosed are pharmaceutical compositions and topical formulations thereof that include multiple, phytochemically-active, nutraceutical compounds, and that possess potent anti-inflammatory and extracellular matrix-stabilizing properties both in vitro and in vivo.

24 Claims, 11 Drawing Sheets

| PATIENT # | OVERALL THERMO RANGE | | | AVE TEMP OF SAMPLE OVAL | | | AVE TEMP DELTA/90 DAYS | | STANDARD DFV | |
|---|---|---|---|---|---|---|---|---|---|---|
| | INITIAL | SECOND | # DAYS | INITIAL | SECOND | DELTA (C) | (DEGREES C) | % | SD INITIAL | SD SECOND |
| 1 | 10.98 | 9.34 | 98 | 31.22 | 29.74 | -1.48 | -1.359 | -4.4% | 0.92 | 0.68 |
| 2 | 6.08 | 7.35 | 91 | 29.22 | 29.01 | -0.21 | -0.208 | -0.7% | 0.96 | 0.88 |
| 3 | 7.93 | 7.91 | 125 | 29.11 | 28.47 | -0.64 | -0.461 | -1.6% | 0.85 | 0.64 |
| 4 | 7.33 | 9.87 | 91 | 29.42 | 28.92 | -0.50 | -0.495 | -1.7% | 0.69 | 0.59 |
| 5 | 7.34 | 6.39 | 70 | 30.33 | 32.62 | 2.29 | 2.944 | 9.7% | 0.78 | 0.72 |
| 6 | 7.30 | 7.34 | 90 | 27.34 | 26.96 | -0.38 | -0.380 | -1.4% | 0.96 | 0.87 |
| 7 | 7.33 | 7.35 | 99 | 27.82 | 28.29 | 0.47 | 0.427 | 1.5% | 0.67 | 0.70 |
| 8 | 7.33 | 9.35 | 112 | 31.17 | 31.76 | 0.59 | 0.474 | 1.5% | 0.71 | 0.56 |
| 9 | 11.42 | 8.99 | 98 | 29.24 | 29.72 | 0.48 | 0.441 | 1.5% | 1.05 | 0.83 |
| 10 | 7.39 | 7.26 | 91 | 29.99 | 28.99 | -1.00 | -0.989 | -3.3% | 0.81 | 0.71 |
| 11 | 8.72 | 8.01 | 91 | 27.83 | 29.51 | 1.68 | 1.662 | 6.0% | 0.63 | 0.49 |
| 12 | 7.34 | 7.34 | 76 | 30.34 | 29.85 | -0.49 | -0.580 | -1.9% | 0.78 | 0.75 |
| 13 | 7.33 | 7.34 | 77 | 31.94 | 29.73 | -2.21 | -2.583 | -8.1% | 0.91 | 0.81 |
| 14 | 7.34 | 5.88 | 111 | 28.12 | 27.94 | -0.18 | -0.146 | -0.5% | 0.74 | 0.62 |
| 15 | 7.34 | | 126 | 29.16 | 30.16 | 1.00 | 0.714 | 2.4% | 0.78 | 0.53 |
| | 7.90 | 7.84 | | 29.48 | 29.44 | -0.21 | -0.25 | -0.75% | 0.82 | 0.69 |

| SUMMARY | AVE TEMP | +/-1 SD |
|---|---|---|
| AFTER 90 DAYS | 29.22 | 1.38 |
| INITIAL | 29.42 | 1.64 |
| CHANGE | -0.75% | -15.1% |

NOTE B

FIG. 1

| INGREDIENT | FAMILY | %(W/W) | MCW |
|---|---|---|---|
| PHASE A | | | |
| WATER | | 60.00 | |
| PHASE B | | | |
| ISOPROPYL PALMITATE | | 3.00 | |
| ISOPROPYL MYRISTATE | | 3.00 | |
| LIPOWAX D (CETEARYL ALCOLHOL AND CETEARETH-20) | | 5.00 | |
| TETRAHYDROCURCUMIN (60/39/10 TETRAHYDROCURCUMIN, TETRAHYDROCURCUMINS AND TETRAHYDROPIPERINE) | CURCUMIN | 0.50 | 20g* |
| ALPHA LIPOIC ACID DL ALPHA (DL = THIOCTIC ACID) | | 0.15 | 5g |
| KELTROL CG (XANTHAN GUM) | | 0.10 | |
| PHASE C | | | |
| LIPODERM - CORE | | 6.50 | 535g** |
| I SABI (WASABI JAPONICA) POWDER | | 2.00 | 20g |
| BROCCOLI SEED OIL WITH SGS AND MUSTARD SEED OIL | ISOTHIOCYANATE | 6.00 | 40ml*** |
| MELATONIN | | 0.10 | |
| PHARMASOLVE NPM**** (N-METHYL PYRROLIDONE) | | 2.50 | |
| VITAMIN D3 LIQUID | | 1.50 | 26ml |
| VITAMIN E TOCOPHEROL | | 1.00 | 5ml***** |
| DIM POWDER (3'3'-DIINDOLYLMETHANE (DIM)) | | 0.20 | 2g |
| RESVERATROL (3,5,4'-TRIHYDROXY-TRANS-STILBENE) | STILLBENE | 2.00 | 20g |
| PHASE D | | | |
| FRANKINCENSE SCARA ESSENTIAL OIL | ESSENTIAL OIL | 0.10 | |
| ROSEMARY WATER SOLUBLE OIL | ESSENTIAL OIL | 0.50 | 33.3ml |
| SWEET ORANGE ESSENTIAL OIL | ESSENTIAL OIL | 0.60 | 15 drops |
| FRANKINCENSE WATER SOLUBLE ESSENTIAL OIL | ESSENTIAL OIL | 3.33 | 33.3ml |
| THYME WATER SOLUBLE | ESSENTIAL OIL | 3.33 | 33.3ml |
| CLOVE ESSENTIAL OIL | ESSENTIAL OIL | 0.30 | |
| OPTIPHEN PLUS (PHENOXYETHANOL, CAPRYLYL GLYCOL AND SORBIC ACID) | | 1.25 | |
| EGG-GINE (AS GREEN TEA) | CATECHIN | 0.10 | 20g |

FIG. 6A

| PHASE E | | |
|---|---|---|
| SEPIGEL 305 (POLYACRYLAMIDE BASED EMULSION AND RHEOLOGY MODIFIER) | 1.00 | |
| TOTAL | 104.06 | |
| RCB NOTES | | |
| PROPYLENE GLYCOL LIQUID | | 25ml |
| DIMETHYLSULFOXIDE (DMSO LIQUID) | | 100ml |
| MENADIONE USP (K-3) POWDER (VITAMIN K-3) | | 0.3g |
| POLOXAMER 407 NF GRANULES (PLURONIC F-127 NF) (BLOCK COPOLYMER OF ETHYLENE OXIDE AND PROPYLENE OXIDE) | | 150g |
| CARCINOSIN 30C SOLUTION | | 33.3ml |
| POKE ROOT OIL (PHYTOLACCA AMERICANA/OLIVE/VIT E OIL) | | 16.65ml |
| *AS CURCUMINOID CG POWDER | | |
| **PCCA LIPODERM | | |
| ***BROCCOLI SEED OIL WITH CONCENTRATED SULFORAPHANE 104mg | | |
| ****SHOULD THIS BE "NMP"? | | |
| *****AS VITAMIN E ACETATE LIQUID | | |

FIG. 6B

| ACETONE | +OA (RIGHT EAR WITH OXAZALONE) | -OA (LEFT EAR WITHOUT OXAZALONE) | (+OA)-(-OA) IN mg | PROPHALACTIC BETAMETHASONE | +OA (RIGHT EAR WITH OXAZALONE) | -OA (LEFT EAR WITHOUT OXAZALONE) | (+OA)-(-OA) IN mg |
|---|---|---|---|---|---|---|---|
| 1 | 89.91 | 16.67 | 73.24 | 3 | 43.52 | 28.76 | 14.76 |
| 2 | 92.47 | 21.75 | 70.72 | 4 | 48.69 | 23.71 | 24.98 |

| THERAPEUTIC MDMH, 0.5, 6, 12 HR POST OA | +OA (RIGHT EAR WITH OXAZALONE) | -OA (LEFT EAR WITHOUT OXAZALONE) | (+OA)-(-OA) IN mg | PROPHALACTIC MDMH FOR 12 HR PRIOR TO SENSITIZATION; THERAPEUTIC MDMH, 0.5, 6, 12 HR POST OA | +OA (RIGHT EAR WITH OXAZALONE) | -OA (LEFT EAR WITHOUT OXAZALONE) | (+OA)-(-OA) IN mg |
|---|---|---|---|---|---|---|---|
| 5 | 49.13 | 29.48 | 19.65 | 7 | 46.75 | 28.67 | 18.08 |
| 6 | 57.45 | 36.53 | 30.92 | | | | |

| | ACETONE | PROPHALACTIC BETAMETHASONE | THERAPEUTIC MDMH, 0.5, 6, 12 HR POST OA | PROPHALACTIC MDMH FOR 12 HR PRIOR TO SEN'SN; THERAPEUTIC MDMH; 0.5, 6, 12 HR POST OA |
|---|---|---|---|---|
| MEAN | 72.0 | 19.9 | 25.3 | 18.1 |
| SD | 1.8 | 7.2 | 8.0 | #DIV/0! |
| % INHIBITION OF ACETONE | | 72.4 | 64.9 | 74.9 |
| % INHIBITION TO TOPICAL BETAM. | | 100% | 90% | 103% |

FIG. 8B

METHODS OF STABILIZING THE EXTRACELLULAR MATRIX AND COMPOSITIONS THEREFOR

CROSS-REFERENCE TO RELATED APPLICATIONS

The present application is a Continuation of U.S. patent application Ser. No. 14/054,578, filed Oct. 15, 2013; which is a Continuation-in-Part of PCT International Patent Appl. No. PCT/US2012/033,659, filed Apr. 13, 2012; which claims the benefit of priority to U.S. Provisional Patent Appl. No. 61/476,148, filed Apr. 15, 2011; the contents of each of which is specifically incorporated herein in its entirety by express reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

BACKGROUND OF THE INVENTION

Field of the Invention

The present disclosure relates to orthomolecular compositions comprising multiple phytochemical active ingredients, and pharmaceutical formulations thereof. In particular aspects, the disclosure is directed to compounding a plurality of active ingredients to produce a multi-component formulation that has both potent anti-inflammatory capabilities and the ability to inhibit aberrant tissue renin-angiotensin factors (tRAS). In related embodiments, the present disclosure provides prophylactic and therapeutic methods for use in affected or at-risk mammalian (and particularly, human) subjects, a) to stabilize the extracellular matrix (ECM); b) to prevent, treat, or ameliorate one or more symptoms of acute or chronic disease; and c) to prevent, alter, or modulate acute and/or chronic aberrant biological activities, including, for example, those attributable to tRAS peptides, enzymes, and receptors, or overexpression of the oxidoreductases, COX-2 and LOX.

Description of Related Art

Breast Carcinoma

Disease of the breast is currently rising in the American population at an alarming rate. Fibrocystic changes, fibroadenomas, and breast cancer have even been termed by some as reaching "epidemic" proportion. Statistics show that breast cancer is the second leading cause of death in women ages 20-59. In the United States, a new breast cancer is diagnosed every 3 minutes, with approximately 63,000 new cases of carcinoma in situ (CIS) being reported annually. The incidence of ductal CIS (DCIS) rose from 1.87 per 100,000 in 1973-1975 to approximately 32.5 per 100,000 in 2004. Alarmingly, over 40,000 women die from breast cancer on a yearly basis. Unfortunately, for those with advanced forms of the disease, chemotherapy has not significantly affected long-term survival rates.

Prevention of breast cancer, or any cancer for that matter, has been an elusive goal especially when employing the current medical paradigm. Since the Nixon administration declared "war on cancer" in the 1970s, a great deal of research and money has been devoted to achieving this end. Unfortunately, the battle remains un-won, despite valiant efforts across both research and treatment fronts. In spite of the many billion dollars allocated for this "war," relatively little progress has been made, particularly in its prevention or in increasing the long-term survivability of those with advanced metastatic disease. Although many (and oftentimes, expensive) chemotherapeutic agents are at the physician's disposal, the ultimate solution for winning the battle with cancer still eludes even the brightest contemporary minds. Currently there is only a 2.3% increase in survival rate using chemotherapy.

The failure to win the war, however, is not from lack of resource allocation, but a faulty plan-of-attack based solely on the prevailing paradigm of intervention at the cellular level. Medicine's current view of early carcinogenesis focuses on the relationship of the cell as the driving force behind the neoplastic process. This has been termed as the "somatic mutation theory" or SMT, which argues that an accumulation of mutations and other heritable changes in the susceptible cell can result in cancer. The SMT paradigm, however, is not without its critics. Problems with its basic tenets have been noted in a number of scientific publications by Kolata, Sonnenschein, Soto, and other well-known artisans in the field.

The inventors have noticed various observations, however, that question the validity of the SMT paradigm. These observations include, for example: 1) mice fitted with subcutaneous filters that have small holes give rise to tumor formation while mice fitted with the same filter material but having only larger holes remained tumor-free; 2) transplantation of normal rat mammary cells into adjacent stroma (which was cleared of local epithelia cells but previously exposed to a chemical carcinogen) results in a much higher tumor rate as compared to controls; and 3) transplantation of normal cells into untreated, but "inappropriate," stromal environment induced carcinoma formation. Yet, these now-abnormal cells returned to a normal state upon transplantation back into their original "appropriate" stromal environment.

The Extracellular Matrix (ECM)

In cell biology, the term "extracellular matrix" (ECM) refers to the extracellular part of animal tissue that provides structural support to the cells, and performs various other important functions. ECM is the defining feature of connective tissue in animals, and includes the interstitial matrix (present in the intracellular spaces around various animal cells) and the basement membrane (sheet-like depositions of ECM on which various epithelial cells rest). It provides support and anchorage for cells, sequesters cellular growth factors, regulates intercellular communication, and segregates or compartmentalizes various types of cells that are contained within the matrix.

The interstitial space is composed of a number of biological molecules, including, glycosaminoglycans (GAG) and fibrous proteins that form an interlocking mesh that act as a compression buffer against the stress placed on the ECM. Glycosaminoglycans consist of repeating disaccharide units. Hyaluronan (HA) lacks any sulfate groups, but the rest of the GAGs contain sulfates at various positions.

Formation of ECM is essential for processes like cell growth, tissue differentiation, wound healing and fibrosis. An understanding of the complex structure and function of the ECM also helps facilitate analysis of the dynamics of tumor invasion and cancer metastasis, which often involve destruction of ECM by matrix metalloproteinases and serine and threonine proteases.

Components of the ECM are produced intracellularly by resident cells, and secreted into the ECM via exocytosis. Once secreted, they then aggregate with the existing matrix. As described by Varki et al. (1999), the ECM determines the physical characteristics of tissues and many of the biological properties of cells embedded in it. Major components of the ECM are fibrous proteins that provide tensile strength (e.g., various collagens and elastin), adhesive glycoproteins (e.g., fibronectin, laminin, elastin, and tenascin), and proteoglycans that provide a hydrated gel that resists compressive forces.

Proteoglycans consist of a core protein and one or more covalently attached GAG chains. GAGs are linear polysaccharides, whose building blocks (disaccharides) consist of an amino sugar (either GlcNAc or GalNAc) and uronic acid (GlcA and IdoA). Virtually all mammalian cells produce proteoglycans and either secrete them into the ECM, insert them into the plasma membrane, or store them in secretory granules. The matrix proteoglycans include small interstitial proteoglycans (e.g., decorin, biglycan, and fibromodulin), a proteoglycan form of type IX collagen, and one or more members of the aggrecan family of proteoglycans (e.g., aggrecan, brevican, neurocan, and versican). Some of these proteoglycans contain only one GAG chain (e.g., decorin), whereas others have more than 100 chains (e.g., aggrecan). The matrix proteoglycans typically contain the GAGs known as chondroitin sulfate (CS) or dermatan sulfate (DS). Exceptions to this generalization exist, since the heparan sulfate (HS) proteoglycans, perlecan and agrin, are major species found in basement membranes. A number of different types of proteoglycans are also found within the ECM, including keratin sulfate.

Disruption of the ECM in animal tissues has been implicated in a number of disease processes. ECM deterioration has been associated with poor prognosis of many types of connective and hyperproliferative disorders. In particular, destabilization of proper ECM structure and function in human tissues such as breast and prostate tissues has been shown to aggravate the disease process in those organs. This disruption manifests itself in a number of indications, including overexpression of tRAS, inflammation, infection, loss of tissue integrity and biochemical imbalances in the cells contained within the matrix, and can lead to increases in mammographic density, microcalcification, degeneration of healthy tissue, and a number of neoplastic and other disease processes in situ. Accordingly, there is a need in the art for compositions that improve the health of ECM-rich mammalian tissues, limit ECM deterioration and dysfunction, increase stabilization of the ECM and its resident cellular cooperative, and reduce, eliminate, or prevent harmful cellular processes such as aberrant tRAS angiogenesis, inflammation, microcalcification, and the development of neoplastic disease.

BRIEF SUMMARY OF THE INVENTION

The present disclosure overcomes these and other limitations inherent in the prior art, by providing new and useful compositions (as well as methods of making and using them), that may advantageously improve mammalian cellular function, promote healthy tissue development, reduce inflammation, and/or stabilize one or more components of the mammalian ECM.

Accordingly, the present disclosure advantageously provides multi-component nutraceutical compositions and formulations thereof that facilitate stabilization of the ECM and provide a deterrent to chronic diseases, and in particular diseases of inflammatory origin. Using the present compositions, the inventors have demonstrated successful stabilization of the ECM can decrease the morbidity of chronic processes by reducing pain and preserving healthy organ function.

Persistent, moderate dosing of the exemplary nutraceutical formulations disclosed herein have proven to be a safe and effective method of stabilizing mammalian tissue matrices, particularly through their inhibition of aberrant biologic inflammatory pathways, and activation of intracellular antioxidative mechanisms that neutralize free radicals (e.g., nuclear factor erythroid 2-related factor, Nrf2).

The inventors' treatment paradigm links stabilization of the ECM to the avoidance, prophylaxis, and/or amelioration of one or more symptoms of disease, and in particular, one or more symptoms of inflammation including, without limitation, disorders, dyfunctions, diseases, and/or abnormal conditions of one or more tissues or organs, as well as trauma, injury, or repetitive exercise of skeletal muscles, skin, sunburn, dermal tissue damage, rosacea, tooth and gum pain, cervical dysplasias (including, for example, those caused by human papillomavirus [HPV] infection), herpes simplex virus (HSV) infection of the vulva or surrounding tissue, cold sores, primary and secondary dysmenorrhea, hemorrhoids, cancer of the breast and/or prostate, and the like.

Stabilization of the ECM in human breast and prostate tissues using one or more of the disclosed topical nutraceutical preparations has been implicated in: a) potentially inhibiting cancer initiation at the cellular level; b) decreasing tissue inflammation and lessening the promotion of tumor formation (especially through inhibition of angiogenesis and/or vasculogenesis); c) decreasing the activation of enzymes such as aromatase, as well as inhibiting production of those estrogen metabolites that are mitogenic and/or genotoxic; d) expediting the regression of occult cancers and other hyperproliferative conditions; e) encapsulating and rendering occult tumors dormant; and/or f) inhibiting one or more biochemical pathways, including one or more of those pathways that lead to, or participate in, the inflammatory cascade, or occult tumor progression and metastasis in situ.

Each of the active ingredients of the disclosed multicomponent formulations was selected based upon its inherent properties, including, for example, the ability to 1) block one or more ECM-disrupting metabolic pathways (e.g., inflammation); 2) reduce or neutralize one or more free radicals to prevent cellular oxidative damage; 3) neutralize or detoxify one or more harmful substances (e.g., genotoxins and related compounds); and/or 4) inhibit or reduce one or more growth factor (GF)-generating pathways that can aggravate or exacerbate one or more normal cellular functions.

Particular combinations of the active orthomolecular nutraceutical components disclosed herein have been shown to be synergistic in their inhibition of chronic inflammatory mediators, while the reported side effects associated with their administration to test subjects have been minimal. In important aspects of the present disclosure, a multi-factorial approach has been developed for treating, preventing, and/or ameliorating one or more symptoms of mammalian disease processes that are, by their very nature, multi-factorial.

In a significant advance over conventional prior-art monotherapy and/or duotherapy regimens (which typically focus on blocking only one or two of the cellular pathways involved in disease progression), the present disclosure provides multi-component, nutraceutical formulations that advantageously provide multiple active ingredients that collectively, and potentially synergistically, target one or more distinct biochemical pathways to provide multiple beneficial effects in treated individuals. Previously described monotherapy and duotherapy regimens have largely proven so far to be unsuccessful in the prevention or long-term resolution of most chronic diseases. The present disclosure also provides significant improvements over conventional therapies and regimens, by offering multicomponent formulations that effectively prevent and/or treat such conditions in animals.

In particularly advantageous embodiments, the inventors have formulated compositions that contain at least one active ingredient from each of at least three, at least four, at least five, or at least six or more principal nutraceutical groups, whose members have been shown to be advantageously beneficial in treating one or more mammalian conditions.

In exemplary embodiments, the disclosed formulations contain at least one active ingredient from each of the following five primary nutraceutical groups:

a) catechins (including, without limitation, their analogs and derivatives thereof); b) curcuminoids (including, without limitation, their analogs and derivatives thereof); c) isothiocyanates (including, without limitation, their analogs and derivatives thereof); d) stilbenoids (including, without limitation, their analogs and derivatives thereof); and e) therapeutic essential oils (EOs).

In particular embodiments, the present disclosure provides new and useful compositions that include: a) one or more catechins, catechin derivatives, or catechin analogs, agonists, or antagonists thereof; b) one or more curcuminoids, curcuminoid derivatives, or curcuminoid analogs, agonists, or antagonists thereof; c) one or more isothiocyanates, isothiocyanate derivatives, or isothiocyanate analogs, agonists, or antagonists thereof; d) one or more stilbenoids, stilbenoid derivatives, or stilbenoid analogs, agonists, or antagonists thereof; and e) at least one, at least two, or at least three or more therapeutic essential oils.

In an exemplary embodiment of the present disclosure, the ECM-stabilizing multi-component formulation preferably includes: a) one or more catechins, catechin derivatives, or catechin analogs, agonists, or antagonists thereof, each preferably present in the composition in an amount from about 0.0000001% to about 45% (by weight); b) one or more curcuminoids, curcuminoid derivatives, or curcuminoid analogs, agonists, or antagonists thereof, each preferably present in the composition in an amount from about 0.0000001% to about 25% (by weight); c) one or more isothiocyanates, isothiocyanate derivatives, or isothiocyanate analogs, agonists, or antagonists thereof, each preferably present in the composition in an amount from about 0.0000001% to about 25% (by weight); d) one or more stilbenoids, stilbenoid derivatives, or stilbenoid analogs, agonists, or antagonists thereof, each preferably present in the composition in an amount from about 0.0000001% to about 25% (by weight); and e) at least one, at least two, or at least three or more therapeutic essential oils, each preferably present in the composition in an amount from about 0.0003% to about 50% (by weight).

In further exemplary formulations, the orthomolecular nutraceutical compositions of the present disclosure preferably contain, without limitation: a) about 0.0001% to about 25%, by weight, of a catechin, catechin derivative, or a catechin analog, agonist, or antagonist thereof; b) about 0.00001% to about 2.5%, by weight, of a curcuminoid, a curcuminoid derivative, or a curcuminoid analog, agonist, or antagonist thereof; c) about 0.00001% to about 2.5%, by weight, of an isothiocyanate, an isothiocyanate derivative, or an isothiocyanate analog, agonist, or antagonist thereof; d) about 0.00001% to about 2.5%, by weight, of a stilbenoid, a stilbenoid derivative, or a stilbenoid analog, agonist, or antagonist thereof; and e) about 0.003% to about 5%, by weight, each of at least one, at least two, or at least three or more selected therapeutic essential oils.

Additional exemplary formulations of the present disclosure include, without limitation, a) about 0.001% to about 1.0%, by weight, of a catechin, catechin derivative, or a catechin analog, agonist, or antagonist thereof; b) about 0.001% to about 1.0%, by weight, of a curcuminoid, a curcuminoid derivative, or a curcuminoid analog, agonist, or antagonist thereof; c) about 0.001% to about 1.0%, by weight, of an isothiocyanate, an isothiocyanate derivative, or an isothiocyanate analog, agonist, or antagonist thereof; d) about 0.001% to about 1.0%, by weight, of a stilbenoid, a stilbenoid derivative, or a stilbenoid analog, agonist, or antagonist thereof; and e) about 0.01% to about 0.9%, by weight, each of at least one, at least two, or at least three or more selected therapeutic essential oils.

In particularly preferred embodiments, the formulations of the present disclosure include, without limitation, a) about 0.01% to about 0.5%, by weight, of a catechin, catechin derivative, or a catechin analog, agonist, or antagonist thereof; b) about 0.01% to about 0.5%, by weight, of a curcuminoid, a curcuminoid derivative, or a curcuminoid analog, agonist, or antagonist thereof; c) about 0.01% to about 0.5%, by weight, of a isothiocyanate, an isothiocyanate derivative, or an isothiocyanate analog, agonist, or antagonist thereof; d) about 0.01% to about 0.5%, by weight, of a stilbenoid, a stilbenoid derivative, or a stilbenoid analog, agonist, or antagonist thereof; and e) about 0.05% to about 0.75%, by weight, each of at least one, at least two, or at least three or more selected therapeutic essential oils.

The compositions of the present disclosure may also optionally, but preferably, further include one or more of: f) about 5% to about 15% of a transdermal penetrating base (such as one or more cyclodextrins, one or more lipophilic carriers [including, without limitation, transdermal bases such as lipocore (e.g., Lipoderm®), and the like]), as well as any combination or derivative thereof; g) about 1% to about 10% of isopropyl palmitate or isopropyl myristate, as well as any combination or derivative thereof; and h) about 0.000001% to about 12.5% of one or more of: a xanthan gum, an α-lipoic acid, melatonin, 3'3-diindolylmethane, a stilbene (such as pterostilbene), an isothiocyanate generator (such as broccoli seed oil, mustard seed oil, broccoli seed power, and the like), N-methyl pyrrolidone, vitamin D, quercetin, isoquercetin, vitamin $D_3$, vitamin E complex (including the related tocopherols and tocotrienols such as, without limitation, α-tocopherol, β-tocopherol, δ-tocopherol, γ-tocopherol, α-tocotrienol, β-tocotrienol, δ-tocotrienol, γ-tocotrienol, as well as derivatives and combinations thereof), cetearyl alcohol, ceteareth-20, phenoxyethanol, caprylyl glycol, sorbic acid, polyacrylamide based emulsion, sweet orange essential oil, and any combinations thereof.

In particular applications of the disclosed methods, anti-inflammatory compositions have been developed that may optionally, but preferably, further include one or more of: f) about 2% to about 10% of a transdermal penetrating base (such as one or more cyclodextrins, one or more lipophilic carriers [including, without limitation, transdermal bases such as Lipocore (e.g., Lipoderm®), and the like]); and g) about 0.000025% to about 7.5% of any one or more of: α-lipoic acid, melatonin, 3'3-diindolylmethane, pterostilbene, broccoli seed oil, mustard seed oil, broccoli seed power, N-methyl pyrrolidone, vitamin D, vitamin $D_3$, vitamin E, cetearyl alcohol, ceteareth-20, phenoxyethanol, caprylyl glycol, sorbic acid, polyacrylamide based emulsion, sweet orange essential oil, and any combinations thereof.

In another illustrative embodiment, the inventors have prepared and tested a topical formulation that includes the following orthomolecular nutraceutical compositions with active ingredients each present in the formulation in the stated concentration ranges: a) about 0.025% to about 12.5% of a curcuminoid; b) about 0.025% to about 12.5% of a catechin; c) about 0.025% to about 12.5% of an isothiocyanate; d) about 0.025% to about 12.5% of a stilbenoid; and e) about 0.1% to about 2.5% each of at least one, at least two, or alternatively, at least three or more, essential oils selected from the group consisting of rosemary, thyme, turmeric, clove, and frankincense (Boswellia).

In related illustrative embodiments, the formulations of the disclosed orthomolecular nutraceutical composition preferably includes, without limitation, a) about 0.025% to about 2.5% of a tetrahydrocurcuminoid or a tetrahydrocurcuminoid complex (e.g., Tetrahydrocurcuminoid-CG®), or one or more components thereof, or any combination thereof; b) about 0.025% to about 2.5% of a catechin, such as EGC-GINE®, CG, EC, EGC, EGCG, GA, lipo-EGCG, microencapsulated-EGCG, or any combination thereof; c) about 0.025% to about 2.5% of an isothiocyanate, such as broccoli seed oil, broccoli seed powder, Wasabia japonica extract, i-Sabi™, wintercress, watercress, as well as derivates or any combination thereof; d) about 0.025% to about 2.5% of a stilbenoid, such as pterostilbene, resveratrol, lipopterostilbene, as well as derivatives or any combination thereof; and e) about 0.1% to about 1.5% each of at least one, at least two, or at least three or more essential oils selected from the group consisting of rosemary essential oil, thyme essential oil, turmeric essential oil, clove essential oil, frankincense (i.e., Boswellic acids) essential oil, including, without limitation, essential oils from Boswellia sacra, Boswellia serrata and Boswellia carterii.

Optionally, but preferably, the compositions described in the present disclosure may further include one or more inactive (carrier) ingredients including, without limitation, one or more emollients (including, e.g., without limitation, isopropyl palmitate, isopropyl myristate, and combinations thereof); one or more surfactants (including, e.g., without limitation, cetearyl alcohol, ceteareth-20, and combinations thereof); one or more emulsification or rheology agents (including, e.g., without limitation, poloxamer 407 NF, pluronic F-127 NF, block copolymer of ethylene oxide and propylene oxide, polyacrylamide emulsion [Sepigel™ 305, Seppic, Inc., Fairfield, N.J., USA], and combinations thereof), xanthan gums and the like; one or more antioxidants [including, e.g., without limitation, α-lipoic acid, vitamin E (including tocopherols and tocotrienols, and their derivatives and combinations thereof) and combinations thereof]; vitamin D, and vitamin $D_3$); one or more solvents (including, e.g., N-methyl pyrrolidone); one or more preservatives (including, e.g., without limitation, phenoxyethanol, caprylyl glycerol, sorbic acid, and combinations thereof), one or more fragrances and/or perfumants (including, e.g., without limitation, one or more natural essential oils, such as sweet orange oil, and combinations thereof); melatonin, Carcinosin 30C, dimethylsulfoxide (DMSO), propylene glycol liquid, Phytolacca americana extract, or any combination thereof.

Optionally, the formulations of the present disclosure may further include one or more buffers (each preferably present in the final composition in an amount from about 1 µM to about 1 M), such as, without limitation: one or more of tris(hydroxymethyl) aminomethane (Tris), citrate, 2-(N-morpholino)ethanesulfonic acid (MES), N,N-Bis(2-hydroxyethyl)-2-aminoethanesulfonic acid (BES), 1,3-bis(tris (hydroxymethyl) methylamino)propane (Bis-Tris), 4-(2-hydroxyethyl)-1-piperazine ethanesulfonic acid (HEPES), 3-(N-morpholino)propanesulfonic acid (MOPS), N,N-bis(2-hydroxyethyl) glycine (Bicine), N-[tris(hydroxymethyl) methyl]glycine (Tricine), N-2-acetamido-2-iminodiacetic acid (ADA), N-(2-Acetamido)-2-aminoethanesulfonic acid (ACES), piperazine-1,4-bis(2-ethanesulfonic acid) (PIPES), bicarbonate, phosphate, and combinations thereof.

The inventors have found that the inclusion of one or more such buffers is desirable to control the pH of the resulting formulations, and particularly within the desirable range for administration to a mammal. In such instances, formulation of the compositions that include one or more buffers will preferably facilitate a final pH of the prepared compositions in the range of about pH 6.0 to about pH 8.0, and more preferably still, in the range of about pH 6.5 to about pH 7.5, and more preferably still, in the range of about pH 6.8 to about pH 7.2, which is often referred to as "near-physiological pH."

Further, optionally, the compositions of the present disclosure may further include one or more pharmaceutical compounds, phytochemicals, orthomoleculars, dietary supplements, nutraceuticals, or any combination thereof, including, for example, but not limited to, one or more non-steroidal antiinflammatory drugs (e.g., NSAIDs), including, for example, without limitation, one or more of acetaminophen, ibuprofen, naproxen, acetyl salicylic acid, salicylate, ketoprofen, fenoprofen, indomethacin, etodolac, ketorolac, diclofenac, nabumetone, piroxicam, oxicam, mefenamic acid, meclofenamic acid, flufenamic acid, tolfenamic, isoxicam, droxicam, celecoxib, and combinations thereof), menthol, capsaicin, camphor, methyl salicylate, arnica extract, methylsulfonylmethane (MSM), 2-methoxyestradiol, dimethylsulfoxide (DMSO), phenol, and combinations thereof.

Although the particular dosages, dosing schedules, duration, and frequency will be, in large part, patient- and/or condition-specific, the inventors have set forth general guidelines for administration of the preferred anti-inflammatory formulations described herein. While, in general, a suitable (i.e., prophylactically- or therapeutically-effective) amount (i.e., "dose") of the active ingredients of the present disclosure may depend upon a number of factors (including, for example, individual patient response, size of administration site, type of tissue, severity of inflammation, duration of administration, whether the condition is acute or chronic, the overall health of the individual, and the frequency of dosing, etc.) the inventors contemplate that the ordinary-skilled artisan, having benefit of the present specification, will select appropriate administration regimens to facilitate the individualized needs of each patient.

As a general guideline, for example, with respect to administration of the disclosed topical formulations to the human breast, a suitable (i.e., prophylactically- or therapeutically-effective) amount (i.e., "dose") of the active ingredients of the formulations of the present disclosure will typically include from about 0.05 cc to about 4 cc per breast, per day, more preferably, from about 0.1 cc to about 2.5 cc per breast, per day, and more preferably still, from about 0.25 cc to about 1 cc per breast, per day, with a typical dosing regimen of daily for the first 30-60 days of treatment, followed by maintenance dosing occurring 3 to 5 times a week thereafter. Quantity of dose will also depend upon the size of the individual breast (i.e., "cup" size). For example, for administration to A- or B-cup breasts, a dosage of 0.25 cc/breast/day is recommended; for C-cup sized breasts, a dosage of 0.5 cc to 0.75 cc of the topical formulation/breast/day is recommended, while women with D-cup or larger breasts will typically benefit from larger doses of the topical formulation (for example, in the range of about 0.75 cc to about 1.5 cc of topical formulation applied to each breast each day).

When used as a topical "sports cream" or "muscle ache relief" cream (whether in a prophylactic, or preventative regimen, or specifically to reduce one or more untoward symptoms of exercise, physical exertion, fitness training, and such like), a suitable application regimen will typically include the administration of one or more daily doses of a therapeutically- or prophylactically-effective amount of the formulation to the affected area(s). For example, a dosage of about 0.1 cc to about 1 cc per square inch of skin surface to which the topical formulation is applied, typically from anywhere between about 15 minutes to about 1 or 2 hours before engaging in exercise, sporting activity, physical exertion, and such like has been shown to provide beneficial effects. Such formulations may also be applied one or more times after engaging in physical activity, and in such applications, similar dosing regimens are contemplated to be beneficial. Depending upon the extent of the activity or exertion, such applications may be administered over the course of several doses, including, for example, over the course of a few hours to a few days, as may be desirable.

When used as a topical formulation in the treatment of acute inflammation, a contemplated therapeutic regimen employing one or more of the disclosed formulations typically involves administration of about 1 cc to about 2 cc dose/square inch of administration site typically either every 4 to 6 hr, every 8 hr, or alternatively, twice-daily, for as long as symptoms persist.

Conversely, when used as a topical formulation in the treatment of chronic or persistent inflammation, a contemplated therapeutic regimen employing one or more of the disclosed formulations typically involves administration of an about 1 cc- to an about 2 cc-dose of the transdermal preparation per square inch of tissue to which the formulation is applied, usually daily, for at least about 7 to about 14 days or more, as recommended, followed by maintenance dosing (typically about 3 to about 5 days per week), as needed thereafter, for as long as symptoms persist.

With respect to insertional administration (e.g., intravaginally or intrarectally by suitable means such as, for example, a suppository formulated to contain the active ingredients disclosed herein), the contemplated dosing regimen will typically include 0.5 to 1.5 cc of the formulation impregnated onto or within a suppository vehicle, with suppositories being introduced once or twice daily for the first 30 to 45 days, followed, preferably, by maintenance dosing occurring, for example, 3 to 5 times a week thereafter as long as symptoms persist, or as advised by the supervising physician or medical practitioner.

In each of the foregoing embodiments, the bioactive orthomolecular phytochemical formulations of the present disclosure may be administered alone, or, alternatively, in combination with one or more additional pharmaceutical(s), active ingredient(s), or other conventional therapies, or in combination with one or more dietary supplements, vitamins, change-of-diet, or such like. The particular formulations of phytochemicals and supplements may be designed for co-administration, such as in combination therapies, or, alternatively, in one or more different compositions for consecutive, sequential, or otherwise separate administration regimens, as recommended or deemed beneficial by the attending medical personnel/physician/health-care provider, etc.

Preparation of Medicaments

Another important aspect of the present disclosure concerns methods for using the disclosed compositions, and in particular, topically- or transdermally-delivered compositions, as well as formulations including one or more of them, in the preparation of one or more medicaments for preventing, treating or ameliorating one or more of the symptoms of one or more various diseases, dysfunctions, disorders, abnormal conditions, or deficiencies in an animal (and particularly in vertebrate mammals such as humans). Use of the disclosed compositions is also contemplated in prophylaxis, therapy and/or amelioration of one or more symptoms of one or more diseases, disorders, dysfunctions, abnormal conditions, disabilities, deformities, trauma, or deficiencies in an animal (and in particular, those involving the regulation, modulation, or attenuation of one or more aspects of inflammation, infection, cancer, or such like) and preferably in a mammal, including, without limitation, in humans.

Such use generally involves administration to an animal in need thereof one or more of the disclosed pharmaceutical compositions, in an amount and for a time sufficient to prevent, treat, lessen, or ameliorate one or more symptoms of a disease, disorder, dysfunction, defect, abnormal condition, trauma, injury, or deficiency in the affected animal, or one or more symptoms thereof. In exemplary embodiments, the disclosed compositions are prepared as medicaments for promoting the health of mammalian tissues, such as human breast tissue in particular; reducing inflammation and/or infection; preventing tissue calcification; and maintaining the integrity of the ECM in mammalian tissues, and preferably in tissues of humans.

Compositions including one or more of the disclosed multi-component nutraceutical formulations also form part of the present disclosure, and particularly those formulations that further include at least a first pharmaceutically-acceptable excipient for use in the therapy, prophylaxis, or amelioration of one or more symptoms of disease in a mammal, and particularly in humans.

The compositions of the present disclosure may optionally further include one or more additional inert ingredients, reagents, nutraceuticals, dietary phytochemicals, vehicles, additives or adjuvants, as may be suitable for administration to an animal, and preferably to a mammal.

The use of one or more of the disclosed compositions in the manufacture of a medicament for prophylaxis, therapy, or amelioration of one or more symptoms of a disease, dysfunction, disorder, defect, trauma, injury, or abnormal condition is also an important aspect of the present disclosure. Formulation of such compositions for use in administration to an animal host cell, and to a mammalian host cell in particular, is also provided by the invention. In certain embodiments, the present disclosure also provides formulations of such compositions for use in administration to a human, or to one or more selected human host cells, tissues, and/or organs in situ and/or in vivo. The present disclosure also provides for the use of one or more of the disclosed multi-component formulations in the manufacture of a medicament for the prophylaxis or prevention of one or more diseases, disorders, dysfunctions, or conditions, including the preparation of one or more compositions suitable for prophylactic administration to prevent or ameliorate one or more diseases, disorders, or conditions in a mammal, and in a human in particular.

The present disclosure further provides methods for administering a therapeutic- and/or prophylactic-effective amount of one or more of the disclosed orthomolecular multicomponent compositions to at least a first population of cells or to one or more tissues within the body of a mammal. Such methods, in an overall and general sense, include, without limitation, providing to one or more selected mammal(s) in need thereof, an amount of a composition as disclosed herein, and for a time effective, to provide the desired therapy and/or prophylaxis in the selected cells and/or tissues of the recipient mammal.

In particular embodiments, administration to the ECM of a population of cells and/or tissues is particularly contemplated to be beneficial in promoting cellular health, reducing inflammation and/or infection, modulating aberrant tRAS-induced growth factor and angiogenesis, and reducing the risk for developing more serious diseases, including, for example, neoplastic disorders and the like.

Nutraceutical Formulations & Transdermal Administration Thereof

In certain aspects, the present disclosure provides nutraceutical compositions, and formulations thereof, that are suitable for topical administration to one or more mammalian host cells. The five aforementioned classes of active ingredients are unique in their ability to collectively inhibit an extensive number of disparate biologic pathways, each of which has been previously implicated in destabilization of one or more components of the mammalian ECM. In particular, the presence of isothiocyanates and/or curcuminoids has been implicated in activating various components of the cellular anti-oxidation process, and in particular those that function via Nrf2. As previously reported, isothiocyanates and curcuminoids are known to disrupt the Nrf2-Keap1 association thereby releasing Nrf2, which translocates to the cell nucleus, while also driving gene expression of particular detoxifying enzymes. It has been shown that glutathione production, for example, is enhanced by these active ingredients along with activation of quinone reductase, which is a known neutralizer of carcinogenic agents.

Yet another advantage of the present invention may include active ingredient(s) and pharmaceutical formulations and compositions thereof, for treating or ameliorating one or more symptom(s) of a disease, disorder, dysfunction, trauma, injury, or abnormality in a mammal. Such methods generally involve administration to a mammal, and in particular, to a human, in need thereof, one or more of the disclosed nutraceutical orthomolecular compositions, and/or formulations thereof, in an amount and for a time sufficient to prevent, treat, ameliorate the one or more symptom of, or lessen the severity, duration, or extent of, such a disease, disorder, dysfunction, injury, trauma, or abnormality in such a mammal.

The methods and compositions disclosed herein may also be used in prevention, prophylaxis, and/or vaccination of an animal that has, is suspected of having, is at risk for developing, is expressing one or more clinical symptoms, or has been diagnosed as potentially having one or more disorders or diseases, either before, during, or after diagnosis or the onset of one or more symptoms of the disorder or disease, or one or more clinical indications or manifestations of at least a first symptom thereof.

In certain embodiments, the mammalian host cells are preferably human host cells. In the practice of the invention, the disclosed compositions may be administered to a selected animal (e.g., "a patient") using any of a number of conventional methodologies, including, without limitation, one or more of topical, intradermal, subdermal, transdermal, transmucosal, intravaginal, intrarectal, transvaginal, intramuscular, and/or any other suitable routes, including, but not limited to, administration, by diffusion, sonophoresis, iontophoresis, micro-needle/nano-needle delivery, insertion, impregnated patches, creams, liquid suspensions, sustained-release dermal patches, or any combination thereof, as may be indicated for the particular condition for which the composition is being used.

Pharmaceutically-Acceptable Carriers, Diluents, and Vehicles

Bioactive compositions disclosed herein preferably include effective amounts of one or more of the active ingredients of the invention dissolved or dispersed in a pharmaceutically-acceptable carrier or medium. The phrases "pharmaceutically or pharmacologically acceptable" refer to molecular entities and compositions that do not produce an adverse, allergic or other untoward reaction when administered to an animal, and preferably when administered to a human, as appropriate.

As used herein, "pharmaceutically-acceptable carrier" includes any and all solvents, solutions, delivery vehicles, cream bases, dispersion media, coatings, antibacterial and antifungal agents, isotonic, absorption-delaying agents, and the like. The use of such media and agents for pharmaceutical active substances is well known in the nutraceutical and pharmaceutical arts. Except insofar as any conventional media or agent is incompatible with the active ingredients, its use in the prophylactic and therapeutic compositions disclosed herein is contemplated. As noted herein, one or more supplementary active or inactive ingredients can also be incorporated into the compositions as desired, insofar as the preparations meet required sterility, pyrogenicity, general safety and/or purity standards as required by FDA Office of Biologics standards, or other suitable regulatory authority.

Solutions and topical vehicles of the active ingredients are preferably prepared as denoted in the following Examples, but may optionally be formulated using one or more conventional pharmacological compounding/preparation methods useful in achieving the desired properties of the resulting preparation, while maintaining the integrity of the formulation, and the potency of the active ingredients incorporated therein. For example, the active ingredients may be formulated as a free base or one or more pharmacologically-acceptable salts or derivatives thereof, and can be prepared in an aqueous phase, suitably mixed with one or more surfactants, emollients, binders, carriers, or dermal/mucosal delivery vehicles as known to one of ordinary skill in the pharmaceutical compounding arts. Under ordinary conditions of storage and use, the disclosed preparations will preferably contain one or more preservatives to prevent or reduce the growth of microorganisms within the formulation.

Active ingredients of the disclosed therapeutic and prophylactic formulations may be formulated into a composition in a neutral or salt forms, including, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride.

Generally, delivery vehicles are prepared by incorporating the various active ingredients into a sterile medium that contains the basic dispersion medium, as well as any other optional ingredients including those enumerated herein.

Upon formulation, solutions will be administered in a manner compatible with the dosage formulation and in such amount as is prophylactically- and/or therapeutically-effective for at least a first indication in a mammal, and preferably, for at least a first indication in a human.

Each of the active agents enumerated herein may be formulated by compounding within the final administered formulation to comprise from about 0.0001 to about 500 milligrams, alternatively from about 0.001 to about 200 milligrams, or more preferably still, from about 0.01 to about 50 to 100 milligrams per dose or so. Single or multiple doses can be administered over the course of 24 hours, with one single, daily dose being most conveniently preferred.

In addition to the particularly preferred routes of topical, transdermal, and transmucosal administration, the compounds disclosed herein may also be optionally formulated for administration to the mammalian patient through any other conventional administration method, including, for example, timed- or controlled-release delivery vehicles; as well as any other form conventionally used in the delivery of nutraceutical bioactive ingredients described herein.

Additional formulations, which are suitable for treatment for particular conditions, include, for example, formulation of the active ingredients into a suppository. Such delivery routes are particularly contemplated to be useful for rectal or vaginal insertion, such as, for example, by rectal transmucosal delivery for the treatment and/or amelioration of one or more symptom of prostatitis and the like, or by intravaginal or transvaginal delivery for the treatment and/or amelioration of one or more symptoms of dysmenorrhea, vaginal pain, swelling, itching, cervical dysplasia, and the like.

For suppositories, traditional binders and carriers may include, for example, one or more polyalkylene glycols, triglycerides, and the like; suppositories in accordance with the practice of the disclosed methods will preferably be formed from one or more mixtures containing the active ingredients, each present in the formulation in a range of about 0.005% to about 30%, and more preferably, in the range of about 0.01% to about 5.0%.

Liposomal or Nanocapsule Formulations

In certain embodiments, the use of nutraceutical-loaded, biodegradable microspheres, nanospheres, microparticles, nanoparticles, as well as nutraceutical-containing liposomes and/or lipid-containing formulations, including, without limitation, one or more polymer conjugates and/or one or more sustained-release adjuncts is contemplated for the introduction of the active nutraceutical orthomolecular reagents of the present disclosure into suitable animal host cells and tissues.

Nanocapsules can generally entrap compounds in a stable and reproducible way. To avoid side effects due to intracellular polymeric overloading, such ultrafine particles (sized around 0.1 µm) may be designed using polymers that are degraded in vivo. For example, biodegradable polyalkylcyanoacrylate nanoparticles that meet these requirements are contemplated for use in the present disclosure, and such particles may be are easily made by those of ordinary skill in the pharmaceutical formulatory arts.

Liposomes are formed from phospholipids that when dispersed in an aqueous medium spontaneously form multilamellar concentric bilayer vesicles (also termed multilamellar vesicles [MLVs]). MLVs generally have diameters from about 25 nm to about 4 µm. Sonication of MLVs results in the formation of small unilamellar vesicles (SUVs) with diameters in the range of about 200 Å to about 500 Å, containing an aqueous solution in the core in which the active nutraceutical ingredients disclosed herein may be contained.

Such formulations may be preferred for the topical, transdermal administration of the nutraceutical-based anti-inflammatory formulations disclosed herein. The formation and use of liposomes is generally known to those of ordinary skill in the art (see for example, U.S. Pat. No. 5,741,516, specifically incorporated herein in its entirety by express reference thereto). Further, various methods of liposome and liposome like preparations as potential drug carriers have been described (see e.g., U.S. Pat. No. 5,567,434; U.S. Pat. No. 5,552,157; U.S. Pat. No. 5,565,213; U.S. Pat. No. 5,738,868 and U.S. Pat. No. 5,795,587, each of which is specifically incorporated herein in its entirety by express reference thereto). Alternatively, the nutraceutical formulations disclosed herein may be prepared in liposomal or nanocapsule preparations to improve or facilitate uptake, absorption, delivery, or permeation of the active ingredients across the skin or cellular membrane. Exemplary nanoparticle formulations are set forth in U.S. Pat. No. 5,145,684 (specifically incorporated herein in its entirety by express reference thereto), and the references cited therein.

Vehicles for Transdermal Delivery of Nutraceutical Formulations

A transdermal, enhanced-penetration base that contains one or more active ingredients from each of the five primary nutraceutical groups disclosed herein facilitates a localized concentrated dosing regimen directly to the desired area(s) of the body to be treated. Saturation of the ECM of by localized administration to the tissues facilitates clinically-effective levels of each class of nutraceutical to be achieved by convenient, once- or twice-daily topical application to the region(s) of interest. Tissue levels ranging from micromolar to nanomolar have been realized for actives from each of the five families of nutraceutical ingredients described herein. In particular, use of a lipocore base cream (e.g., PCCA Lipoderm® transdermal base, PCCA USA, Houston, Tex., USA) facilitated ready uptake of the active ingredients in the tissues immediately in and around the application site(s). Peer-reviewed literature suggests that tissue dosing in the micro- to nano-molar range is both necessary and sufficient for achieving a therapeutic benefit. Oral ingestion, which requires absorption through the intestines and then liver, followed by general distribution throughout the body results in lesser nanomolar to picomolar tissue concentrations.

Adaptogenic capabilities, synergistic effects, and broad-range coverage to ensure neutralization of biologic ECM disruptors were important considerations in choice of formulation ingredients. The current medical paradigm of one "new-to-nature molecule" or drug to block one biologic cellular disruptor has proven inadequate. Because of their highly specific targets, effectiveness of multiple combinations of these drugs has been limited by toxicity, and by the ability of the chronic disease process to evolve alternative paths negating any therapeutic value. The present formulations intervene at multiple levels in potentially disruptive biologic pathways to offer a significantly enhanced scope of treatment.

Adaptogens are substances that help the ECM adapt to changes in the cellular environment. For example acting in the role of an "agonist," if a low stimulation of a specific biologic process exists in the ECM, an adaptogen may stimulate and activate the pathway to balance the matrix. Conversely, adaptogens can function as "antagonists" by down-regulating a chronic dysfunctional hyperfunctioning biologic pathway.

Included in exemplary formulations of the present orthomolecular compositions are cyclooxygenase (COX) inhibitors (e.g., curcuminoids) which down regulate COX-2 overexpression, but do not inhibit COX-1, and conversely, activate the Nrf2 intracellular antioxidative system that upregulates abnormally-suppressed COX-2 by activating one or more "detoxifying" genes in situ.

Synergism, the combination of two or more substances to achieve a more comprehensive desired biologic effect at lowered doses than what could be realized using each substance individually, represents an important benefit of the disclosed multi-component therapeutic and prophylactic formulations. Because these compositions preferably include at least one active ingredient from at least four or at least five different families of phytoactives, e.g., one or more isothiocyanates, one or more curcuminoids, one or more stilbenoids, one or more catechins (including, for example, the combination of multiple chemical sub-families within a given broad family of active ingredients (e.g., the inclusion of diindolylmethane and sulforaphane, or combinations of one or more of their derivatives, analogs, or active metabolites) and one or more essential oils, a significant advantage of the present invention is the synergy that results from combinational therapies using multi-component formulations. Oral or topical agents including quercetin and its analog, isoquercetin (which have been shown to synergistically enhance the effects of catechins, isothiocyanates, and stilbenoids), may also be incorporated into formulations and/or treatment regimens discussed herein. Such synergy represents an important advantage of the present invention over conventional mono- and duo-therapy regimens.

Coverage is the combination of substances to achieve broader or more expanded biologic effects than would be realized by use of single components. Multiple ECM-disrupting inflammatory, stromal remodeling, and neovascular pathways are known to exist. Single orthomolecular ingredients could not be expected to adequately interact with multiple pathways, but the combination of a number of active ingredients, as provided by the disclosed formulation, provides a broader coverage of the molecular pathways implicated in disease progression and in the disruption of the ECM.

The topical formulations disclosed and described herein were designed to be adaptogenic, synergistic, and capable of providing a broad coverage in order to inhibit the multiple ECM disrupting inflammation pathways, neutralize free radicals, detoxify genotoxins, and inhibit aberrant growth factor generating pathways. Moreover, side effects associated with these five groups of orthomolecular compounds have been shown to be minimal.

Therapeutic and Prophylactic Kits

The present disclosure also encompasses one or more of the orthomolecular reagents formulated together with one or more pharmaceutically-acceptable excipient(s), carrier(s), diluent(s), adjuvant(s), and/or other component(s), as may be employed in the formulation of particular pharmaceutical formulations, and in the preparation of therapeutic agents for administration to an animal, and in particular, for administration to mammalian species, including humans. Such kits preferably include one or more of the disclosed compositions in combination with instructions for using the composition in the treatment, prevention, and/or amelioration of one or more symptoms of a given disease, dysfunction, disorder, trauma, injury, or abnormal condition in a mammal, and may typically further include one or more containers suitable for facile commercial packaging, shipment, and/or product wholesaling, retailing, or patient acquisition. In illustrative embodiments, commercial transdermal formulations of the compositions are contemplated for use as breast creams, sports/muscle creams, inflammation-reducing topical creams, and such like. In additional illustrative embodiments, commercial transmucosal rectal suppository formulations of the compositions are contemplated for reducing inflammation and/or infection of the male prostate.

In addition to administration in human patients, other animals contemplated to benefit from the disclosed nutraceutical formulations include, without limitation, non-human primates, ovines, bovines, equines, lupines, porcines, canines, felines, exotics, as well as other animals under veterinary care.

Prophylactic kits may also be prepared that comprise at least one of the nutraceutical compositions disclosed herein and instructions for using the composition as a prophylactic agent, and particularly in the prevention or delay of onset of one or more symptoms of one or more conditions such as, without limitation, prostatitis, disorders of the ECM, infection, musculoskeletal aches and pains, acute or chronic inflammation, hemorrhoids, cellulitis, skin disorders, hyperproliferative or neoplastic disease, breast calcification, CIS (and in particular, DCIS), as well one or more dysfunctions, disorders, diseases, or abnormal conditions of the human mammary gland, its supportive and/or connective tissue, and such like.

Containers for such kits may typically comprise at least one vial, tube, flask, jar, bottle, dispenser, or other suitable containment device, into which the disclosed composition(s) may be placed, and preferably suitably aliquotted either for individual use, or for hospital, commercial, or direct-to-patient sales. Where a second composition or an additional therapeutic or prophylactic reagent is also provided, the kit may also contain a second distinct container into which this second composition may be placed. Alternatively, the plurality of therapeutic or prophylactic compositions may be prepared in a single topical formulation, and may be packaged in a single container such as a vial, tube, flask, bottle, jar, dispenser, or other suitable single container, device, or kit.

Therapeutic and prophylactic treatment kits as disclosed herein may also typically be adapted and configured to contain the aliquotted anti-inflammatory compositions in close confinement for commercial sale, such as, e.g., injection or blow-molded plastic containers into which the desired containment device is retained. Such kits may further optionally include instructions for administration of the composition, one or more material safety data sheet(s), one or more ingredient list(s), one or more drug monograph(s), one or more dosing protocol(s), as well as one or more advertising material(s), product brochure(s), insert(s), and such like.

BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 1 shows illustrative results obtained using the disclosed orthomolecular formulations in one preferred aspect of the present disclosure;

FIG. 6A and FIG. 6B show the composition of exemplary topical formulations in other particular aspects of the present disclosure;

FIG. 8A, FIG. 8B and FIG. 8C demonstrate an illustrative in vivo study of one formulation of the present invention using the oxazolone-induced murine ear edema model. In FIG. 8A, pre- and post-topical formulation administration reduction of ear edema swelling is circled. Shown is the effect of treatment on oxazolone-induced murine ear edema. 103% of the efficacy of betamethasone-positive control was obtained using an exemplary topical cream formulation of the orthomolecular anti-inflammatory composition (BC1) in accordance with one aspect of the present disclosure. In this study, the cream was applied prior to, and post-insult, 30 min, 6 hrs, 12 hrs, "Proactive;" FIG. 8B shows experimental data from the preliminary oxazolone edema study illustrated in FIG. 8A. FIG. 8C illustrates circles results of post-oxazolone induced ear edema reduction by topical orthomolecular application in this in vivo study, and shows the effect of treatment on oxazolone-induced murine ear edema;

DESCRIPTION OF ILLUSTRATIVE EMBODIMENTS

Figure 2A:
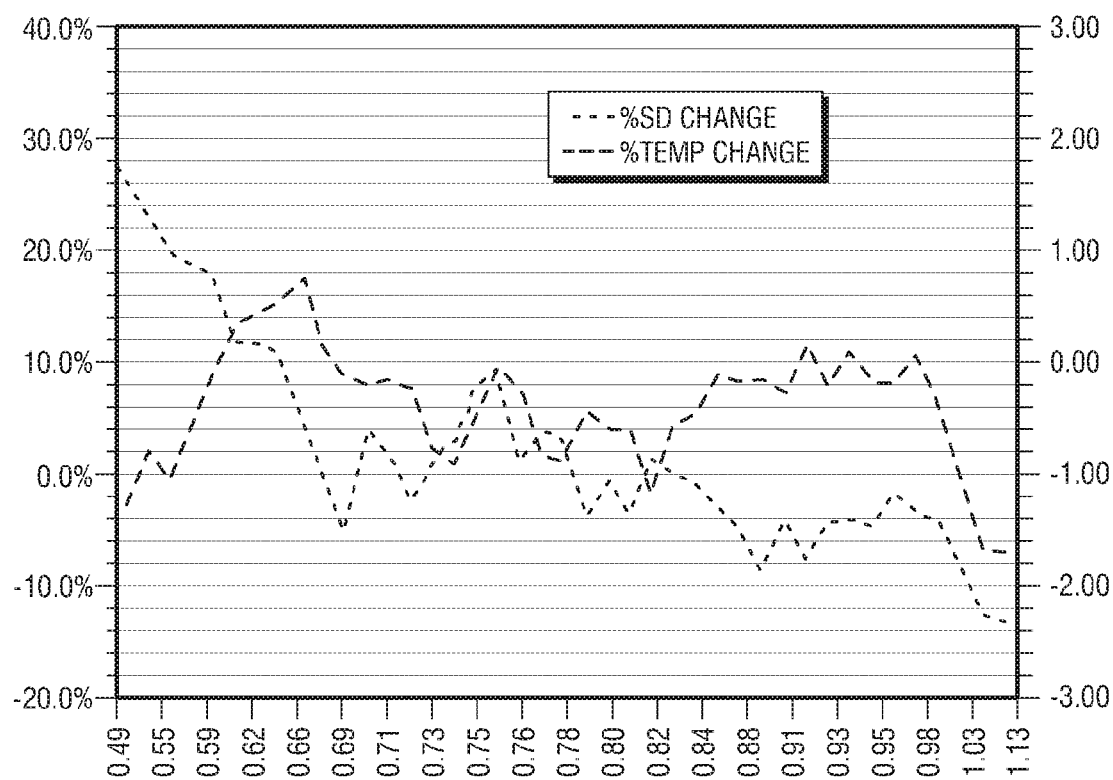
FIG. 2A and FIG. 2B provide illustrative results obtained using the disclosed orthomolecular formulations in another preferred aspect of the present disclosure.
Figure 2B:
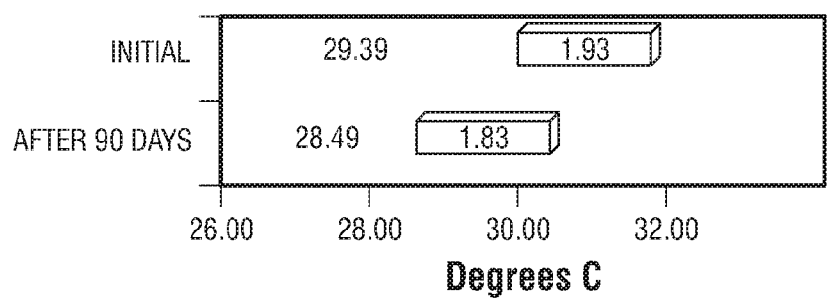
Figure 3:
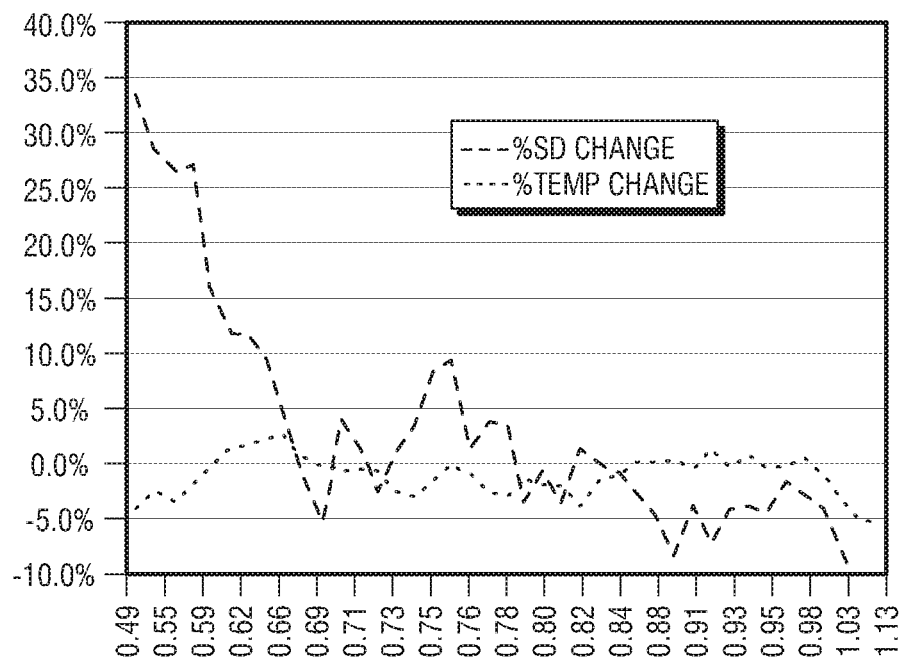
FIG. 3 shows exemplary results obtained from a human patient study involving topical administration of the disclosed orthomolecular composition; The change in standard deviation and the change in temperature in percentage (%) across all the patients using breast cream formulation 1 (BC1) for 90 days as a function of the initial standard deviation is shown.
Figure 4:
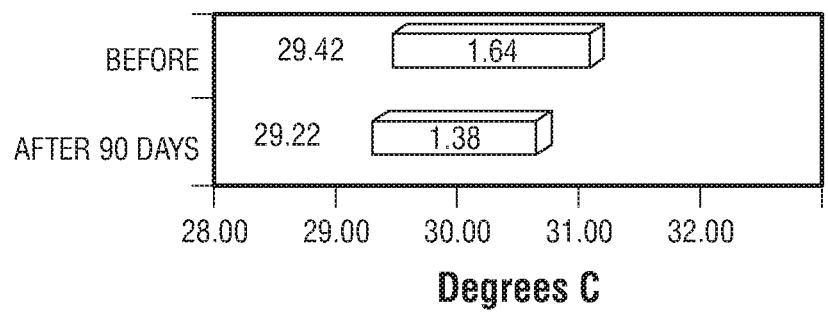
FIG. 4 shows exemplary results obtained from a human patient study involving topical administration of the disclosed orthomolecular composition in accordance with one aspect of the present invention. Shown is the temperature range of ±1 standard deviation before and after using breast cream formulation 1 (BC1) for 90 days (° C.) with mean value and range.
Figure 5:
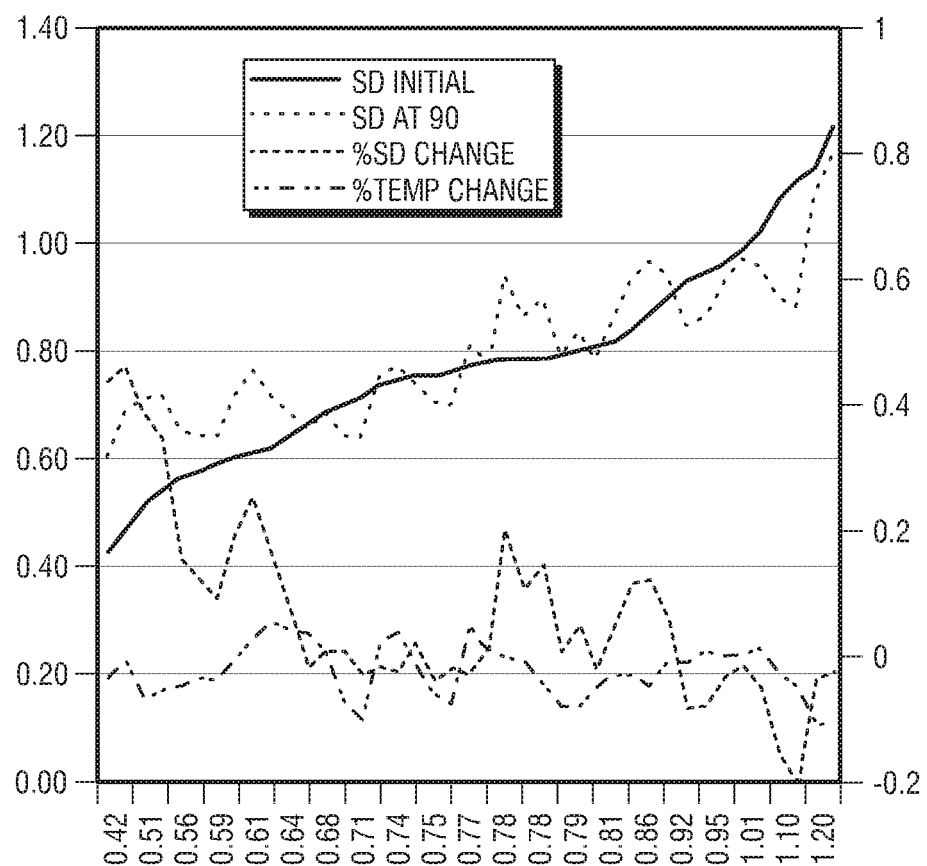
FIG. 5 shows additional exemplary results from a human patient study involving topical administration of the disclosed orthomolecular compositions. Shown are results of change in standard deviation in a breast cream study using MD Matrix Health Breast Cream Formulation 1 (BC1)

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Inflammation, Characterized by Overexpression of the Oxidoreductases, COX-2 and LOX, and its Implication in Chronic Disease A December 2010 report by the United States Department of Health and Human Services stated that more than 25% of Americans have at least two or more chronic conditions that require continuing medical care; such conditions often limit the abilities of those afflicted in performing the activities of daily living. The human suffering and economic implications of this staggering statistic demands a reassessment of the current medical paradigm for treatment of "chronic" diseases. An ever-increasing aging population now manifests chronic conditions (including, e.g., autoimmune diseases, degenerative osteoarthritis, joint and/or muscle pain, cardiovascular disease, dementia, Alzheimer's and other neurological conditions, gastrointestinal and skin afflictions, and neoplastic processes such as cancer and related hyperproliferative disorders.

The biochemical and physiological origins of many such diseases are inextricably linked to the ongoing biologic processes of the inflammatory response in general, and to that of chronic inflammation in particular. The biologic response of tissue to prolonged inflammation is an underlying factor shared by many chronic diseases. The cause and intensity of chronic inflammation depends upon many factors, such as the environment, aging, lifestyle, diet, and genetics, to name only a few.

Biologically-active molecules associated with chronic inflammation include, but are not limited to, NFκB, AP-1, COX-2, LOX, iNOS, HIF-1α, and one or more cytokines including, without limitation, Tumor Necrosis Factors (TNF) such as TNF-α, Prostaglandins (PG) such as PGE2, Leucotrienes, Interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, and IL-17; Transforming Growth Factors (TGF), including TGF-α and TGF-β; as well as interferons (IFN) such as IFN-γ. These pro-inflammatory mediators promote "downstream" activation of other inflammatory cytokines, chemokines, and growth factors, such as, but not limited to, vascular endothelial growth factor (VEGF); epithelial growth factor (EGF); matrix metalloproteinases (MMP) including, for example, MMP-9 and MMP-14; and platelet-derived growth factor (PDGF), and the like.

Oxidative stress is caused by an imbalance between the production of reactive oxygen and the breakdown of reactive intermediates such as peroxides and free radicals. Severe oxidative stress leads to inflammatory changes that result in the acceleration of chronic diseases such as atherosclerosis, Alzheimer's disease, and diseases linked by pathological fibrosis. Cellular induction of one or more "detoxifying" and/or antioxidant enzymes represents a key defense mechanism in the human body's response to oxidative stress. Nrf2 crosses the cell nuclear membrane and attaches to the DNA anti-oxidant response element (ARE). Activation of ARE decreases the degree of chronic inflammation and supports breakdown of potential abnormal growth factor stimulants by trans-activating enzymes including, inter alia, glutathione-S-transferase, cytochrome $P_{450}$, NAD(P)H quinone oxidoreductase, and superoxide dismutase.

Chronic inflammation is an ongoing destructive process that not only compromises tissue but also elicits the body to over respond and produce potentially harmful substances. The relationship between chronic inflammation and chronic disease has been noted by many in the peer-reviewed scientific literature (see, e.g., O'Byrne and Dalgleish, 2001). Examples include Alzheimer's disease involving the excessive production of amyloid beta plaque whose level is linked to pro-inflammatory mediators. A vicious feed-forward cycle is initiated by the disturbed degradation of amyloid and the triggering of inflammatory processes in microglial and astrocytes.

Atherosclerosis is mediated by the body's excessive response to injury of the coronary blood vessels by chronic inflammation. Calcium rich plaques are formed at the site of injury that can lead to total occlusion, and death of cardiac tissue. The initiation, promotion, and progression of cancer depend, in large part, upon chronic inflammation. Numerous studies have shown that the inflammatory process promotes initiation of cancer (see, e.g., Marks et al., 2007). In breast tissue up to 72% of DCIS was associated with an over expression of COX-2 (see, e.g., Perrone et al., 2005). Tumors upon reaching a size of 1 to 2 mm must release inflammatory derived angiogenic molecules such as VEGF to sequester blood vessels for nutrients. In a cohort of women living at least one year after being diagnosed with breast cancer, aspirin use was associated with an almost 50% decrease in distant recurrence and breast cancer death (see, e.g., Holmes et al., 2010).

Chronic pain (which afflicts almost 105 million people in the United States) often accompanies, and is frequently aggravated by, chronic inflammation. Degenerative arthritis, which has increased secondary to an aging population, accounts for a significant proportion of diagnosed chronic pain. Continued wear of joint surfaces along with an increased influx of inflammatory molecules, especially those mediated by COX-2, results in destruction of the fragile joint membranes, capsules, and cartilage. Pain, localized erythema, and swollen synovium are all key indicators of the inflammatory process. Calcification, fibrosis, and compromised ligament support are each chronic disease processes that result in loss of joint function and debilitating pain.

The current paradigm for treatment of chronic disease is directed toward inhibition of a specific chronic inflammatory biologic pathway at the somatic or cellular level (see, e.g., Baker et al., 2010). Drugs, most often in the form of "new-to-nature" molecules, are synthesized to block the biologic pathways in hopes of correcting aberrant cellular processes linked to a chronic disease. In most situations, one synthesized molecule is used to block one specific inflammatory pathway. Reducing inflammation acts to help alleviate symptoms but does not necessarily promote healing or establish long-term prevention. Some common drug groups, which have been used to control the symptoms of chronic inflammation, are opioids, NSAIDS, non-narcotic analgesics, and steroids. Other chronic conditions rely on medications such as chemotherapy, which inhibit inflammatory induced growth factor pathways.

Drug mediated total inhibition of a biologic pathway has been frequently shown to result in adverse, even life threatening, side effects. VIOXX® (rofecoxib, Merck and Co., White House Station, N.J., USA), which has since been removed from the market, blocked both COX-1 and COX-2 enzymes. While COX-2 is the primary enzyme for production of inflammatory molecules, COX-1 has an important role in the clotting mechanism of the blood. Blockage of both enzymes resulted in adverse side effects, including death of certain severely affected individuals.

NSAIDs and aspirin are commonly used to relieve both acute joint pain (often caused or aggravated by overuse, trauma, injury), as well as chronic debilitating conditions such as degenerative arthritis. While these two drug classes both alleviate pain, they also inhibit repair of the joint by blocking formation and deposition of chondroitin sulfate (see, e.g., Brandt, 1987). AVASTIN® (bevacizumab, Genentech/Roche, South San Francisco, Calif.) is an anti-angiogenesis drug that inhibits VEGF and that has been used in treating certain forms of breast cancer. Recently, the United States (US) Food and Drug Administration (FDA) issued a recall based on data that showed severe side effects and no overall improvement in survivability (Chang et al., 2010). Prolonged use of these medications can lead to cerebral vascular, cardio vascular, gastrointestinal, and renal complications (Ejaz et al., 2004).

Implication of Tissue Renin-Angiotensin System (tRAS) in Chronic Disease

The tissue Renin-Angiotensin System (tRAS) is a hormonal system expressed in a variety of epithelial tissues including normal and malignant breast cells. Although RAS has been associated with regulation of cardiovascular homeostasis, research has shown that local RAS or "tRAS" influences non-cardiovascular tissues (including, the breast, joints, liver, kidney, brain, heart, reproductive organs, pancreas, and colon) extracellular matrix by controlling angiogenesis, cell proliferation, apoptosis, fibrosis, and inflammation ""tRAS" components include the main effector-angiotensin 2 (ANG 2-), angiotensinogen, angiotensin-1, ANG (1-7), angiotensin converting enzyme (ACE), angiotensin receptors, and (pro) renin.

Two components of tRAS include angiotensin-2 (ANG-2) and renin. ANG-2 is a potent regulator of blood pressure, while exerting a variety of physiologic effects including maintaining circulating blood volume, stimulating neovascularization, and cell growth. Renin, an enzyme that produces angiotensin, is found in cancer blood vessels. Long-term administration of pharmaceutical agents that act on the tRAS (such as ACE inhibitors), have been shown to lower blood pressure while reducing morbidity and mortality in cancer patients. From these studies, researchers now suggest a role for blocking ANG-2 in addressing carcinogenesis. Studies show that elements of the tRAS are capable of destabilizing the ECM to potentiate the occurrence of chronic disease including tumorigenesis.

Evidence suggests that tRAS acts through local paracrine mechanisms, not its circulating counterparts, with regards to destabilization of the extracellular matrix. The destabilization of a specific tissue's ECM by aberrant tRAS determines the chronic affliction as illustrated by examples: a) joint involvement results in osteoarthritis, b) breast-increased mammographic density and tumorigenesis, c) skin-wrinkles, rosacea, d) cardiovascular-atherosclerosis, and e) colon-tumorigenesis.

As with all biologic systems, physiologic homeostasis is maintained by molecules that are antagonistic and that promote cell growth. It is the imbalance within a system, such as tRAS's peptides and receptors, which often leads to ECM destabilization and subsequent chronic disease. While ANG(1-7) has been found to be anti-angiogenic, pro-apoptotic, and anti-proliferative, ANG-2 exhibits opposite effects. Upregulation or overexpression of specific tRAS components (such as receptor AT1R) often accompanies the progression from normal to malignant phenotypes. AT2R antagonizes the effects of AT1R by supporting apoptosis and blocking aberrant blood vessel formation.

tRAS's primary role in causation of chronic disease is by its ability to destabilize the ECM through induction of fibrosis and/or fostering aberrant blood vessel formation. Fibro-proliferative diseases include pulmonary fibrosis, liver cirrhosis, cardiovascular disease, progressive kidney disease, macular degeneration, carcinogenesis, and mammographically-dense breast tissue. These conditions are characterized by stiffening and increased collagen deposition within the ECM. ANG-2, the major effector of tRAS, stimulates the expression of both pro-angiogenic and pro-growth factors such as VEGF, angiopoietin-2, basic fibroblast growth factor-2, and platelet-derived growth factor. The major functions of ANG-2 involve angiogenesis, migration, and inflammation that are related to the onset of chronic disease processes including cancer progression.

Residing in the breast stroma, ANG-2 activates fibroblast in the breast ECM to produce thrombospondin-1 (TSP-1). TSP-1 increases transforming growth factor-beta (TGF-β), which in turns stimulates hyaluronan and collagen 1 synthesis and their subsequent excretion into the ECM. Activation of PI3K/Akt pathway by TGF-β induces collage 1 production. Excessive amounts of hyaluronan combined with collagen 1 remodels the breast ECM increasing mammary fibrosis, which results in mammographically-dense breast. Stiffening the breast ECM leads to compression of blood vessels fostering a desmoplastic tumor friendly hypoxic environment. Replacement of normal breast tissue with excessive amounts of fibrotic ECM especially in post-menopausal women carries almost a 6 fold increased risk of breast cancer.

Inappropriate production of TSP-1 has been implicated in the occurrence of aggressive breast cancer within the first five years following cessation of breastfeeding. Post-WHI studies have also suggested that the increased metastatic potential of medroxyprogesterone acetate (17α-hydroxy-6α-methylprogesterone; PROVERA™) associated breast cancers was in part due to Provera's stimulation of TSP-1.

tRAS also influences tumorigenesis by activation of epithelial mesenchymal transformation (EMT) which is characterized by a series of cellular and structural changes which enhances cell motility by allowing loss of apical-basal cell polarity and modification of cell adhesions by lowering E-cadherin. EMT-induced cell proliferation, and metastatic migration are also potentiated by a rigid ECM containing VEGF and ANG-2 derived growth factors.

Receptors in the tRAS have been shown to influence the ECM. AT1R combines with ANG-2 to increase MMP-2 and MMP-9 activity that mediates the degradation of the ECM basement membrane. Further destabilization of the ECM is accomplished by ANG 2 induced synthesis of vascular permeability factors (e.g., endothelin-1 [ET-1]), nitric oxide, NFκB, and prostaglandins), which combine with VEGF to increase leaky microvascular densities allowing endothelial cells to migrate into the surrounding stroma. ANG(1-7) is an ANG-2 antagonist that reduces tumoral fibrosis by causing a decrease in production of TGF-β1 and a lowering of collagen 1 deposition in the ECM.

RAS is also present with joint tissue. Studies have documented that ANG-2 and its receptors impact joint health, particularly in the case of rheumatoid arthritis (RA) or osteoarthritis. In RA patients, fibroblast-like synoviocytes have been shown to express AT1R and ANG-2, which encourages synovial expansion by protecting synoviocytes from apoptosis. Inflammatory arthritis is characterized by tRAS induced chronic synovial hypoxia with synovial hypoperfusion, and synovial proliferation. Blocking AT1R with angiotensin receptor blockers improved RA in rodents.

Proper levels of glycosaminoglycans (GAGS) in the ECM of the joint cartilage are necessary to avoid osteoarthritis. Recent studies have noted when renin-angiotensin levels increase, GAG levels decline in osteoarthritic cartilage. Similarly, de novo synthesis of GAGs occurs with the use of pharmaceutical renin-angiotensin inhibitors providing a non-NSAID treatment for osteoarthritis (Evron, 2007).

Pharmaceutical intervention demonstrates the role of tRAS in promoting chronic disease by destabilization of the ECM. The angiotensin receptor inhibitor, losartan, decreases excess amounts of stromal collagen and hyaluronan while down-regulating the profibrotic signals TGF-β1, CCN2, and ET-1. Physical forces exerted by a matrix with excessive amount of hyaluronan and collagen, reduce physiologic vascular perfusion and increases areas of hypoxia. Losartan's reduction of solid stress by blocking ATR-1 has been shown to increase perfusion in hypoxic areas of the ECM minimizing both fibrosis and tumorigenic potential.

Stabilization of the ECM

The failure of the current paradigm justifies the need for a new approach in treating affected individuals. Instead of focusing on what occurs solely within the cell, prevention and resolution of chronic disease must now focus on the biological processes that originate and manifest in the glue-like ECM surrounding those cells. Each organ system in the mammalian body has its own unique ECM that has optimized over time to: 1) provide structural integrity to support and bind tissues together while maintaining a normalized morphostatic gradient; 2) regulate, control, and support metabolism and the biologic activity of cells by providing a conduit for nutrients into, and waste removal from those cells; 3) maintain a physiological stasis of fluids and a local homeostatic environment for the cells; 4) provide structural integrity, and immunologic protection; and 5) communicate (often, directly) with the nucleic acids inside each cell using receptor-mediated pathways and cascades, such as, for example, those involving the activity of integrins, syndecans, and related proteins.

Because the cell is "aware" of and able to respond to its external environment, the ECM must therefore be considered to act as a continuum with the cell surface, cytoskeleton and, ultimately, the nucleus. Contained within the ECM are capillaries, nerves, stromal cells, myeloid cells, bio-active inflammatory molecules including free radicals, potential carcinogens, and growth factors.

Chronic inflammation disrupts the microenvironment adversely affecting tissue organization. The resultant disruption is both a precursor and a promoter of chronic disease. A compromised ECM can lead to: a) the disruption of structural integrity, fostering hypoxia, mechanical stiffening of tissue, and compromising organ function which potentiates tumor cell progression and metastasis; b) symptoms such as both acute and chronic pain; c) potential unstable cell clones from escaping, resulting in neoplastic growths; d) further promotion of excessive production of growth factors and pro-angiogenic agents, which potentiate the chronic disease process; and e) recruitment of surrounding cells to further the disease process by enhanced inflammatory mechanisms.

Cell biologists such as Carlos Sonnenschein, incorporating the ECM functions discussed previously, have formalized a tissue-based theory of chronic disease, denoted the "tissue organization field theory" (TOFT) (Sonnenschein and Soto, 2008). Inflammation-producing agents (along with biologic systems that induce stromal remodeling) generate a disruption in the reciprocal interactions between cells that maintain tissue organization, tissue repair, and local homeostasis. The resultant altered microenvironment favors relaxation of the negative controls exerted by tissue organization. Consequently, parenchymal cells would be allowed to exercise their constitutive ability to proliferate and migrate. From the TOFT perspective, the explanation for chronic diseases especially cancer reside at the level of biologic organization; hence, resolution of chronic inflammation is imperative to achieve stabilization of the ECM with appropriate tissue organization. ECM stabilization allows the cell to be contained while maintaining contact with its external environment and neighboring cells.

An intact ECM supports cell, tissue, organ, and organ system integrity by providing for the proper physiologic functioning of each biologic entity. Chronic alteration of this microenvironment resulting in a prolonged state of dysfunction will lead to end-stage structural alterations that are termed "pathological." Examples of end-stage structural alterations from prolonged ECM disruption are represented by the chronic disease states previously discussed. Stabilization of the ECM represents a defense against the onset and progression of chronic disease. For these reasons, highly vascularized tissues, including the human breast and prostate provide an excellent site of administration for the present compositions, and obtain useful and quick-onset benefits from the stabilization of the ECM, and maintenance of proper tissue function as afforded by the multi-component active ingredient formulations described herein.

In particular, the mammalian breast, having a unique anatomical separation from the majority of the other body tissues, is readily amenable to topical application of the disclosed compositions, and particularly for transdermal orthomolecular formulations thereof. Franz skin testing has confirmed the skin penetration potential of the principal transdermal base used in formulating the compositions in translocating the active ingredients (catechins, curcuminoids, isothiocyanates, stilbenoids, and essential oils) deeply into the breast ECM. The inherent vascularity of breast tissue also readily facilitates distribution of the active ingredients throughout the entire breast tissue at therapeutically- and prophylactically-beneficial levels. Studies have also shown that localized administration to breast tissue also readily facilitates systemic uptake of the active ingredients through the entire vascular system also at therapeutically- and prophylactically-beneficial levels.

TOFT, as discussed previously, is an alternative paradigm, which presents a more plausible explanation for these observations. Given that the default state of cells in metazoa is proliferation, it would not be abnormal for cells found in unicellular organisms, metaphyta, or metazoa to continually divide. The need to proliferate also explains the driving force behind evolution. Individual cells therefore must be held in place by biological scaffolding, the ECM, to prevent this basic directive of continued proliferation. In 1962, Dr. D. W. Smithers (Royal Marsden Hospital, London) wrote in the medical journal, *The Lancet*, "cancer is no more a disease of cells than a traffic jam is a disease of cars. A lifetime of study of the internal-combustion engine would not help anyone understand our traffic problems." Dr. Smithers argued that cancer was not a disease caused by a rogue cell that divides and multiples until it destroys its host. Instead, he postulated, cancer was a disorder of cellular organization. An increasing abundance of contemporary literature seems to validate the prescience of this nearly five-decade old observation, and motivates the adoption of a new paradigm to treat chronic disease.

The functional unit of the breast is defined as the "terminal ductal lobular unit" (TDLU). Architecturally the lobule is composed of a layer of luminal epithelial cells surrounded by a basal layer of myoepithelial cells. The lobular unit is encased within a heterogeneous microenvironment composed of the extracellular matrix (ECM) and stromal cells.

From both a histological and a molecular perspective, breast cancer is thought to evolve from a linear progression of TDLU cell alterations: normal→hyperplasia→atypical hyperplasia→in-situ cancer, and finally overt invasive cancer. These incremental histologic molecular progressions are influenced not only by gene expression but also by destabilization of the ECM manifesting in a loss of cell orientation, aberrant cell division, and ultimately tissue invasion.

Based on the TDLU model, atypical hyperplasia can manifest as either ductal (ADH) or lobular (ALH); similarly, in-situ cancer is either ductal carcinoma in-situ (DCIS), or lobular carcinoma in-situ (LCIS). Invasive cancer is categorized as either invasive ductal or invasive lobular. The lifetime relative risks (RR) for developing breast cancer in those women with atypical hyperplasia is 3.5 to 5.3 while those with carcinoma in-situ have a RR score of 10 to 11.

The biologic energy expended by the increased metabolic needs of atypical hyperplastic, pre-invasive (in situ) and invasive breast tissue require ever increasing amounts of blood flow. Quantification of this tissue blood flow is accomplished by estimating the number of micro vessels per mm of tissue or "microvascular density" (MVD). Studies have determined an MVD value (in vessels/mm) for each of the cell architectural stages: a) normal tissue: 86±3, b) hyperplasia: 79±7, c) atypical ductal hyperplasia: 119±10, d) atypical lobular hyperplasia: 109±5, e) ductal carcinoma in situ: 146±38, and f) lobular carcinoma in situ: 117±7.

MVD directly correlates with levels of the pro-angiogenic extracellular matrix derived vascular endothelial growth factor (VEGF). Proteases that are responsive to chronic inflammatory conditions modulate the release of VEGF from the matrix influencing the degree of MVD within the tissue.

VEGF not only increases vascular permeability, but also is the angiogenic switch that provides the necessary blood flow (hence increasing the MVD) for the transition of hyperplastic cells to malignant tumors. Tumor supporting angiogenesis is accomplished by specialized endothelial cells (tip cells) which establish new microvessel formation by following the VEGF gradient and invading the ECM. The mechanical strain of the ECM provides traction and orientation for the newly formed vessels.

The increase in MVD provides a larger infrared signature secondary to increased blood flow. The densities changes can best be seen on the gray scale and appear as a softer gray brushing between the larger feeder vessels. Breast thermography's detection of areas with increased MVD can be suggestive but not diagnostic of abnormal cell growth. Importantly, increased breast density (which often limits the accuracy of mammograms) does not affect the thermographic evaluation.

The following examples illustrate use of transdermal orthomolecular nutraceutical formulation discussed in this patent re-stabilizes or prevents the initial destabilization of the extracellular matrix thus reducing the concentration of tissue VEGF. The decline in VEGF results in a diminished area of MVD that can be visualized as a decrease in the infrared thermographic signal. Limiting the blood supply would lead to a regression of aberrant cell growth while favoring the re-normalization of tissue.

Breast Calcification

The breast matrix, calcium, and bone proteins are linked by milk formation, which is the primary biologic function of the breast. Insight as to why breast cancer metastasizes to bone primarily is linked to this connection. Breast microcalcifications, when observed by mammography in particular configurations, give concern on the potential development of neoplastic processes. Two different types of microcalcifications are observed in the human breast: calcium oxalate (associated with benign lesions) and hydroxyapatite (noted more often in malignant lesions). Calcium oxalate is commonly found in kidney stones while hydroxyapatite is the primary calcium in bone. They obey different molecular mechanisms. The ECM of the breast is modified to allow formation of the calcifications. Degeneration of tissue with replacement of calcium is one example. Bone matrix proteins, especially bone sialoprotein (BSP), control the deposition of hydroxyapatite in the ECM. BSP is found only in malignant cells, and its levels correlate with metastasis and poor survival.

Hydroxyapatite crystals in breast tissue affect the cell by stimulating mitogenesis in quiescent and malignant cells. The calcium crystal, by simply lying next to a quiescent cell and rubbing against it, can make the quiescent cell undergo a malignant transformation. This phenomenon has been attributed to at least the following distinct mechanisms: 1) fast membrane associated events involving protein kinase C and mitogen-activated protein kinase (MAPK) activation, nuclear factor-kappa B (NF-κB), and proto-oncogenes; and 2) increase of intracellular calcium resulting in activation of calcium-dependent processes leading to cell proliferation.

Research has also shown that the health and integrity of the ECM is directly influenced by the formation of hydroxyapatite crystals, which can lead to destabilization by: a) induction of matrix metalloproteases (MMP's), and MMP-1, MMP-2, MMP-9, and MMP-13 in particular; and/or b) activation of COX-2 and prostaglandin E2 (PGE2) production.

Destabilizing the ECM and promoting a cell clone with malignant potential that can overcome a weakened matrix illustrates some of the many dangers of this form of microcalcification. Inflammation has been shown to be at the heart of this event cascade.

Orthomolecular Multi-Component Formulations S for Stabilizing ECM and Promoting Mammalian Tissue Health Catechins As noted in the report by Catravas et al. (2004), the polyphenolic components of green tea, and in particular, epicatechin gallate (ECG) and epigallocatechin-3-gallate (EGCG), have potent anti-inflammatory properties. EGCG has been shown to inhibit tumor necrosis factor-alpha (TNF-α)-mediated activation of the NF-κB pathway, partly through inhibition of IκB kinase (IκK). The NF-κB pathway may also be activated in response to interleukin-1β (IL-1β) stimulation through a distinct signal transduction pathway. Shankar et al. (2008) have shown that EGCG inhibits ANG2 induced angiogenesis by blocking the Ras/MEK/ERK pathway.

In particular aspects of the invention, an antioxidant, such as a catechin (and in particular, epigallocatechin-3-gallate [EGCG]), is an active ingredient in the disclosed anti-inflammatory, ECM-stabilizing topical formulations.

However, in other embodiments, one or more alternative antioxidants, and in particular other catechins, catechins analogs, catechin derivatives, and/or agonists or antagonists thereof (as well as catechin- and/or catechin-derivative-rich nutraceuticals) may be substituted in place of ECG as an active ingredient in the exemplary formulations enumerated herein.

Exemplary antioxidant- and/or catechin-rich compounds and nutraceuticals include, without limitation, aspalathin, nothofagin, catechin, catechin gallate (CG) epicatechin (EC), epigallocatechin (EGC), epigallocatechin-3-gallate (EGCG), gallic acid (GA), L-theanine, botanical extracts (including "teas" and extracts obtained from *Camellia sinensis* leaves (e.g., "green tea extract"), *Camellia* spp. twigs (e.g., Kukicha tea extract), *Aspalathus linearis* (red bush) leaves and stems (e.g., Rooibos tea), and oils or pressings of the fruit, leaves, stems, and/or seeds of members of the Oleaceae (including, for example, the *europaea, cuspidate, guanchica, cerasiformis, maroccana,* and *laperrinei* subspecies of the Mediterranean olive, *Olea europea*), and combinations thereof.

Curcuminoids

Curcumin is the primary curcuminoid (along with are-desmethoxycurcumin and bis-desmethoxycurcumin) in the rhizomes of the plant *Curcuma longa*, a member of the ginger family (Zingiberaceae), and the source of the popular Indian spice, turmeric. Curcuminoids are naturally occurring phenolic compounds that are responsible for the yellow color of turmeric. Curcumin exists in both the "keto" and "enol" tautomeric forms, with the enol form being more energetically stable in both solution and solid-phase forms. Curcumin inhibits the 5-lipoxygenase activity in rat peritoneal neutrophils as well as the 12-lipoxygenase and the cyclooxygenase activities found in human platelets. In a cell-free peroxidation system, curcumin exerted strong anti-oxidative activity. Thus, its effects on the dioxygenases are probably due to its reducing capacity.

Extensive scientific research on curcumin, demonstrated its anti-inflammatory action. Curcumin was found to inhibit arachidonic acid metabolism, cyclooxygenase, lipoxygenase, cytokines (e.g., IL and TNF) NF-κB and release of steroidal hormones. Curcumin was reported to stabilize lysosomal membrane and cause uncoupling of oxidative phosphorylation besides having strong oxygen radical scavenging activity, which was responsible for its anti-inflammatory property. In various animal studies, a dose range of 100-200 mg/kg body weight exhibited good anti-inflammatory activity and seemed to have negligible adverse effect on human systems. Oral $LD_{50}$ in mice was found to be >2 g/kg body weight (Kohli et al., 2995). Curcumin attenuates the actions of ANG 2 by inhibiting ACE and blocking AT1R expression. Reduction of ANG2 activity inhibits excess deposition of collagen-1 by the tRAS induced MAP/ER kinase pathway. Remodelling of the matrix secondary to overproduction of collagen-1 allows for increased invasiveness and metastasis of tumor cells.

In particular aspects of the invention, one or more curcuminoids, including the Tetrahydrocurcuminoid CG® (Sabinsa Corp., East Windsor, N.J., USA) components: a) tetrahydrodiferuloylmethane, b) tetrahydrodemethoxydiferuloylmethane, and c) tetrahydro-bisdemethoxydiferuloylmethane, as well as, tetrahydropiperine, may be included as active ingredients in the disclosed multi-component orthomolecular formulations.

However, in other embodiments, one or more alternative curcuminoids, and in particular other curcuminoids analogs, derivatives, and/or agonists or antagonists thereof (as well as curcuminoid- and/or curcuminoid-derivative-rich nutraceuticals) may be substituted for Tetrahydrocurcuminoid CG® as active ingredients in the exemplary anti-inflammatory formulations enumerated herein.

Exemplary preferred curcuminoid- and/or curcuminoid-rich compounds and nutraceuticals include, without limitation, SabiWhite® (tetrahydrodiferulolyl-methane [Sabinsa Corp.]) as well as analogs or derivatives thereof.

Isothiocyanates

Glucosinolates are bio-inactive plant glucosides found in cruciferous vegetables (including, for example, broccoli, broccolini, broccoli raab (rapini), Brussels sprouts, cauliflower, turnip, radish, cabbages, as well as some leafy vegetables such as arugula, bok choy (Brassica chinensis), mustard, kale, kohlrabi, watercress, Swiss chard, and extracts thereof. In addition to glucosinolates, Cruciferae contain vacuoles, which act both to isolate and to contain the enzyme "myrosinase" (a thioglucosidase).

The biologic function of the glucosinolate and myrosinase system in the presence of water most likely represents a defense mechanism developed by the plant against insects and/or disease. As the insect begins to eat the plant, the cell wall is ruptured allowing the glucosinolates to mix with and undergo hydrolysis catalyzed by myrosinase. This biochemical reaction elicited in the Cruciferae (plant, sprout, seed, or oil distillate) results in the formation of isothiocyanates, glucose, thiocyanates, and nitriles.

Isothiocyanates are orthomolecular, bioactive, sulfur-containing phytochemicals that have the general formula R—N=C=S. They have been shown to have strong anti-carcinogenic and anti-inflammatory effects that act to stabilize the ECM. Each member of the Cruciferae contains its own specific glucosinolate, which upon myrosinase-induced hydrolysis, gives rise to plant specific isothiocyanates. Examples include but are not limited to: 1) broccoli family—contains glucoraphanin conversion to the isothiocyanate, sulforaphane; 2) watercress family—contains gluconasturtin conversion to β-phenylethyl-isothiocyanate; and 3) white mustard or mustard family—contains sinablin conversion to 4-hydroxybenzyl isothiocyanate. Each isothiocyanate possesses its own unique chemical characteristics, and potential usefulness in ECM stabilization.

Sulforaphane (SFN) is an organosulfur isothiocyanate compound, which, as previously noted, is derived from the glucosinolate "glucoraphanin." Of the cruciferous vegetables, broccoli sprouts have been shown to possess the highest native concentrations of glucoraphenin, which can be hydrolyzed to sulforaphane. Watercress and wintercress are plant sources containing isothiocyanates derived from gluconasturtiin (phenethylglucosinolate; ([3-phenyl-1{[2S, 3R, 4S, 5S, 6R)-3,4,5-trihydroxy-6-(hydroxymethyl)-2-tetrahydro-pyranyl]thio}propylidene]amino]hydrogen sulfate. These major glucosinolate metabolites, β-phenylethyl glucosinolate [PEITC; β-phenylethyl-isothiocyanate,] white mustard seed oil; (2-isothiocyanatoethyl)benzene] and the (methylsulfinyl)alkyl glucosinolates, 7-methylsulfinyloctyl and 8-methylsulfinyloctyl, are active ingredients that may be included in the orthomolecular formulations of the present disclosure. PEITC is formed from phenylalanine, and methylsulfinylalkyl ITCs contain methionine. These ITC compounds stabilize the ECM by: 1) inhibition of phase 1 carcinogenic activation enzymes; 2) induction of phase 2 enzymes (e.g., quinone reductase, glutathione-S-transferase, and UDP-glucuronosyl-transferase); 3) activation of stress-activated protein kinase pathway mediated by JNK; and 4) inhibition of angiogenesis through interference with the function of hypoxia inducible factor (HIF).

Along with diindolylmethane (another compound isolated from members of the Brassicaea), sulforaphane has been shown to inhibit cancer growth in vitro, and in experimental animal models, sulforaphane was shown to down-regulate the Wnt/β-catenin self-renewal signaling pathway in breast cancer stem cells. SFN has the ability to induce phase 2 detoxification enzymes, as well as to inhibit Phase 1 enzymes involved in carcinogen activation. Phase 2 enzyme inducers have also been found to have anti-inflammatory activity. SFN has been shown to inhibit MMP (matrix metalloproteinase) production in pro-inflammatory cytokine-stimulated chondrocytes. This is an example of how SFN provides a safe and effective therapeutic way of preventing cartilage degradation.

In addition, SFN modulates the Nrf2/Keap1 pathway. Nrf2 activation leads to a coordinated antioxidant and anti-inflammatory response, while Keap1 represses Nrf2 activation. Nrf2 has been shown to increase Nrf2-regulated cell defense in some human cancer cell lines. Moreover, SFN inhibits NF-κB, whose activation results in inflammation and suppression of COX-2 (lipopolysaccharide-induced cyclooxygenase-2). SFN suppresses both the LPS-induced COX-2 protein and mRNA expression. Isothiocyanates such as SFN block the ANG-2 induced Akt and NFkB pathways.

SFN inhibits breast cancer stem cells also by down regulating the Wnt/β-catenin self-renewal pathway. In addition, SFN arrests proliferation and mitosis in MCF7 breast cancer cells by stabilizing the microtubules. SFN also inhibits the expression of Estrogen Receptor (ER) alpha protein (ER-α) in MCF-7 cells by inhibiting ER-α mRNA transcription as well as by a mechanism that possibly involves increased proteasome-mediated degradation.

The use of isothiocyanates in a topical orthomolecular formulation presents special challenges not encountered with oral administration. Considerations include: 1) activation of myrosinase-induced hydrolysis in a container or upon topical application; 2) long-term stabilization of the already formed isothiocyanate in a container (oral administration relies on the formation of the isothiocyanate by mastication or conversion by intestinal bacteria); and 3) limiting offensive odors and skin irritation derived not only from the isothiocyanate but its precursor glucosinolate.

For activation of the myrosinase-induced hydrolysis of a glucosinolate in a topical formulation, one must consider the available source of myrosinase and potential rate-limiting inhibitors of isothiocyanate production. Levels of myrosinase can vary according to plant stages of growth. Broccoli sprouts contain higher levels of myrosinase than mature broccoli plants. Preparation of semi-purified plant powders by heating or other drying methods can affect the heat-sensitive myrosinase levels.

Epithiospecifier Protein (ESP) directs the myrosinase-catalyzed hydrolysis of glucosinolates towards formation of the bio-inactive epithionitriles. ESP would diminish the amount of sulforaphane or other bioactive isothiocyanates in favor of nitrile compounds. Choosing a source of myrosinase requires limiting or excluding ESP. Mustard seed oil contains acceptable levels of myrosinase without ESP. This would explain why agriculture researchers refer to the crop protecting myrosinase induced hydrolysis of glucosinolates as "activation of the mustard oil bomb." White mustard seed oil may be used in the disclosed topical formulation as one source of myrosinase.

Stabilization of the isothiocyanate in the container used for topical application depends on the individual isothiocyanate molecule. For example, activating the myrosinase catalyzed hydrolysis of mustard seed essential oil's glucosinolate, sinalbin, results in the formation of the unstable 4-hydroxybenzyl isothiocyanate (4HBITC). 4HBITC is destroyed within 1 to 4 hrs in an aqueous cream environment. Therefore, mustard seed oil contains no isothiocyanates, but instead is used as a reservoir for myrosinase. Sulforaphane in topical formulations has been shown to incrementally decline to a zero level in 30 days. Generation of isothiocyanates by use of specific cruciferous powders in combination with myrosinase-containing oils such as mustard seed requires a cream base that is capable of long-term storage stabilization.

Popularly known, as the hot garnish "wasabi" that accompanies Japanese sushi and sashimi, *W. japonica*, in its native form, is grown in remote regions at precise temperatures and elevations. Also known as Asian horseradish, *W. japonica* is a member of the cruciferous plant family, and is a potent source of long-chain isothiocyanates. 6-(methylsulfinyl) hexyl isothiocyanate (6-MITC) is a bioactive compound extracted from *W. japonica*, which has many therapeutic effects including anti-oxidant, anti-carcinogenic, and anti-inflammatory properties.

An important mechanism for wasabi's anti-carcinogenic effect may be associated with its anti-inflammatory activity through the modulation of COX-2. 6-MITC acts a potent inhibitor of COX-2 expression induced by lipopolysaccharide (LPS), and IFN-gamma (IFN-γ). 6-MITC also demonstrates anti-carcinogenic properties, and directly affects human cancer cells by inhibiting their growth in culture. In addition, 6-MITC has been shown to inhibit cell proliferation in human monoblastic leukemia U937, and in human stomach cancer MKN45 cells by inducing apoptotic cell death.

In particular aspects of the current disclosure, one or more isothiocyanates, such as, without limitation, a sulforaphane, a sulforaphene, a β-phenylethyl-isothiocyanate (PEITC), a 7-methylsulfinylhelptyl isothiocyanate, an 8-methylsulfinyloctyl isothiocyanate, a wasabi powder, i-Sabi™ powder, or one or more derivatives, analogs, or combinations thereof, represent particularly useful ingredients in the disclosed multi-component orthomolecular anti-inflammatory compositions. Sulforaphene, a naturally-derived isothiocyanate [4-isothiocyanato-(1R)-(methylsulphinyl)-1-(E)-butene], is isolated from seeds of radish (*Raphanus sativus* L. cruciferae, and is also derived from the glucosinolate, glucoraphenin. Sulphoraphene, like sulphoraphane, is a potent inducer of phase-2 detoxification enzymes and consequently has potential anti-cancer action. In vitro induction of the phase-2 enzyme, quinone reductase (QR), has been shown to be significantly greater for sulforaphene than for sulforaphane.

i-Sabi™ is a commercially available form of *W. japonica* powder (BioCell Technology, LLC Newport Beach, Calif., USA), with demonstrated high levels of isothiocyanates (~15,000 ppm), and tetrahydrodiferuloyl-methane as its primary active component. However, in alternative embodiments, one or more other isothiocyanates, and particular other isothiocyanate analogs, derivatives, and/or agonists or antagonists thereof (as well as isothiocyanate- and/or isothiocyanate-derivative-rich nutraceuticals) may be substituted in place of wasabi powder as an active ingredient in one or more of the disclosed anti-inflammatory topical formulations.

Stilbenoids

Stilbenoids are secondary products of heartwood formation in trees that possess phytoalexin properties. In chemical terms, they are hydroxylated derivatives of stilbene. In biochemical terms, they belong to the family of phenylalanine derivatives known as phenylpropanoids. Much of their biosynthetic pathway is shared with those of the aromatic chalconoids, such as chalcone.

The most well-characterized botanical stilbenoid is resveratrol (3,5,4'-trihydroxy-trans-stilbene), a resorcinol derivative first isolated in 1939 from the white hellebore (*Veratrum album*), which is found in the skin of red grapes, and in other fruits and nuts including berries and peanuts. Resveratrol is a phytoalexin, polyphenolic compound, and multiple lines of compelling evidence indicate its beneficial effects on neurological, hepatic, and cardiovascular systems. In addition, one of the most striking biological activities of resveratrol is its cancer-chemopreventative potential. In fact, recently it has been demonstrated that this stilbene blocks the multistep process of carcinogenesis at various stages: tumor initiation, promotion, and progression. Possible mechanisms for its biological activities involve: a) down regulation of the inflammatory response through inhibition of synthesis and release of pro-inflammatory mediators; b) modification of eicosanoid synthesis; c) inhibition of activated immune cells; and/or d) inhibition of enzymes such as inducible nitric oxide synthase (iNOS) and cyclooxygenase-2 (COX-2) via its inhibitory effects on NF-κB or activator protein-1 (AP-1) (see e.g., de la Lastra and Villegas, 2005). Stilbenoids, including resveratrol and pterostilbene inhibit ANG2 by attenuation of ACE activity.

In particular aspects of the current disclosure, resveratrol is a preferred active ingredient in the disclosed formulations; however, in other embodiments, one or more alternative stilbenoid compounds (including, e.g., stilbenoid-rich nutraceuticals) may be substituted in place of resveratrol as an active ingredient in the exemplary formulations enumerated herein. Exemplary stilbenoids (and stilbenoid-rich nutraceuticals) include, without limitation, trans-pterostilbene, methylated resveratrol, bilberry extracts (including, without limitation, blueberry [*Vaccinium cyanococcus*] extract, cranberry [*Vaccinium oxycoccus*] extract, sparkleberry [*Vaccinium arboretum*] extract, and lingonberry [*Vaccinium vitis*] extract, or combinations thereof); grape extracts (including, without limitation, red wine polyphenolic compounds [e.g., Provinol]), and any combination thereof.

Essential Oils

Derived from the living elements of a plant, therapeutic essential oils contain thousands of bioactive compounds including terpenes, phenols, alkanes, alcohols, ethers, aldehydes, ketones, carboxylic acids, esters, furanoids, and the like. Many of these molecules have been shown to possess anti-inflammatory and/or anti-carcinogenic properties.

The Boswellic acids (BA) of Frankincense (olibanum; *Boswellia sacra, Boswellia serrata* and *Boswellia caterri*) have anti-inflammatory effects that are thought to occur through the suppression of PGE2 formation via interference with mPGES1. The key constituents of BA include monoterpenes (64-90%), sesquiterpenes (5-10%), alcohols (2-5%), and sesquiterpenols (0-1%). Boswellic acids have demonstrated an inhibitory effect on 5-lipoxygenase (5-LO) leading to a decrease in the production of leukotrienes. Many chronic inflammatory diseases such as rheumatoid arthritis, osteoarthritis, bronchial asthma, and Crohn's disease are associated with an increase in leukotrienes.

Boswellic acids interfere with COX-2, and may mediate their anti-inflammatory actions not only by the suppression of lipoxygenases, but also by inhibiting cyclooxygenases, preferentially COX-2. Boswellic acids prevent TNF-α induced expression of MMP, and target NF-κB signaling and the subsequent NFκB-dependent cytokine production to decrease inflammation. BAs also inhibit basic Fibroblast Growth Factor (bFGF), a metastatic growth factor known to promote tumor-induced angiogenesis.

Boswellic acids also inhibit IκK activity, and promote apoptosis in androgen-independent PC-3 prostate cancer. They have also been shown to produce anti-proliferative and apoptotic effects in human colon cancer HT-29 cells, and in liver cancer Hep G2 cells. The apoptotic effect of BA appears to be mediated via a pathway dependent on caspase-8 activation, but independent of FAS/FasL interaction. *Boswellia*, rosemary, and thyme essential oils control the renin-angiotensin system by down-regulation of ACE, which inhibits ANG-2.

The key constituents of rosemary essential oil (*Rosemarinus officinalis*) include ketones (16-50%), monoterpenes (22-45%), oxides (1-15%), esters (6-11%), alcohols (1-7%), carboxylic acids (1-2%), and sesquiterpenes (0-2%). Carnosol, a naturally occurring phyto-polyphenol found in rosemary essential oil, is a potent antioxidant that has been shown to suppress iNOS through down-regulating NF-κB in mouse macrophages. The inhibition of NF-κB is anti-inflammatory. Carnosol reduces metalloproteinase-9 (MMP-9) expression and activity by suppressing (ERK) AKT, p38 and JNK signaling pathway and inhibition of NFκB and AP-1 binding activity. Rosmarinic acid (RA), a natural phytophenolic carboxylic acid also found in Rosemary essential oil, exerts its anti-inflammatory effects through COX-2 inhibition. RA is an effective preventative agent against COX-2 activation by AP-1 inducing agents in both cancer and nonmalignant mammary epithelial cells. Both RA and carnosic acid (CA), a phenolic diterpene, show anti-proliferative effects in NCI-H82 (human, small cell lung, carcinoma), DU-145 (human, prostate, carcinoma), Hep-3B (human, black, liver, carcinoma, hepatocellular), K-562 (human chronic myeloid leukemia), MCF-7 (human, breast, adenocarcinoma), PC-3 (human, prostate, adenocarcinoma) and MDA-MB-231 (human, breast, adenocarcinoma) by MTT assay.

The key constituents of thyme essential oil (*Thymus vulgaris*) include phenols (38-60%), monoterpenes (21-54%), oxides (4-15%), alcohols (3-14%), sesquiterpenes (1-8%), and carboxylic acids (1-2%). Cymophenol (carvacrol; 5-isopropyl-2-methylphenol-2-methyl-5-(1-methylethyl)-phenol), a monoterpenoid phenol, is a major component of the suppressor of COX-2 expression and an activator of PPARα and PPARγ. In human macrophage-like U937 cells, carvacrol suppressed lipopolysaccharide-induced COX-2 mRNA and protein expression, suggesting that carvacrol regulates COX-2 expression through its agonistic effect on PPARγ.

The key constituents of turmeric essential oil (*Curcuma longa*) include the cyclic monoterpenes, α-phellandrene (α-2-methyl-5-(1-methylethyl)1,3-cyclohexadiene), terpinolene (δ-terpinene), eucalyptol (1,8-cineole), and the alkylbenzene, p-cymene (1-methyl-4-(1-methylethyl)benzene).

In certain aspects of the present disclosure, frankincense, rosemary, and thyme oils are preferred active ingredients in the disclosed formulations; however, in other embodiments, one or more alternative essential oils may be substituted in place of one or more of thyme, rosemary, and frankincense essential oil, as active ingredients in the exemplary formulations enumerated herein. Exemplary alternative essential oils include, without limitation, oregano, marjoram, birch, peppermint, wintergreen, clove, *eucalyptus*, vetiver, turmeric, and combinations thereof.

In particular aspects of the invention, one or more essential oils having a pleasing fragrance can be added to the compositions to provide a selected scent. Particularly beneficial essential oils for scenting agents include, but are not limited to, sweet orange oil, tangerine oil, grapefruit oil, and any combinations thereof.

The inventors also contemplate the addition of one or more essential oils having natural antimicrobial or antioxidant properties to prolong the shelf life of topical formulations, and to retard the growth of microbial contaminants. In this regard, clove oil has been found to impart particularly beneficial properties.

EXEMPLARY DEFINITIONS

Unless defined otherwise, all technical and scientific terms used herein have the same meaning as commonly understood by one of ordinary skill in the art to which this invention belongs. The following references provide one of skill with a general definition of many of the terms used in this invention: *Dictionary of Biochemistry and Molecular Biology*, ($2^{nd}$ Ed.) J. Stenesh (Ed.), Wiley-Interscience (1989); *Dictionary of Microbiology and Molecular Biology* ($3^{rd}$ Ed.), P. Singleton and D. Sainsbury (Eds.), Wiley-Interscience (2007); *Chambers Dictionary of Science and Technology* ($2^{nd}$ Ed.), P. Walker (Ed.), Chambers (2007); *Glossary of Genetics* ($5^{th}$ Ed.), R. Rieger et al. (Eds.), Springer-Verlag (1991); and *The HarperCollins Dictionary of Biology*, W. G. Hale and J. P. Margham, (Eds.), HarperCollins (1991).

Although any methods and compositions similar or equivalent to those described herein can be used in the practice or testing of the present invention, the preferred methods, and compositions are described herein. For purposes of the present invention, the following terms are defined below for sake of clarity and ease of reference:

In accordance with long standing patent law convention, the words "a" and "an," when used in this application, including the claims, denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "biological molecule" refers to any molecule found within a cell or produced by a living organism, including those obtained from plants, animals, or microorganisms such as bacteria, yeast, fungi, viruses and the like. A biological molecule may include, but is not limited to, one or more nucleic acids, proteins, peptides, carbohydrates, or lipids, as well as combinations or derivatives thereof. As used herein, a "cell" refers to the smallest structural unit of an organism that is capable of independent functioning and is comprised of cytoplasm and various organelles surrounded by a cell membrane. This may include, but is not limited to, cells that function independently such as bacteria and protists, or cells that live within a larger organism such as leukocytes and erythrocytes. As defined herein, a cell may not necessarily include a nucleus, such as, for example, a mature human red blood cell.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof that is pharmaceutically acceptable for administration to the relevant animal, as applicable. The use of one or more delivery vehicles for chemical compounds in general, and for the delivery of the anti-inflammatory orthomolecular formulations disclosed herein to mammals in particular, is well known to those of ordinary skill in the pharmaceutical and nutraceutical compounding arts.

The terms "for example" or "e.g.," as used herein, are used merely by way of example, without limitation intended, and should not be construed as referring only those items explicitly enumerated in the specification.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state.

As used herein, the term "kit" may be used to describe variations of the portable, self-contained enclosure that includes at least one set of reagents, components, or pharmaceutically-formulated compositions for use in one or more of the methods of the present disclosure. Optionally, such kit may include one or more sets of instructions for use of the enclosed reagents, such as, for example, in a laboratory or clinical application.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, ovines, porcines, ranines, racines, vulpines, and the like, including livestock, zoological specimens, exotics, as well as companion animals, pets, and any animal under the care of a veterinary practitioner. A patient can be of any age at which the patient is able to respond to inoculation with the present vaccine by generating an immune response. In particular embodiments, the mammalian patient is preferably human.

The phrase "pharmaceutically-acceptable" refers to molecular entities and compositions that preferably do not produce an allergic or similar untoward reaction when administered to a mammal, and in particular, when administered to a human.

As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

The term "subject," as used herein, describes an organism, including mammals such as primates, to which treatment with the compositions according to the present invention can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

As used herein, the term "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

As used herein, "synthetic" shall mean that the material is not of a human or animal origin.

The term "therapeutically-practical period" means the period of time that is necessary for one or more active agents to be therapeutically effective. The term "therapeutically-effective" refers to reduction in severity and/or frequency of one or more symptoms, elimination of one or more symptoms and/or underlying cause, prevention of the occurrence of symptoms and/or their underlying cause, and the improvement or a remediation of damage.

As used herein, the terms "treatment," "treat," "treated," or "treating" refer to therapy, or to the amelioration or the reduction, in the extent or severity of disease, or a symptom thereof, whether before or after its development afflicts a patient. When used with respect to an infectious disease, for example, the terms refer to a treatment protocol or regimen that decreases the severity of the infection or decreases or lessens or delays one or more symptoms of illness attributable to the infection, as well as increasing the ability of the infected individual to fight the infection, including e.g., the reduction and/or elimination of the infection from the body of the individual, or to lessen or prevent the disease from becoming worse.

"Treating" or "treatment of" as used herein, refers to providing any type of medical or surgical management to a subject. Treating can include, but is not limited to, administering a composition comprising a therapeutic agent to a subject. "Treating" includes any administration or application of a compound or composition of the invention to a subject for purposes such as curing, reversing, alleviating, reducing the severity of, inhibiting the progression of, or reducing the likelihood of a disease, disorder, or condition or one or more symptoms or manifestations of a disease, disorder, or condition. In certain aspects, the compositions of the present invention may also be administered prophylactically, i.e., before development of any symptom or manifestation of the condition, where such prophylaxis is warranted. Typically, in such cases, the subject will be one that has been diagnosed for being "at risk" of developing such a disease or disorder, either as a result of familial history, medical record, or the completion of one or more diagnostic or prognostic tests indicative of a propensity for subsequently developing such a disease or disorder.

The section headings used throughout are for organizational purposes only and are not to be construed as limiting the subject matter described. All documents, or portions of documents, cited in this application (including, but not limited to, patents, patent applications, articles, books, and treatises) are expressly incorporated herein in their entirety by express reference thereto. In the event that one or more of the incorporated literature and similar materials defines a term in a manner that contradicts the definition of that term in this application, this application controls.

EXAMPLES

The following examples are included to demonstrate illustrative embodiments of the invention. It should be appreciated by those of ordinary skill in the art that the techniques disclosed in the examples that follow represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

Formulation of Multi-Component Anti-Inflammatory Compositions

This example provides four, successively developed, formulations that include one or more of the various classes of orthomolecular reagents as described herein. Table 1 summarizes the components of each of these specific formulations.

TABLE 1

| Ingredient | Formula 1 | Formula 2 | Formula 3 | Formula 4 |
|---|---|---|---|---|
| Water | | | | |
| Isopropyl palmitate | | | | |
| Isopropyl myristate | | | | |
| Lipowax D (cetearyl alcohol and ceteareth-20) | | | | |
| Tetrahydrocurcumins (60/39/10 tetrahydrocurcumin/tetrahydrocurcumins/tetrahydropiperine) (as curcuminoid CG powder) | | | | 20 g |
| α-Lipoic acid DL alpha (thioctic acid) | 5 g | 0.15 g | 5 g | 5 g |
| Keltrol CG (xanthan gum) | | | | |
| Lipoderm-core (PCCA Lipoderm) | 900 g | 27 g | 800 g | 535 g |
| *Wasabia japonica* (i-Sabi ™) powder | | | | 20 g |
| Broccoli seed oil with conc. sulforaphane 104 mg. | 40 mL | 1.2 mL | 40 mL | 40 mL |
| Melatonin | | | | |
| Pharmasolve NPM (N-methyl pyrrolidone) | | | | |
| Vitamin D$_3$ | 26 mL | 0.78 mL | 26 mL | 26 mL |
| Vitamin E (tocopherol acetate) | | 0.15 mL | 5 mL | 5 mL |
| 3'3'-diindolylmethane (DIM) powder | | | | 2 g |
| Resveratrol (3,5,4'-trihydroxy-trans-stilbene) | 20 g | 0.6 g | 20 g | 20 g |
| Frankincense scara Essential Oil | | | | |
| Rosemary water-soluble Essential Oil | | | 33 mL | 33.3 mL |
| Sweet orange Essential Oil | 15 drops | 0.45 drop | 15 drops | 15 drops |
| Frankincense water-soluble Essential Oil | | | | 33.3 mL |
| Thyme water-soluble Essential Oil | | | | 33.3 mL |
| Clove Essential Oil | | | | |
| Optiphen Plus (phenoxyethanol, caprylyl glycol and sorbic acid) | | | | |
| EGC-GINE (as green tea) | 20 g | 0.6 g | 20 g | 20 g |
| Sepigel 305 (polyacrylamide based emulsion/rheology modifier) | | | | |
| Propylene glycol | 25 mL | 0.75 mL | 25 mL | 25 mL |
| Dimethylsulfoxide (DMSO) | 25 mL | 0.75 mL | 25 mL | 100 mL |
| Menadione USP (K-3) powder (Vitamin K-3) | 0.3 g | 0.009 g | 0.3 g | 0.3 g |

TABLE 1-continued

| Ingredient | Formula 1 | Formula 2 | Formula 3 | Formula 4 |
|---|---|---|---|---|
| Poloxamer 407 NF granules (pluronic F-127 NF) (block copolymer of ethylene oxide and propylene oxide) | 100 g | 3 g | 100 g | 150 g |
| Carcinosin 30 C solution | | 0.999 mL | 33.3 mL | 33.3 mL |
| Poke root oil (*Phytolaccca americana*/olive/vitamin E oil) | | 0.4995 mL | 16.65 mL | 16.65 mL |
| Butylated hydroxytoluene | | 4 g | | |

Other optional ingredients that have been prepared and tested in the disclosed topical compositions include wintercress seed powder (0.3%), radish seed powder (0.3%), watercress seed powder (0.3%), watercress seed oil (2%), and wintercress seed oil (2%).

Example 2

Second- and Third-Generation Anti-Inflammatory Compositions

This example provides a component-by-component analysis of a second-generation formulation developed by the inventors that demonstrated particularly surprising and unexpected results in the practice of one embodiment of the present invention. Table 2 summarizes the active and inactive ingredients contained with specific formulation developed.

An exemplary, third-generation formulation has also been prepared that further includes (in addition to each of the components listed in Table 2), wintercress seed powder and wintercress seed oil (at final concentrations of 0.3% and 2%, respectively).

TABLE 2

AN EXEMPLARY 2ND-GENERATION ORTHOMOLECULAR FORMULATION

| Ingredient | % (wt./wt.) | Family |
|---|---|---|
| PHASE A | | |
| Water | 60 | |
| PHASE B | | |
| Isopropyl palmitate | 3 | |
| Isopropyl myristate | 3 | |
| Lipowax D (cetearyl alcohol and ceteareth-20) | 5 | |
| SabiWhite ™ (tetrahydrocurcumin from *Curcuma longa*) | 0.25 | Curcuminoids |
| Tetrahydrocurcuminoids CG ™ (standardized power from *Curcuma longa*) containing: Tetrahydrodiferuloylmethane Tetrahydrodemethoxydiferuloylmethane Tetrahydrobisdemethoxydiferuloylmethane | 0.25 | Curcuminoids |
| Cosmoperine ® (tetrahydropiperine from black pepper) | 0.05 | Curcuminoids |
| DL-α-Lipoic Acid | 0.15 | |
| Keltrol CG (xanthan gum) | 0.1 | |
| (R)-Sulforaphane (200 mg in 87 mL) in cyclodextrin | 0.24 | Isothiocyanate |
| PHASE C | | |
| Transdermal Compounding Base† (PCCA Lipoderm ®) | 8 | |
| Tetrahydrodiferuloylmethane (i-Sabi ™, *W. japonica* powder) | 2 | Isothiocyanate |
| Broccoli seed oil with SGS (from *Brassica oleracea*) | 5.4 | |
| Mustard seed oil (from *Sinapis juncea*) | 0.2 | |
| Broccoli seed powder (from *Brassica oleracea*) | 0.3 | Isothiocyanate |
| Melatonin | 0.1 | |
| N-Methyl-2-pyrrolidone (NMP; Pharmasolve ®) | 2.5 | |
| Cholecalciferol (Vitamin $D_3$) | 1.5 | |
| α-Tocopherol acetate (Vitamin E) | 1 | |
| 3'3-Diindolylmethane (DIM) | 0.4 | |
| 3,5,4'-Trihydroxy-trans-stilbene (Resveratrol) | 1.2 | Stilbenoids |
| 4-[(E)-2-(3,5-Dimethoxyphenyl)ethenyl]phenol (pterostilbene) | 0.8 | Stilbenoids |
| PHASE D | | |
| *Boswellia serrata* essential oil (5 drops in 87 mL) | 0.3 | Essential Oil |
| *Boswellia carterii* essential oil (5 drops in 87 mL) | 0.3 | Essential Oil |
| Rosemary essential oil (8 drops in 87 mL) | 0.5 | Essential Oil |
| Sweet orange essential oil (absolute) | 0.6 | Essential Oil |
| Thyme essential oil (10 drops in 87mL) | 0.6 | Essential Oil |
| Clove essential oil (5 drops in 87 mL) | 0.3 | Essential Oil |
| Turmeric essential oil (1 drop in 87 mL) | 0.05 | Essential Oil |

TABLE 2-continued

AN EXEMPLARY 2ND-GENERATION ORTHOMOLECULAR FORMULATION

| Ingredient | % (wt./wt.) | Family |
|---|---|---|
| Optiphen ® Plus (phenoxyethanol, caprylyl glycol and sorbic acid) | 1.25 | |
| Epigallocatechin gallatyl glucoside (EGC-GINE as green tea) | 0.1 | Catechin |
| PHASE E | | |
| Sepigel 305 (polyacrylamide based emulsion/rheology modifier) | 1 | |
| TOTAL | ~100 | |

†Transdermal Compounding Base (Lipoderm Core) Ingredients: *Pentaclethra macroloba* (Pracaxi seed) oil; *Plukenetia volubilis* (Sacha peanut) oil; Phosphatidylcholine; *Carthamus tinctorius* (Safflower) seed oil; Hydrogenated lecithin; *Butyrospermum parkii* (Shea) Butter; Caprylic/Capric triglyceride; Water; Alcohol; Glyceryl stearate; *Cocos nucifera* (Coconut) essential oil; Squalane; Ceramide 3; Ascorbyl palmitate; and Potassium sorbate.

Example 3

Exemplary Procedure for Formulating Topical Creams

This example describes one exemplary procedure for formulating a topical cream (FIG. 6A and FIG. 6B) that comprises an orthomolecular formulation in accordance with one embodiment of the present disclosure:

(1) Combine ingredients of PHASE A, and heat to ~75° C.-80° C. with mixing; (2) In a separate vessel, combine ingredients of PHASE B, and heat to ~75° C.-80° C. with mixing; (3) In a separate vessel, combine ingredients of PHASE C, and mix using a mixing propeller. Heat to ~60° C. with mixing; (4) In a separate vessel, combine ingredients of PHASE D and mix well until solubilized; (5) When "PHASE A" and "PHASE B" each reach a temperature of ~75° C.-80° C., add PHASE A to PHASE B, and homogenize for 2 min at 2,000 rpm; (6) Using a mixing propeller, mix and maintain temperature for 10 min; (7) Begin cooling mixture, and continue mixing at moderate speed; (8) At ~60° C., add PHASE C, and continue mixing; (9) At ~35° C., add PHASE D, and continue mixing; (10) At ~32° C., add PHASE E (cyclodextrin sulforaphane), and cool to desired fill temperature; (11) Add DMSO to curcuminoid CG powder and blend until a smooth solution is achieved. Then add frankincense, pokeroot oil, rosemary, thyme, Inflamyar ointment, Carcinosin 30C, vitamin $D_3$; add Lipoderm® core, then mix again. Run resulting material through ointment mill on level #1, and then mix again. Dispense in suitable container (e.g., Topi-Click® dispensers) and label. A modification of this method may also be employed: when adding Carcinosin 30C and vitamin $D_3$ (0.5 mL/30 g), Inflamyar and curcuminoid may be decreased by up to 50% (e.g., Inflamyar may be decreased to 1 g/30 g, and curcumin may be decreased to 2 g/30 g).

Example 4

Thermography Study of Human Breast Tissue

Thermograms consist of digital infrared imaging that produces high resolution pictures of temperature variations found in tissue. Increases in temperatures denoted by the color "red" indicate potential issues such as inflammation-induced excessive/atypical blood flow; tissue damage; increased cell metabolism; and hormone imbalances. Each of these biologic processes acts to increase the entropy residing within the ECM. A stable physiologic microenvironment has a higher ordered state that translates into lower entropy. Thermograms therefore provide a functional assessment of the human tissues, such as breast tissue for example, including a quantitative measurement of those events that disrupt the ECM. Pro-angiogenic and pro-inflammatory pathways, studied by other in vivo models, can be measured in the form of pixels. The effectiveness of an exemplary transdermal orthomolecular formulation in accordance with one aspect of the present invention to stabilize the ECM of human breast tissue was measured using breast thermography. The following protocol was used, and the results are summarized below.

Test Subjects:

Test subjects were selected from an existing patient base, as well as their friends and friends of staff. Six patients completed the two-thermogram study using breast cream Formulation #1. Of these, one patient was excluded from the results, as she had received a deep-tissue massage the day before her final thermogram. A total of 66 patients completed the two-thermogram study, with each using one of three exemplary orthomolecular anti-inflammatory topical formulations (Formulations #2, #3, or #4 in Table 1).

Of these, three patients were excluded from the results, because of failure to continue application of the cream as directed for the full study period. Data was collected on age, height, weight, BMI, cup size, hormones taken (if any) and pre- or post-menopausal symptoms. The age range of the participants was between 36 and 68 with a median age of 52 (approximately 50% of the individuals were pre- and approximately 50% post-menopausal.

Imaging Protocol:

The following procedure was followed using a Spectron IR Medical Infrared Imaging System with the following instrument parameters: Detector: 640×480 VOx Focal Plane Array; Radiometric Microbolometer; Spectral Band: 8-12 microns; Frame Rate: 30 Hz; Spatial Resolution: 0.50 mrad; Sensitivity: Less than 50 mK average; Computer Interface: Digital (Firewire); Focusing Distance: 12 inches to 15 feet; and Software Controlled Electronic Focus.

Thermograms were only scheduled in the morning hours to avoid afternoon heat, and the examination room thermostat was set to 70° F. The room had at most one low-wattage incandescent bulb, and overhead florescent lighting. There was a fixed distance between the camera and the patients. An instruction sheet was given to patients, and an initial thermographic image was recorded. The patients sat in the room disrobed from the waist up with their arms away from their bodies for a minimum of 20 min. Images were taken of the upper torso from the Oblique Right View, Oblique Left View and Full Frontal View. A 90-day supply of cream was provided; for women with larger breasts, additional cream was provided as necessary. A follow-up thermogram was recorded after 90-days' usage of the topical orthomolecular cream formulation.

Data Analysis:

The following data was collected from the initial and 90-day follow-up thermograms: An oval was drawn on the initial thermal image encompassing 70-75% of the overall breast area. The same size oval +/−3% was drawn over the same area on post-90-day thermogram. A software tool was incorporated to duplicate the oval—it had to be hand positioned. Within these ovals on the initial thermogram and the follow up thermogram, the average temperature and standard deviation were measured. Minimum and maximum temperature of the entire torso image was also recorded. From these measurements, the overall temperature range of the torso was calculated, as was the change in the lower-end reading of the overall torso between initial thermogram and follow up thermogram, the change in the upper-end reading of the overall torso between initial thermogram and follow-up thermogram, the number of days between thermograms, the change in average temperature of the sample ovals (in ° C., and as a percentage between initial and. follow-up thermograms), and the change in standard deviation (as a number, and as a percentage between initial and. follow-up thermograms).

Results:

Using Formulation #1 of the disclosed topical breast cream composition, an average temperature reduction of 0.62° C. (~2%) was observed by thermography in patients that were administered a 1-cc daily dose of the topical formulation for a total of 90 days. Using Formulations #2, #3, and #4 (see Table 1) of the disclosed topical breast cream compositions, an average temperature reduction of 0.94° C. (~3%) was observed by thermography in patients that were administered a 1-cc daily dose of one of the topical formulations for a total of 90 days. The results (summarized in Table 3A and Table 3B) demonstrated an average overall reduction in breast temperature of 0.6° C. for the sample patient population. Individual breast thermograms pre-treatment (d0) and post-treatment (d90) showed marked reduction in both the number and size of blood vessels in the breast tissue (FIG. 1, FIG. 2A, FIG. 2B, FIG. 3, FIG. 4, and FIG. 5).

TABLE 3A

INITIAL THERMOGRAM (DAY 0)

| Avg. Temp. of Oval (° C.) | Standard Deviation | Dimensions of Sample Oval | Temperature Range (° C.) | | Patient ID No. |
|---|---|---|---|---|---|
| 30.07 | ±0.78 | 192 × 224 | 28.32 | 35.55 | 1 |
| 29.83 | ±0.53 | 207 × 208 | 27.57 | 32.02 | 2 |
| 30.71 | ±1.11 | 243 × 250 | 25.82 | 34.81 | 3 |
| 29.3 | ±0.74 | 188 × 213 | 27.47 | 35.11 | 4 |
| 27.50 | ±1.04 | 258 × 256 | 24.45 | 31.79 | 5 |
| 33.35 | ±1.31 | 275 × 249 | 28.58 | 38.62 | 6 |
| 28.57 | ±0.63 | 214 × 254 | 26.92 | 34.56 | 7 |
| 28.23 | ±0.72 | 245 × 223 | 25.82 | 34.81 | 8 |
| 28.53 | ±0.63 | 181 × 210 | 26.71 | 34.05 | 9 |
| 29.11 | ±0.85 | 184 × 185 | 26.06 | 33.99 | 10 |
| 29.22 | ±1.03 | 301 × 285 | 25.61 | 32.95 | 11 |
| 29.72 | ±0.65 | 253 × 230 | 26.00 | 34.00 | 12 |
| 29.43 | ±0.61 | 240 × 297 | 23.90 | 35.14 | 13 |
| 29.70 | ±0.95 | 255 × 246 | 26.02 | 33.66 | 14 |
| 29.59 | ±0.85 | 266 × 257 | 25.77 | 34.11 | 15 |
| 30.95 | ±0.80 | 247 × 240 | 25.06 | 35.37 | 16 |
| 30.80 | ±0.55 | 235 × 232 | 26.00 | 33.18 | 17 |
| 28.25 | ±0.53 | 220 × 199 | 26.00 | 33.9 | 18 |
| 28.34 | ±0.75 | 214 × 193 | 25.81 | 33.15 | 19 |
| 28.56 | ±0.75 | 275 × 236 | 25.91 | 33.25 | 20 |
| 27.80 | ±0.67 | 237 × 173 | 26.47 | 33.80 | 21 |
| 29.55 | ±0.80 | 258 × 165 | 25.82 | 34.81 | 22 |
| 31.25 | ±0.64 | 257 × 215 | 26.45 | 35.93 | 23 |
| 30.56 | ±0.65 | 211 × 197 | 26.47 | 35.46 | 24 |
| 28.09 | ±0.64 | 260 × 193 | 26.61 | 33.51 | 25 |
| 31.06 | ±0.95 | 203 × 165 | 26.15 | 37.39 | 26 |
| 25.51 | ±0.52 | 227 × 219 | 24.80 | 31.33 | 27 |
| 30.33 | ±0.52 | 225 × 159 | 27.62 | 34.95 | 28 |
| 28.16 | ±0.59 | 215 × 181 | 23.89 | 32.93 | 29 |
| 28.57 | ±0.88 | 280 × 215 | 25.10 | 33.44 | 30 |
| 28.01 | ±0.69 | 254 × 191 | 24.96 | 31.86 | 31 |
| 27.47 | ±1.08 | 252 × 184 | 26.10 | 33.06 | 32 |
| 30.62 | ±0.48 | 125 × 97 | 26.60 | 33.94 | 33 |
| 30.22 | ±0.64 | 199 × 198 | 27.62 | 34.96 | 34 |
| 29.91 | ±0.67 | 228 × 179 | 26.50 | 34.24 | 35 |
| 29.47 | ±0.58 | 195 × 176 | 25.90 | 34.82 | 36 |
| 31.07 | ±0.73 | 123 × 103 | 28.63 | 35.96 | 37 |
| 27.74 | ±0.76 | 179 × 166 | 24.79 | 33.70 | 38 |
| 29.89 | ±0.79 | 314 × 238 | 25.85 | 33.19 | 39 |
| 30.51 | ±0.66 | 174 × 164 | 26.00 | 33.99 | 40 |
| 29.59 | ±0.68 | 173 × 135 | 26.41 | 34.05 | 41 |
| 28.53 | ±1.20 | 253 × 215 | 26.01 | 32.87 | 42 |
| 29.15 | ±1.03 | 204 × 184 | 23.36 | 34.09 | 43 |
| 31.75 | ±0.88 | 218 × 213 | 28.32 | 35.65 | 44 |
| 28.40 | ±0.75 | 125 × 126 | 26.36 | 33.75 | 45 |
| 28.59 | ±0.66 | 174 × 178 | 25.92 | 33.25 | 46 |
| 27.82 | ±0.62 | 219 × 187 | 25.66 | 33.30 | 47 |
| 29.39 | ±1.01 | 196 × 195 | 27.32 | 34.66 | 48 |
| 26.84 | ±0.76 | 223 × 203 | 25.21 | 32.55 | 49 |
| 27.79 | ±0.64 | 260 × 226 | 25.22 | 32.61 | 50 |
| 29.99 | ±0.63 | 175 × 161 | 28.73 | 36.07 | 51 |
| 27.71 | ±0.48 | 239 × 245 | 25.91 | 33.25 | 52 |
| 30.44 | ±0.68 | 192 × 175 | 25.60 | 35.64 | 53 |
| 30.47 | ±1.04 | 194 × 155 | 24.90 | 32.89 | 54 |
| 30.39 | ±0.68 | 156 × 149 | 27.57 | 34.91 | 55 |
| 29.95 | ±0.34 | 165 × 139 | 25.81 | 34.80 | 56 |
| 29.35 | ±0.65 | 239 × 206 | 24.67 | 34.27 | 57 |
| 30.61 | ±0.67 | 226 × 218 | 25.60 | 32.94 | 58 |
| 30.64 | ±1.05 | 217 × 215 | 25.45 | 34.36 | 59 |
| 28.26 | ±0.94 | 242 × 229 | 25.82 | 34.81 | 60 |
| 30.13 | ±1.13 | 245 × 260 | 26.77 | 34.11 | 61 |
| 27.04 | ±1.10 | 243 × 244 | 23.25 | 33.10 | 62 |
| 28.31 | ±1.02 | 247 × 256 | 24.80 | 32.14 | 63 |
| 30.37 | ±0.80 | 228 × 227 | 26.46 | 33.80 | 64 |
| 30.29 | ±0.82 | 267 × 287 | 27.22 | 34.61 | 65 |
| 29.26 | ±0.62 | 220 × 227 | 25.76 | 33.10 | 66 |
| 29.75 | ±0.94 | 179 × 184 | 28.43 | 35.70 | 67 |
| 26.68 | ±0.92 | 260 × 256 | 23.50 | 30.84 | 68 |
| 29.65 | ±1.14 | 247 × 213 | 27.16 | 33.24 | 69 |
| 30.53 | ±0.88 | 205 × 205 | 26.52 | 33.86 | 70 |
| 32.53 | ±0.82 | 232 × 278 | 28.17 | 37.27 | 71 |

TABLE 3B

FINAL THERMOGRAM (DAY 90)

| Avg. Temp. of Oval (° C.) | Standard Deviation | Dimensions of Sample Oval | Temperature Range (° C.) | | Patient ID No. |
|---|---|---|---|---|---|
| 30.85 | ±0.76 | 192 × 224 | 28.28 | 35.62 | 1 |
| 29.57 | ±0.54 | 207 × 208 | 27.56 | 31.99 | 2 |
| 25.53 | ±1.43 | 243 × 260 | 22.08 | 29.42 | 3 |
| 30.45 | ±0.98 | 188 × 213 | 27.45 | 35.10 | 4 |
| 27.66 | ±1.25 | 254 × 257 | 24.41 | 31.75 | 5 |
| 30.57 | ±1.12 | 284 × 277 | 27.37 | 35.41 | 6 |
| 27.29 | ±0.61 | 257 × 263 | 25.66 | 33.00 | 7 |
| 24.97 | ±0.71 | 273 × 235 | 22.29 | 29.63 | 8 |
| 26.58 | ±0.81 | 205 × 206 | 24.95 | 32.29 | 9 |
| 28.47 | ±0.64 | 184 × 186 | 25.05 | 33.97 | 10 |

TABLE 3B-continued

FINAL THERMOGRAM (DAY 90)

| Avg. Temp. of Oval (° C.) | Standard Deviation | Dimensions of Sample Oval | Temperature Range (° C.) | | Patient ID No. |
|---|---|---|---|---|---|
| 28.48 | ±1.09 | 269 × 262 | 24.91 | 32.25 | 11 |
| 30.54 | ±0.64 | 243 × 178 | 26.02 | 33.96 | 12 |
| 30.43 | ±0.77 | 236 × 240 | 28.33 | 35.67 | 13 |
| 30.79 | ±1.05 | 244 × 235 | 26.37 | 34.01 | 14 |
| 28.7 | ±1.08 | 294 × 282 | 25.66 | 34.00 | 15 |
| 31.53 | ±0.75 | 213 × 238 | 25.02 | 35.37 | 16 |
| 25.03 | ±0.65 | 242 × 213 | 23.24 | 31.23 | 17 |
| 28.89 | ±0.51 | 220 × 199 | 26.07 | 33.06 | 18 |
| 26.5 | ±0.85 | 214 × 193 | 23.65 | 32.24 | 19 |
| 27.98 | ±0.59 | 237 × 183 | 26.20 | 33.54 | 20 |
| 28.27 | ±0.72 | 256 × 210 | 26.47 | 33.81 | 21 |
| 25.24 | ±0.72 | 257 × 223 | 23.49 | 32.49 | 22 |
| 30.74 | ±0.75 | 168 × 161 | 26.62 | 33.95 | 23 |
| 27.2 | ±0.59 | 272 × 190 | 23.70 | 31.04 | 24 |
| 29.46 | ±0.94 | 272 × 190 | 26.58 | 33.92 | 25 |
| 29.33 | ±0.62 | 184 × 185 | 27.22 | 33.04 | 26 |
| 24.15 | ±0.63 | 239 × 218 | 21.79 | 29.59 | 27 |
| 30.1 | ±0.65 | 222 × 164 | 27.62 | 34.96 | 28 |
| 28.49 | ±0.82 | 256 × 199 | 23.85 | 34.59 | 29 |
| 28.39 | ±0.88 | 243 × 208 | 25.02 | 33.36 | 30 |
| 27.9 | ±0.78 | 245 × 202 | 25.41 | 33.30 | 31 |
| 27.47 | ±1.04 | 249 × 194 | 24.90 | 33.30 | 32 |
| 29.17 | ±0.57 | 217 × 219 | 24.75 | 33.75 | 33 |
| 29.55 | ±0.69 | 184 × 182 | 27.58 | 34.92 | 34 |
| 25.45 | ±0.72 | 224 × 169 | 24.06 | 28.24 | 35 |
| 29.1 | ±0.63 | 202 × 186 | 25.87 | 34.54 | 36 |
| 30.55 | ±0.87 | 221 × 223 | 26.62 | 35.97 | 37 |
| 30.33 | ±0.93 | 139 × 136 | 26.72 | 33.73 | 38 |
| 28.71 | ±0.89 | 258 × 200 | 26.32 | 33.91 | 39 |
| 29.17 | ±0.75 | 174 × 164 | 25.02 | 34.01 | 40 |
| 29.33 | ±0.88 | 206 × 140 | 26.37 | 34.01 | 41 |
| 28.78 | ±1.13 | 244 × 200 | 25.81 | 34.86 | 42 |
| 29.92 | ±0.89 | 260 × 221 | 25.82 | 34.81 | 43 |
| 29.59 | ±0.71 | 255 × 227 | 28.28 | 35.62 | 44 |
| 28.59 | ±0.88 | 211 × 185 | 25.36 | 35.18 | 45 |
| 30.16 | ±0.63 | 196 × 194 | 25.91 | 33.25 | 46 |
| 26.83 | ±0.49 | 188 × 174 | 25.3 | 32.64 | 47 |
| 27.44 | ±0.82 | 157 × 154 | 26.47 | 33.81 | 48 |
| 28.52 | ±0.70 | 209 × 181 | 25.21 | 32.55 | 49 |
| 27.47 | ±0.64 | 236 × 192 | 25.25 | 33.59 | 50 |
| 31.05 | ±0.88 | 204 × 191 | 28.68 | 35.02 | 51 |
| 26.22 | ±0.55 | 165 × 207 | 22.94 | 30.28 | 52 |
| 28.62 | ±0.82 | 179 × 189 | 25.2 | 33.54 | 53 |
| 30.98 | ±1.05 | 214 × 165 | 28.33 | 35.67 | 54 |
| 27.63 | ±0.53 | 180 × 167 | 25.07 | 33.41 | 55 |
| 25.64 | ±0.44 | 161 × 136 | 24.04 | 31.38 | 56 |
| 29.33 | ±0.64 | 223 × 205 | 25.9 | 33.24 | 57 |
| 27.89 | ±0.63 | 196 × 173 | 24.6 | 31.94 | 58 |
| 29.24 | ±0.93 | 221 × 214 | 25.41 | 32.75 | 59 |
| 26.96 | ±1.03 | 242 × 229 | 23.35 | 32.01 | 60 |
| 27.24 | ±0.92 | 245 × 260 | 24.56 | 31.95 | 61 |
| 30.24 | ±0.83 | 196 × 213 | 26.61 | 33.13 | 62 |
| 29.78 | ±0.65 | 283 × 270 | 25.51 | 33.50 | 63 |
| 32.81 | ±0.85 | 244 × 250 | 27.47 | 35.87 | 64 |
| 29.25 | ±0.75 | 267 × 287 | 27.33 | 34.71 | 65 |
| 30.95 | ±0.75 | 263 × 264 | 25.31 | 33.11 | 66 |
| 29.37 | ±0.82 | 282 × 205 | 25.86 | 35.73 | 67 |
| 28.17 | ±0.85 | 179 × 138 | 27.03 | 34.36 | 68 |
| 29.63 | ±1.14 | 250 × 240 | 25.91 | 33.25 | 69 |
| 30.09 | ±0.74 | 277 × 244 | 26.52 | 33.85 | 70 |
| 28.59 | ±0.85 | 217 × 280 | 25.22 | 33.56 | 71 |

Figure 7:
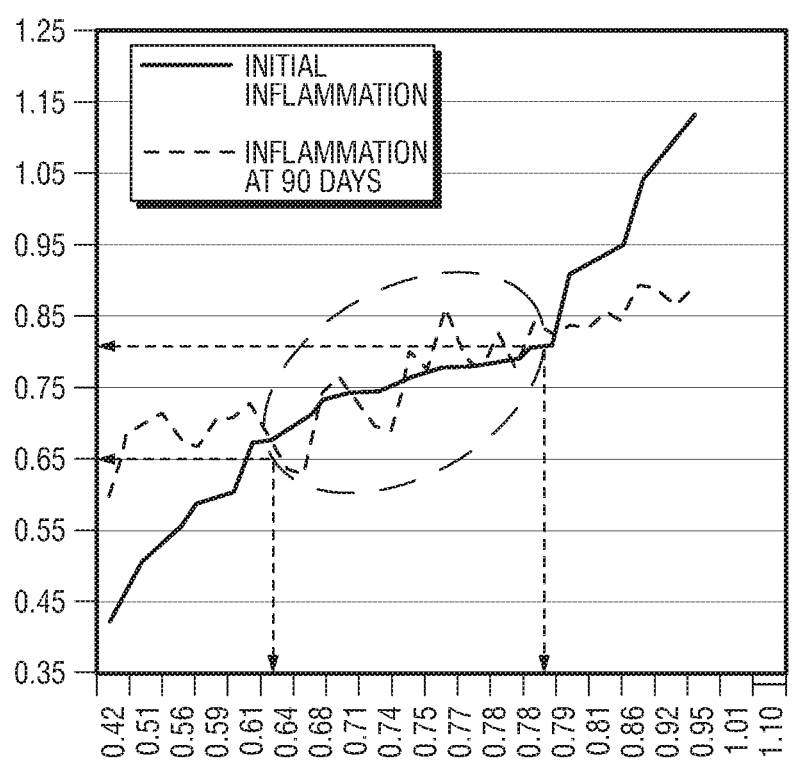
FIG. 7 shows exemplary results obtained from a human patient study involving application of the topical formulation of the disclosed orthomolecular compositions to both breasts once-daily for 90 consecutive days.

FIG. 7 denotes breast temperature range ratio "y axis" in relation to breast temperature standard deviation. The dotted line reflects the functional status of the breast matrix prior to cream application, while the dashed line reflects the matrix after cream application. One-third of the human patients exhibited elevated thermal matrix activity, compared to two-thirds of the study group. After application of the topical orthomolecular formulation, all breast tissue exhibited a significant decline in thermal readings. Approximately one-third of the test subjects exhibited temperature readings in the middle percentile range prior to topical formulation application. The thermal matrix activity revealed little significant change post application of the topical formulation.

Prior to topical formulation application, approximately one-third of test subjects exhibited a lower thermal matrix reading (lower left quadrant of FIG. 7) compared to the other two-thirds. After topical formula application, the thermal readings increased. Following cream application, a defined thermal activity range was noted for all test subjects indicating that the breast matrix reaches a steady state for optimum functioning.

An explanation for those test subjects with an initial lowered thermal reading can be found invoking the second law of thermodynamics. When applied to a biologic system the second law indicates that low entropic matrix states reflect nonfunctional fibrous tissue. This lack of proper function results in the tissue being unable to perform necessary physiologic duties. In the case of the breast matrix, an example would be a fibrotic low entropic tissue, which would have difficulty producing milk.

The adaptogenic qualities of the topical formulation with resolution of lowered biologic entropy are reflected by the increase in blood flow or thermal signature. The increase in tissue vasodilation was confirmed in the murine ear edema model. The control (non-oxazolone challenged), as well as the oxazolone-stimulated ears of the study animals, were noted to be erythematous but not edematous post-application of the cream.

FIG. 7 shows is a graphic representation of the thermal stabilization of the breast matrix using the topical disclosed compositions formulation.

Example 5

Evaluation of Anti-Inflammatory Activity in a Murine Model

The present example assesses the anti-inflammatory activity of a topically applied formulation in accordance with one aspect of the present invention in a prophylactic and therapeutic model of ear edema in BALB/c mice.

Materials:

Prior to testing, a third-party laboratory verified the levels of isothiocyanates in the topical formulation using HPLC (Table 4). All other ingredients consisted of 98% concentrates or specified concentration by manufacture.

TABLE 4

| Analyte | Result (mg/g) |
|---|---|
| 6-HITC | 3.014 |
| Sulforaphane | 2.649 |
| Sulforaphene | 1.803 |

Experimental Protocol:

5% oxazolone was prepared by adding 1 g of 4-ethoxymethylene-2-phenyl-2-oxazolin-5-one (oxazolone, Sigma, Cat. E0753, lot 0343753, St. Louis, Mo., USA) to 20 mL acetone (Acros Organics, Cat. 42324-0010, lot B4522107, Thermo Fisher Scientific, Princeton, N.J., USA). The mixture was gently heated until a bright yellow color.

52 BALB/c mice (Harlan Sprague-Dawley, Inc., Indianapolis, Ind., USA, male, 6-7 weeks old) were received, individually examined and housed in six cages of eight mice each and one cage containing four mice. No clinical signs of disease or distress were observed. The mice were placed in quarantine with daily inspections.

Day 0:

Mice were shaved on the abdomen and 100 μL of 5% oxazolone was applied to the area. The mice were returned to routine maintenance. 3% oxazolone was prepared by adding 0.3 g of oxazolone to 10 mL acetone. The mixture was gently heated until a bright yellow color.

TABLE 5

COMPOSITION OF EXEMPLARY TOPICAL FORMULATION

| Ingredients | % (wt./wt.) |
|---|---|
| PHASE A | |
| Water | 60 |
| PHASE B | |
| Isopropyl palmitate | 3 |
| Isopropyl myristate | 3 |
| Cetearyl alcohol/ceteareth-20 (Lipowax ® D, Lipo Chem., Patterson, NJ) | 5 |
| Tetrahydrocurcumin (SabiWhite ®) | 0.25 |
| Tetrahydrocurcuminoids CG (Sabinsa Corp., Piscataway, NJ) | 0.25 |
| Tetrahydropiperine (Cosmoperine ®, Sabinsa Corp.) | 0.05 |
| DL-α-Lipoic acid | 0.15 |
| Keitrol CG (xanthan gum) | 0.1 |
| Sulforaphane (200 mg in 87 mL) in cyclodextrin | 0.24 |
| PHASE C | |
| Lipoderm ® Transdermal Base* | 8 |
| Tetrahydroferulolyl-methane (I SABI) | 2 |
| Broccoli seed oil with SGS | 5.4 |
| Mustard seed oil | 0.2 |
| Broccoli seed powder | 0.3 |
| Melatonin | 0.1 |
| Pharmasolve ® NPM (N-methyl-2-pyrrolidone) | 2.5 |
| Vitamin $D_3$ (liquid) | 1.5 |
| Vitamin E (tocopherol acetate) | 1 |
| 3'3-Diindolylmethane (DIM) powder | 0.4 |
| Resveratrol (3,5,4'-trihydroxy-trans-stillbene) | 1.2 |
| Pterostillbene (4(E)-2(3,5-dimethoxyphenyl)ethenyl)phenol) | 0.8 |
| PHASE D | |
| Frankincense *Boswellia serrata* essential oil (5 drops in 87 mL) | 0.3 |
| Frankincense *Boswellia carterii* essential oil (5 drops in 87 mL)) | 0.3 |
| Rosemary essential oil (8 drops in 87 mL) | 0.5 |
| Sweet orange essential oil (XX drops in 87 mL) | 0.6 |
| Turmeric essential oil (1 drop in 87 mL) | 0.05 |
| Optiphen Plus (phenoxyethanol, caprylyl glycol and sorbic acid) | 1.25 |
| Epigallocatechin gallate glucosides (EGC-Gine as green tea) | 0.4 |
| PHASE E | |
| Sepigel 305 (polyacrylamide based emulsion and rheology modifier) | 1 |
| TOTAL | ~100 |

*Lipoderm ® Base (PCCA, Houston, TX, USA) ingredients: *Pentaclethra macroloba* Seed Oil, *Plukenetia volubilis* Seed Oil, Phosphatidylcholine, *Chartamus tinctorius* (Safflower) Seed Oil, Hydrogenated Lecithin, *Butyrospermum parkii* (Shea) Butter, Caprylic/capric triglyceride, Water, Alcohol, Glyceryl stearate, *Cocos nucifera* (Coconut) Oil, Squalane, Ceramide 3, Ascorbyl palmitate; and Potassium sorbate.

Day 6:

A separate group (3) of eight mice was topically treated with 25 μL of well-mixed Matrix Cream (13.44 mg active ingredients/cc) preparation on both sides of both ears (~12 hours). This equated to 0.336 mg of cream per ear.

0.6 mg betamethasone-21-valerate (Sigma Chem., Cat. B0515, lot 044K0995, salt factor=1.214) was dissolved in 12.4 mL acetone to prepare a 40 μg/mL solution for Group 2. 5 mg celecoxib (Sigma, Cat. PZ0008, lot 020M47044) was suspended in 5 mL $dH_2O$ (1 mg/mL) for Group 4.

Day 7:

The mice in Group 3 were topically treated with 25 μL of well-mixed Matrix Topical Cream formulation preparation on both sides of both ears (~1 hour).

The mice were treated as indicated in Table 6:

TABLE 6

TREATMENT GROUPS

| Group | Treatment | Dose | Route |
|---|---|---|---|
| 1 | Acetone | 25 μL | Topical |
| 2 | Betamethasone | 25 μL | Topical |
| 3 | Matrix Cream | 25 μL | Topical |
| 4 | Celecoxib | 10 mg/kg | Oral |

0.5 hr, 6 hr, and 12 hr post-oxazolone challenge, the mice were topically applied with 25 μL on both sides of both ears with well-mixed Matrix Topical Cream formulation.

Day 8:

Twenty-four hours after oxazolone challenge, the mice were euthanized, and the ears were removed and weighed.

Experimental Results:

The data obtained from this study are shown below in Table 7, Table 8, and Table 9:

TABLE 7

MOUSE EAR WEIGHTS

| Group | Mouse # | Weight (g) |
|---|---|---|
| 1 | 1 | 22 |
| | 2 | 22 |
| | 3 | 20 |
| | 4 | 22 |
| | 5 | 24 |
| | 6 | 16 |
| | 7 | 22 |
| | 8 | 21 |
| 2 | 1 | 22 |
| | 2 | 22 |
| | 3 | 20 |
| | 4 | 21 |
| | 5 | 20 |
| | 6 | 17 |
| | 7 | 19 |
| | 8 | 23 |
| 3 | 1 | 20 |
| | 2 | 19 |
| | 3 | 24 |
| | 4 | 24 |
| | 5 | 21 |
| | 6 | 23 |
| | 7 | 21 |
| | 8 | 21 |
| 4 | 1 | 21 |
| | 2 | 20 |
| | 3 | 24 |
| | 4 | 21 |
| | 5 | 21 |
| | 6 | 22 |
| | 7 | 22 |
| | 8 | 20 |
| 5 | 1 | 24 |
| | 2 | 22 |
| | 3 | 21 |
| | 4 | 21 |
| | 5 | 22 |
| | 6 | 19 |
| | 7 | 20 |
| | 8 | 20 |
| 6 | 1 | 21 |
| | 2 | 21 |
| | 3 | 20 |
| | 4 | 24 |
| | 5 | 24 |
| | 6 | 23 |
| | 7 | 16 |
| | 8 | 21 |

TABLE 8

EFFECT OF TREATMENT ON MOUSE EAR WEIGHT (MG)

| Group | Mouse | Right Ear | Left Ear |
|---|---|---|---|
| 1 | 1 | 94.70 | 22.91 |
|   | 2 | 108.45 | 23.60 |
|   | 3 | 97.46 | 22.55 |
|   | 4 | 97.53 | 24.16 |
|   | 5 | 103.55 | 24.10 |
|   | 6 | 90.23 | 20.79 |
|   | 7 | 89.13 | 26.20 |
|   | 8 | 103.29 | 23.10 |
| 2 | 1 | 48.00 | 22.10 |
|   | 2 | 45.52 | 23.20 |
|   | 3 | 48.66 | 24.56 |
|   | 4 | 47.03 | 20.44 |
|   | 5 | 41.34 | 21.26 |
|   | 6 | 45.70 | 22.60 |
|   | 7 | 49.51 | 22.60 |
|   | 8 | 46.30 | 25.74 |
| 3 | 1 | 59.75 | 26.43 |
|   | 2 | 58.47 | 25.89 |
|   | 3 | 69.47 | 31.15 |
|   | 4 | 61.50 | 37.87 |
|   | 5 | 68.73 | 30.20 |
|   | 6 | 60.20 | 31.31 |
|   | 7 | 51.60 | 23.68 |
|   | 8 | 58.38 | 26.44 |
| 4 | 1 | 80.37 | 23.15 |
|   | 2 | 70.00 | 26.96 |
|   | 3 | 80.89 | 23.68 |
|   | 4 | 70.00 | 22.00 |
|   | 5 | 78.34 | 21.11 |
|   | 6 | 86.45 | 25.51 |
|   | 7 | 80.26 | 22.21 |
|   | 8 | 72.37 | 20.23 |
| 5 | 1 | 57.96 | 33.98 |
|   | 2 | 69.81 | 33.18 |
|   | 3 | 59.05 | 29.35 |
|   | 4 | 59.94 | 30.49 |
|   | 5 | 59.23 | 33.46 |
|   | 6 | 62.69 | 36.50 |
|   | 7 | 55.67 | 33.69 |
|   | 8 | 75.34 | 40.68 |
| 6 | 1 | 79.55 | 27.52 |
|   | 2 | 68.55 | 25.00 |
|   | 3 | 68.55 | 22.00 |
|   | 4 | 72.46 | 27.84 |
|   | 5 | 81.00 | 30.30 |
|   | 6 | 75.32 | 26.29 |
|   | 7 | 72.39 | 23.89 |
|   | 8 | 62.48 | 23.84 |

TABLE 9

EFFECT OF TREATMENT ON CHANGE IN MOUSE EAR WEIGHT (MG)

| Group | Mouse | ΔWt. |
|---|---|---|
| 1 | 1 | 71.79 |
|   | 2 | 84.85 |
|   | 3 | 74.91 |
|   | 4 | 73.37 |
|   | 5 | 79.45 |
|   | 6 | 69.44 |
|   | 7 | 62.93 |
|   | 8 | 80.19 |
| 2 | 1 | 25.90 |
|   | 2 | 22.32 |
|   | 3 | 24.10 |
|   | 4 | 26.59 |
|   | 5 | 20.08 |
|   | 6 | 23.10 |
|   | 7 | 26.91 |
|   | 8 | 20.56 |
| 3 | 1 | 33.32 |
|   | 2 | 32.58 |
|   | 3 | 38.32 |
|   | 4 | 23.63 |
|   | 5 | 38.53 |
|   | 6 | 28.89 |
|   | 7 | 27.92 |
|   | 8 | 31.94 |
| 4 | 1 | 57.22 |
|   | 2 | 43.04 |
|   | 3 | 57.21 |
|   | 4 | 48.00 |
|   | 5 | 57.23 |
|   | 6 | 60.94 |
|   | 7 | 58.05 |
|   | 8 | 52.14 |
| 5 | 1 | 23.98 |
|   | 2 | 36.63 |
|   | 3 | 29.70 |
|   | 4 | 29.45 |
|   | 5 | 25.77 |
|   | 6 | 26.19 |
|   | 7 | 21.98 |
|   | 8 | 34.66 |
| 6 | 1 | 52.03 |
|   | 2 | 43.55 |
|   | 3 | 46.55 |
|   | 4 | 44.62 |
|   | 5 | 50.70 |
|   | 6 | 49.03 |
|   | 7 | 48.50 |
|   | 8 | 38.64 |

Results of the statistical analysis of the recorded data are shown in Table 10:

TABLE 10

EFFECT OF TREATMENT ON AVERAGE CHANGE IN EAR WEIGHT (MG)

| Group | Treatment Regimen | Statistic | Change in Ear Weight (mg) | % Inhibition |
|---|---|---|---|---|
| 1 | Acetone Vehicle | Mean | 74.6 | — |
|   |   | SD | ±6.9 |   |
| 2 | Topical Betamethasone | Mean | 23.7 | 68 |
|   |   | SD | ±2.6 |   |
|   |   | p vs. Grp 1 | $1 \times 10^{-8}$ |   |
| 3 | Matrix Topical Cream | Mean | 31.9 | 57 |
|   |   | SD | ±5.1 |   |
|   |   | p vs. Grp 1 | $3 \times 10^{-9}$ |   |
| 4 | Oral Nutraceuticals | Mean | 54.2 | 27 |
|   |   | SD | ±6.0 |   |
|   |   | p vs. Grp 1 | $2 \times 10^{-5}$ |   |
| 5 | Oral Nutraceuticals + Matrix Topical Cream | Mean | 28.5 | 62 |
|   |   | SD | ±5.1 |   |
|   |   | p vs. Grp 1 | $1 \times 10^{-9}$ |   |
| 6 | Oral Celecoxib | Mean | 46.7 | 37 |
|   |   | SD | ±4.3 |   |
|   |   | p vs. Grp 1 | $6 \times 10^{-7}$ |   |

Significance (p-value) was calculated by t-test.

Topical application of a matrix cream formulation (25 μL cream containing five nutraceutical families totaling 13.44 mg active ingredients/cc), starting 12 hrs prior to oxazolone challenge and continuing until 12 hrs after challenge, resulted in a significant reduction in the oxazolone-induced ear edema.

Oxazolone-Induced Ear Edema (Control Group 1):

In oxazolone-sensitized mice topically applied with 25 μL of acetone one hr prior to oxazolone challenge, a 4.2-fold increase in ear edema over the un-challenged ear was recorded.

Effect of Prophylactic Treatment with Betamethasone (Group 2):

Topical application of 25 μL of a 40 μg/mL solution of betamethasone one hr prior to oxazolone challenge resulted in a significant 69% reduction in the ear edema.

Effect of Prophylactic Treatment with Matrix Topical Cream Formulation (Group 3):

Topical application of 25 μL/ear (both sides) of well-mixed Matrix Topical Cream (specific formulation for this study is shown in Table 11), starting 12 hr prior to oxazolone challenge and continuing at intervals for 12 hrs after oxazolone challenge, resulted in a statistically-significant, 57% inhibition of the oxazolone-induced edema.

Figure 10:
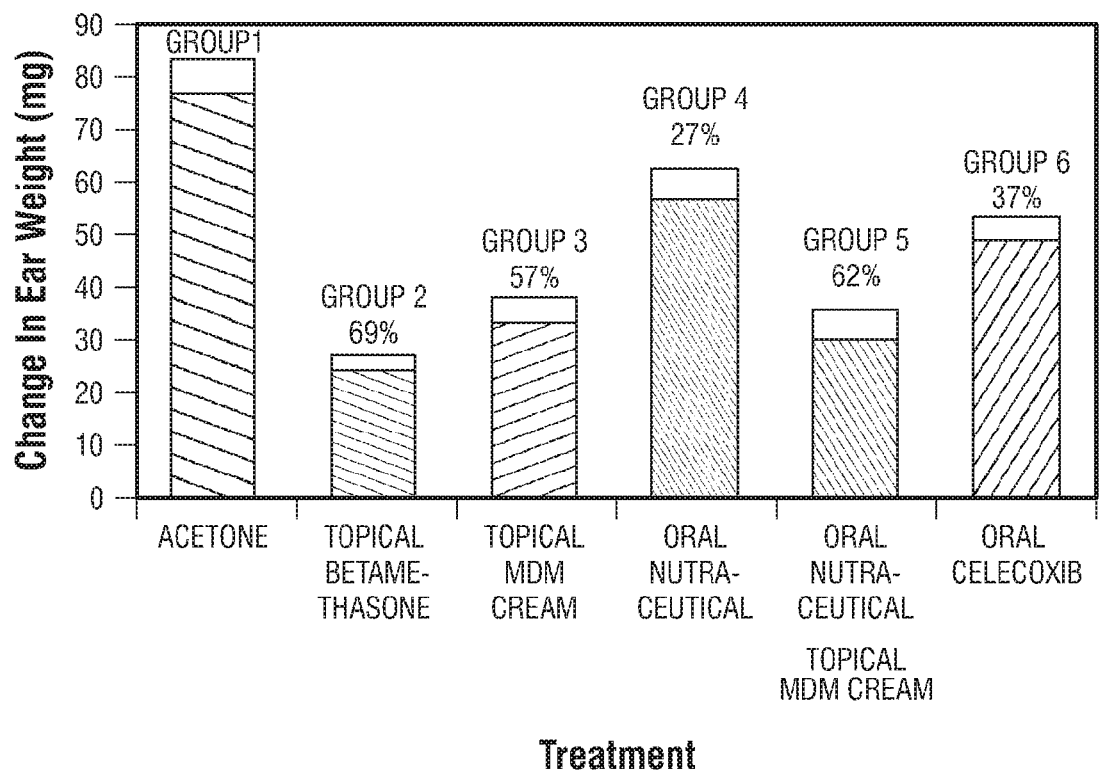
FIG. 10 shows the effects of pre-treatment on oxazolone-induced murine ear edema, and illustrates outcomes from the second, formalized in vivo study illustrating the synergistic reduction of ear edema using both the exemplary topical formulation, and an oral nutraceutical powder containing quercetin, turmeric, green tea extracts, skullcap, and bee propolis.
Figure 11:
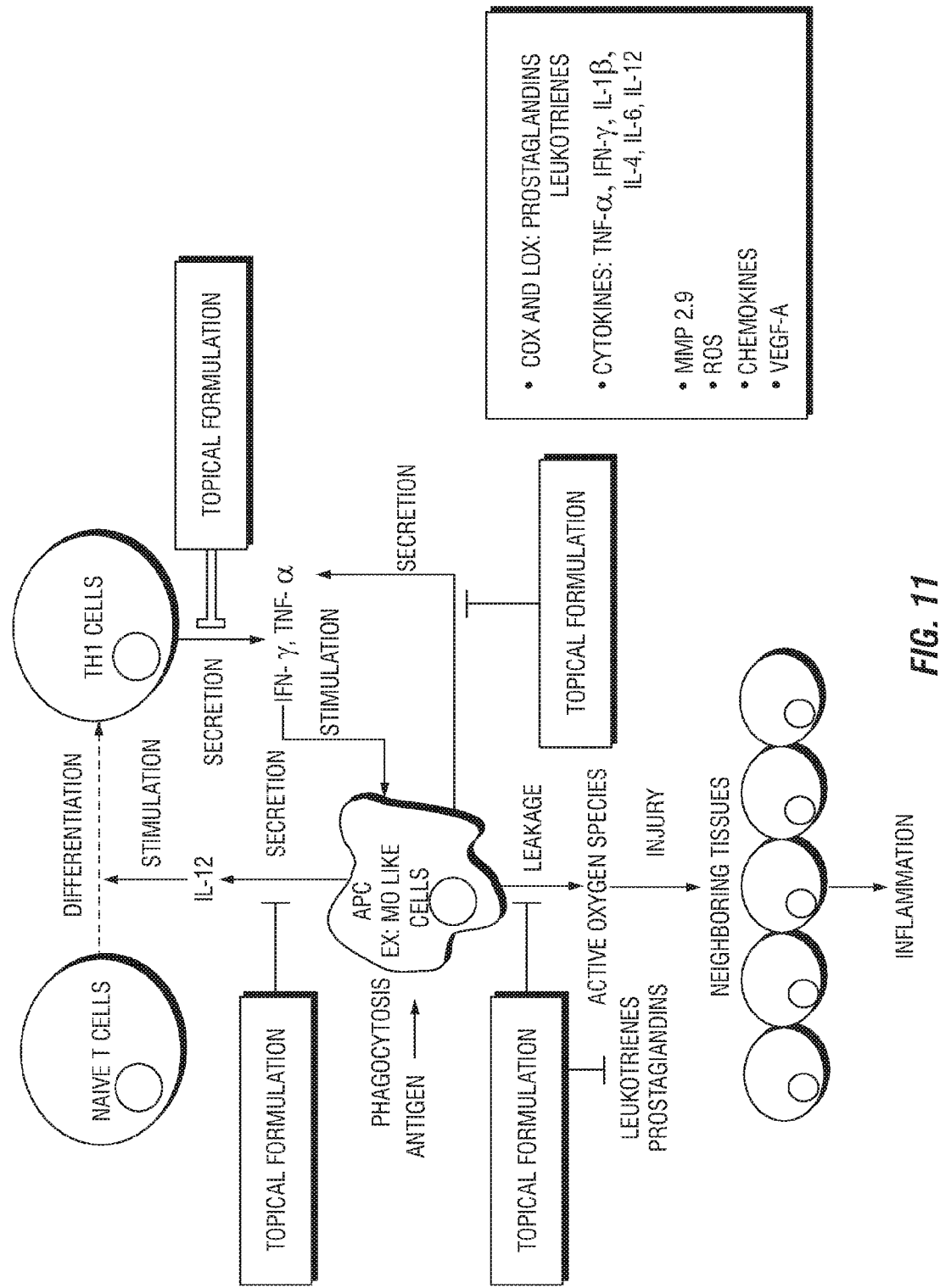
FIG. 11 shows the oxazolone-induced murine ear edema model is based on cells that exist within the stromal ECM.

Effect of Prophylactic Treatment with Oral Nutraceuticals (Group 4):

FIG. 10 includes an oral powder that contains particular nutraceutical components of the present invention. The powder was dosed at 200 mg/kg body weight daily in a separate group of mice. A significant 27% reduction in edema resulted, but this was significantly less that observed in the animal group receiving the topical formulation.

Effect of Prophylactic Treatment with Oral Nutraceuticals and Matrix Topical Cream (Group 5):

Addition of the topical formulation application regimen to the daily oral powder for 12 hours after oxazolone-induced injury reduced swelling by 62%. The therapeutic use of cream combined with the prophylactic use of powder was

TABLE 11

AN EXEMPLARY 2ND-GENERATION ORTHOMOLECULAR FORMULATION

| Ingredient | % (wt./wt.) | Family |
|---|---|---|
| PHASE A | | |
| Water | 60 | |
| PHASE B | | |
| Isopropyl palmitate | 3 | |
| Isopropyl myristate | 3 | |
| Lipowax D (cetearyl alcohol and ceteareth-20) | 5 | |
| SabiWhite ™ (tetrahydrocurcumin from *Curcuma longa*) | 0.25 | Curcuminoids |
| Tetrahydrocurcuminoids CG ™ (standardized power from *Curcuma longa*) containing: Tetrahydrodiferuloylmethane Tetrahydrodemethoxydiferuloylmethane Tetrahydrobisdemethoxydiferuloylmethane | 0.25 | Curcuminoids |
| Cosmoperine ® (tetrahydropiperine from black pepper) | 0.05 | Curcuminoids |
| DL-α-Lipoic Acid | 0.15 | |
| Keltrol CG (xanthan gum) | 0.1 | |
| PHASE C | | |
| Transdermal Compounding Base† (PCCA Lipoderm ®) | 8 | |
| Tetrahydrodiferuloylmethane (i-Sabi ™, *W. japonica* powder) | 2 | Isothiocyanate |
| Broccoli seed oil with SGS (from *Brassica oleracea*) | 5.4 | |
| Mustard seed oil (from *Sinapis juncea*) | 0.2 | |
| Broccoli seed powder (from *Brassica oleracea*) | 0.3 | Isothiocyanate |
| Melatonin | 0.1 | |
| N-Methyl-2-pyrrolidone (NMP; Pharmasolve ®) | 2.5 | |
| Cholecalciferol (Vitamin $D_3$) | 1.5 | |
| α-Tocopherol acetate (Vitamin E) | 1 | |
| 3'3-Diindolylmethane (DIM) | 0.4 | |
| 3,5,4'-Trihydroxy-trans-stilbene (Resveratrol) | 1.2 | Stilbenoids |
| 4-[(E)-2-(3,5-Dimethoxyphenyl)ethenyl]phenol (pterostilbene) | 0.8 | Stilbenoids |
| PHASE D | | |
| *Boswellia serrata* essential oil (5 drops in 87 mL) | 0.3 | Essential Oil |
| *Boswellia carterii* essential oil (5 drops in 87 mL) | 0.3 | Essential Oil |
| Rosemary essential oil (8 drops in 87 mL) | 0.5 | Essential Oil |
| Sweet orange essential oil (absolute) | 0.6 | Essential Oil |
| Thyme essential oil (10 drops in 87mL) | 0.6 | Essential Oil |
| Clove essential oil (5 drops in 87 mL) | 0.3 | Essential Oil |
| Turmeric essential oil (1 drop in 87 mL) | 0.05 | Essential Oil |
| Optiphen ® Plus (phenoxyethanol, caprylyl glycol and sorbic acid) | 1.25 | |
| Epigallocatechin gallatyl glucoside (EGC-GINE as green tea) | 0.4 | Catechin |
| PHASE E | | |
| Sepigel 305 (polyacrylamide based emulsion/rheology modifier) | 1 | |
| TOTAL | 100.44 | |

*Lipoderm ® Base (PCCA, Houston, TX, USA) ingredients: *Pentaclethra macroloba* Seed Oil, *Plukenetia volubilis* Seed Oil, Phosphatidylcholine, *Chartamus tinctorius* (Safflower) Seed Oil, Hydrogenated Lecithin, *Butyrospermum parkii* (Shea) Butter, Caprylic/capric triglyceride, Water, Alcohol, Glyceryl stearate, *Cocos nucifera* (Coconut) Oil, Squalane, Ceramide 3, Ascorbyl palmitate; and Potassium sorbate.

89.8% as effective as topical betamethasone and 68% more effective than oral celecoxib.

Effect of Prophylactic Treatment with Oral Celecoxib (Group 6):

Celecoxib is a non-steroidal anti-inflammatory drug (NSAIDs) which is a selective cyclooxygenase-2 (COX-2) inhibitor. Studies have confirmed that transgenic overexpression of COX-2 induces mammary tumor formation in rodents. Matrix stabilization is adversely influenced by COX-2 activation of dysregulation of proliferation, apoptosis, angiogenesis, invasion, and immune responsiveness. Patterns of COX-2 overexpression differ substantially between breast and colorectal neoplasia. A single oral dose of 10 mg/kg celecoxib one hour prior to oxazolone challenge resulted in a significant 37% inhibition of the edema.

Figure 8A:
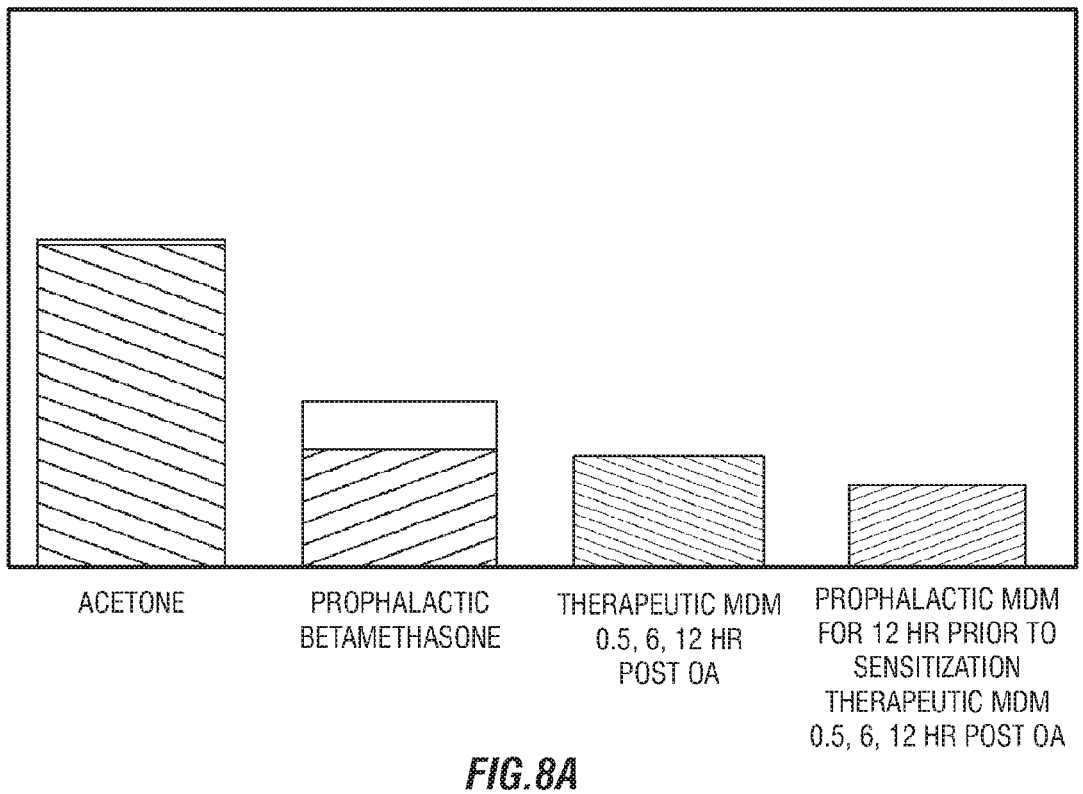

FIG. 8A illustrates an exemplary oxazolone ear edema study, which showed that the denoted compositions are capable of stabilizing the matrix against inflammatory injury by prior and post injury application. The degree of protection is comparable to that of the potent pharmaceutical steroids. The preventative components of the topical formulation in stabilizing the tissue matrix prior to onset of an inflammatory event offer a prophylactic treatment capability.

FIG. 8B shows that the data collected in this initial study was in agreement with a second, formalized, ear edema study that utilized eight study animals for each formulation tested.

Figure 8C:
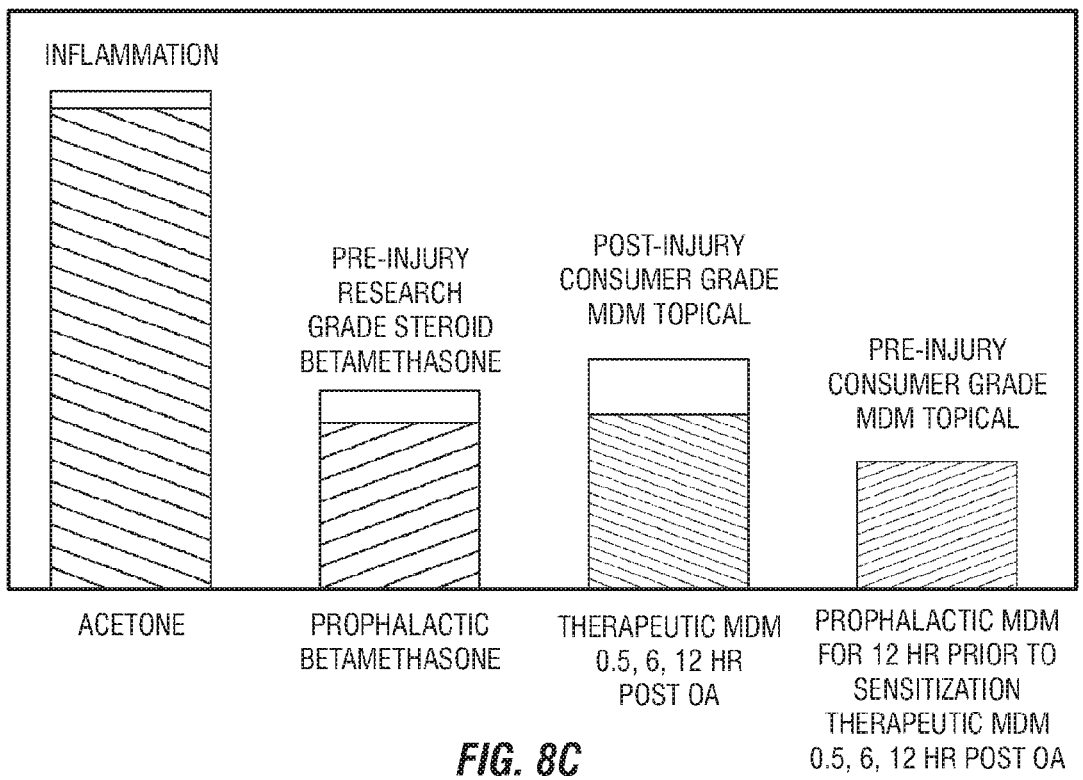

FIG. 8C illustrates that application of the topical denoted compositions formulation post injury was capable of stabilizing the ECM thus decreasing the leakage of fluid across the vascular bed thereby reducing edema. Intervention post-injury to the matrix using the topical formulation yielded reduction of ear edema comparable to that of the pharmaceutical steroid, which had been applied prior to injury.

Figure 9:
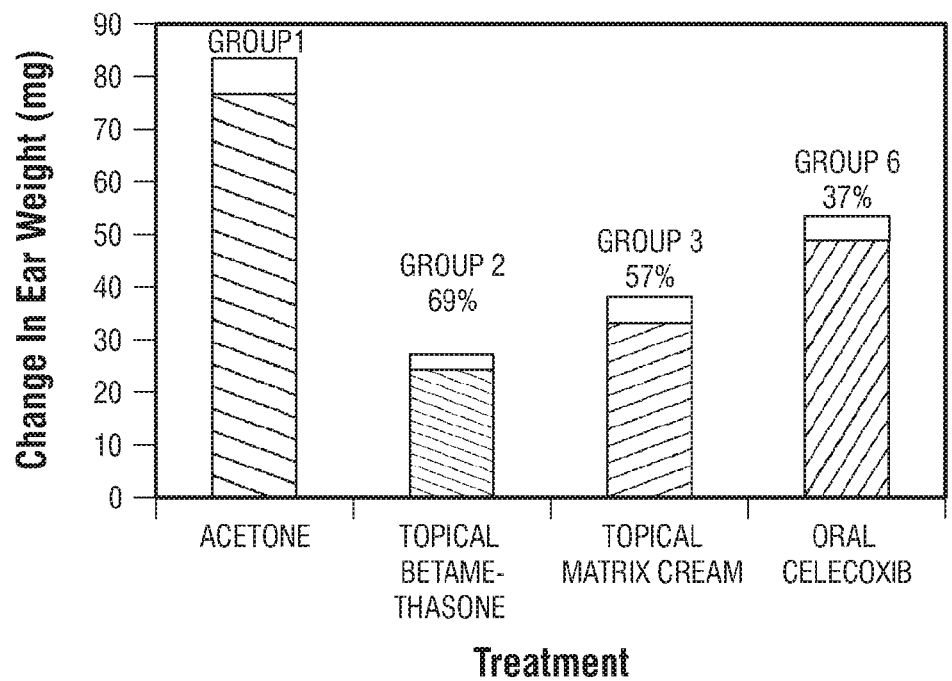
FIG. 9 shows the effect of pre-treatment on oxazolone-induced murine ear edema, and graphs a second, formalized in vivo study outcomes illustrating the reduction of oxazolone-induced ear edema using acetone control, topical betamethasone, an exemplary topical orthomolecular composition formulation; and oral celecoxib.

FIG. 9 illustrates that the topical formulation containing the denoted compositions had a statistically-significant, inflammation-lowering effect, as compared to oral high dose celecoxib, while exhibiting comparable efficacy to that of pharmaceutical steroids. This second, formalized in vivo study involved the use of eight study animals per tested formulation group. The "p" values have been listed.

FIG. 10 shows other formulations tested in the second, formalized in vivo murine ear edema study, that included administration of an oral nutraceutical preparation containing turmeric, green tea extracts, skullcap, bee propolis, and quercetin to two of the test groups (Groups 4 and 5). The oral nutraceutical formulation significantly reduced inflammation, but was statistically less effective than the topical formulation containing the denoted compositions (Group 3). The combination of the oral nutraceutical plus the topical formulation (Group 5) resulted in a significant reduction inflammation comparable to that of the pharmaceutical steroid (Group 6). A 5% improvement in inflammation reduction compared to topical formulation only use was realized in the oral+topical test group (Group 5).

Summary

The ECM-promoting topical cream formulation used in this in vivo study contained orthomolecular molecules from each of the five-nutraceutical families discussed herein. The dosing formulation and carrier base were similar to that used in the human breast thermography study described in the preceding example.

0.336 mg of active ECM-promoting topical cream formulation applied to oxazolone-treated ears resulted in a 57% inhibition of edema as noted in FIG. 9. Studies using individual topical nutraceutical components such as research grade trans-resveratrol (A commercially-purified trans-resveratrol at similar concentration to that of Table 4 topical formulation inhibited edema by 35%) report a 36% to 40% inhibition while the topical pharmaceutical indomethacin (0.5 mg/ear) produced a 45% reduction. Other models such as the carrageenan paw edema and TPA induced ear edema have also been used to compare anti-inflammatory response of individual topical ingredients used in the patent formulation. Boswellic acids used in the carrageenan paw edema inhibited swelling by 13% compared to control. Tea theaflavin (EGCG source) reduced TPA induced ear edema by 18% while extracts of rosemary in doses comparable to that found in the Table 4 cream inhibited TPA induced edema by 17% compared to controls.

Topical application of the disclosed Matrix Cream Formulation resulted in a high concentration of bioactive orthomolecular molecules to a defined treatment area such as the murine ear. Application of the cream prior (prophylactic) to the oxazolone-induced injury and for 12 hours afterwards resulted in a reduction of edema that was 82.6% as effective as the potent topical pharmaceutical betamethasone and 54% more effective than oral celecoxib.

These data demonstrated the synergistic action of the actives contained in the topical orthomolecular formulation with respect to stabilization of the ECM when co-administered with an oral anti-inflammatory nutraceutical composition (Group 5). Moreover, the in vivo animal studies also demonstrated that the disclosed topical orthomolecular formulations were useful in both prophylaxis and in therapy of inflammation, and for stabilization of the mammalian ECM.

Example 6

Evaluation of Anti-Inflammatory Effects of Topical Application of Matrix Cream

This example includes a case study that illustrates: 1) the difficulty or shortcomings in evaluation of dense breast tissue using conventional mammographic techniques, 2) the progressive increase in thermographic signatures resulting from destabilization of the extracellular matrix and manifested by distinct expanding areas of MVD which were associated with biopsy proven neoplastic changes, 3) the impact of use of a transdermal orthomolecular cream as described herein) applied to the breast for an 18 months resulting re-stabilization of the extracellular matrix with reduction of MVD areas (per infrared imaging) and resolution of the MVD associated with biopsy proven ALH and ADH, and 4) the chemoprotective effects derived from moderate persistent cream use.

Patient "CK," at 65 years old, had yearly mammograms revealing only Grade 4 dense breast until 2010 when her mammogram revealed a vague sonographic hypo echogenicity in the left breast at the one o'clock position. A biopsy was performed, and it was scored by pathology as "atypical lobular hyperplasia."

In addition to mammograms, thermograms were also performed yearly with the 2010 thermogram revealing suspicious MVD infrared patterns. These areas of suspicion were noted in the upper quadrants of the right breast and the inner lower quadrants of the left breast. Following an MRI, a biopsy of the upper inner quadrant of the right breast (at the one o'clock position) revealed "atypical lobular hyperplasia," while no evidence of a mass was noted in the lower quadrant of the left breast.

Thermographic images Rt. Oblique and Lt Oblique. MVDs are circled with: A) area "2" in the upper outer quadrant of the left breast containing ADH, B) area "2" in the right breast upper inner quadrant containing ALH, and C) area "1" in the left breast containing prominent MVD but negative radiographic imaging.

A prior thermogram taken of this patient five years prior served as a comparison.

This patient was then instructed after the 2010 biopsies to apply the topical formulation of nutraceutical actives to each breast at least five days per week. During the next eighteen months, two mammograms were performed and read as benign with another thermogram being performed in 2012.

After using the transdermal matrix stabilizing formulation described herein for approximately 18 months, thermograms taken of the patient showed a decrease in vessel prominence and intensity of MVD patterns. A visual comparison was made of the 2008, 2010, and 2012 temperatures and thermographic images of the right oblique view. Also included was a "ΔT" calculated temperature differential which was derived by subtracting the "average temperature" of a neutral average skin area ($T_m$) located at area 1 on the mediastinum pic from the Rt Oblique MVD area2(Rt2). Rt2−$T_m$=ΔT (° C.) compares the change in temperature of the breast MVD to a neutral stable body temperature (remote from the matrix destabilizing VEGF).

Using a neutral site average body temperature is necessary in order to correct for variations in: 1) thermogram room temperature 2) daily whole body temperature and 3) dietary intake of thermogenic foods. ΔT results can then be used to examine thermographic trends and changes in angiogenic patterns when comparing sequential images taken over a period of time (4 years).

Data obtained from this patient revealed that from 2008 to 2010, the temperature differential went from 0.7 to 1.4. This increase in heat reflects the continuing destabilization of the ECM (mediated by chronic inflammation) resulting in an increased release of VEGF turning on the angiogenic switch and intensifying the MVD. An increasing MVD indicates that more blood was being diverted to an active neoplastic process which would eventually give rise to the biopsy report, atypical lobular hyperplasia.

The ΔT dropped from 2010 to 2012 (1.4 to 0.3) which reflects the ECM stabilizing effects of the topical active nutraceutical formulation. The cream contains VEGF blocking molecules such as EGCG, sulforaphane, rosemary, curcuminoids, and resveratrol. Also included in the formulation are anti-inflammatory orthomolecular substances which block the release of VEGF activating proteases. The dramatic decline in ΔT suggest that there was a decrease in blood flow and a diminished MVD resulting from a re-stabilization of the ECM. A reversal of abnormal cell histology and molecular formation would be expected. Indeed the rt breast pathology report post-2012 mastectomy revealed that there was no atypical lobular hyperplasia (previously reported in 2010). Fibrocystic changes, usual ductal hyperplasia, sclerosing adenosis with microcalcifications, and no malignancy were noted on the path report.

Following this thermogram, Patient CK underwent a double mastectomy, after a mass was detected at the 6- to 8-o'clock region in her left breast. This was in the approximate area of high MVD which had been previously noted in an earlier thermography report. Reference to pathology reports were then based upon mastectomy specimens.

The Lt Oblique ΔT(C) (temperature change in the specified MVD area 2 compared to that of a stabilized body point) followed a similar direction as the Rt. Oblique. One would have expected that the conditions which promote chronic inflammation and de-stabilization of the ECM in one breast most likely would exist in the contralateral breast. The earlier thermogram indicated a lower temperature for area 2 of the breast compared to the body reference site (mediastinum). As expected, application of the topical orthomolecular formulation to the left breast stabilized the ECM, which led to a reduction of the MVD amount. The left mastectomy pathology report noted that there was no atypical ductal hyperplasia found in the upper left breast quadrant.

Thermographic imaging of blood vessels and accompanying MVD originating from the left internal thoracic or mammary artery was performed. These prominent vessels (medial branches of the internal thoracic artery) were noted in the initial exam, but markedly intensified in the exam performed two years later, suggesting an escalating destabilization of the ECM with neoplastic changes in the lower left breast quadrants (below the nipple). These intense gray images suggested chronic inflammatory changes manifested as: 1) higher levels of tissue destructive proteases, 2) a larger VEGF gradient, and 3) deeper matrix injuries.

A significant decrease in temperature was noted in 2012, which was attributable to continued application of the topical antiinflammatory cream formulation. Yet there was still a very distinctive vessel pattern observed, having a significant MVD. One might expect that a slowing of the neoplastic process has occurred, but not a complete resolution. This was later confirmed by the pathology report post-mastectomy. A tumor 5 cm below the nipple between 6 and 8 oclock was found in the left mastetcomy specimen. The tumor was noted to be a grade 1 invasive tubulolobular carcinoma 6 cm in size with negative nodes.

Although the topical formulation used by this patient did not contain cytotoxic levels of nutraceuticals (as determined from previous research), persistent moderate dosing of the multicomponent phytoactive topical formulation to the left breast had resulted in a "chemoprotective" effect. Chemoprotection (as opposed to chemoprevention) implies the use of nutraceutical agents to limit the growth and spread of the malignant tumor. These results indicated that the disclosed topical formulations could also be viewed as adjunctive treatments to traditional debulking and chemotherapeutic intervention. Once a tumor has reached a certain size, cytotoxic dosing is required for complete erradication.

This patient had an undiscovered malignancy which was becoming more aggressive (per serial thermography) via an increasing blood supply and because of lack of radiographic visualization for proper diagnosis. Delaying treatment would have allowed the tumor to increase in size and eventually metastasize. By directly applying the active phytonutrient topical with potent anti-inflammatory properties to the breast to reduce inflammation and tumor blood flow, accounts for the low malignancy potential of grade 1 and the extremely rare encapsulation of a 6-cm malignancy with no apparent node involvement.

Re-stabilization of the ECM surrounding the tumor: a) prevents recruitment of stromal cells for tumor progression, b) places a restrictive lattice work (mechanosignaling) around the tumor to prevent further growth and metastasis, c) defines the tumor boundaries and in certain cases reduces breast density allowing for earlier detection and treatment and d) inhibits the release of growth factors (VEGF) which reduces metaboolic fuel for tumor growth. A lowering of tumor grade which is a measure of tumor aggressiveness must also be considered in ECM stabilization.

Example 7

The Role of a Transdermal Orthomolecular Formulation in ECM Stabilization Characterized by Dense Breast Tissue Mammographically, dense breast tissue presents one of the greatest independent risk factors for developing breast cancer especially in postmenopausal women. The chances for being diagnosed with breast cancer are increased by greater than four-fold with 30% of breast cancers being found in breasts that manifest at least 50% dense tissue. Pre-invasive breast disease (DCIS) overwhelmingly arises in dense regions of the breast.

Increased breast density makes it more difficult for radiographic detection of a tumor. As a result, various studies have reported a range of 7 to 15% false-negative mammogram rate for tumor detection. Some state legislatures have even passed laws requiring mammogram facilities to formally notify those patients with dense breast tissue discovered at the time of their mammogram.

Practitioners are faced with the dilemma of not only how to detect abnormalities in dense breast but what approach is needed to decrease the excessive density. A debate now rages as to when to begin routine mammogram screening since women below the age of 50 generally have denser breast tissue. Tamoxifen has been shown to have an effect on decline in density but side effects prohibit its use on a general population.

A review of the scientific literature to explain the underlying etiology of dense breast, suggests that the ECM is key to understanding the pathophysiology involved in high mammographic density (MD).

Increases in breast density are associated with: a) a lower percentage of adipose cells in the breast b) increased epithelial and stromal cellularity, and c) a marked increased fibrillar collagen deposition. A complex interplay of excessive amounts of type VI collagen, activation of the epithelial-mesenchymal transition (EMT) and collagen induced transmission of multi-axial deformations to the individual breast cell promote cancerous growth and metastasis.

Increased Breast Density and the ECM Mechanical and Molecular Mechanisms Involved in High MD Dysfunctional mechanotransduction to the breast cell can result because of remodeling the ECM. Stromal fibroblasts are responsible for the release of excessive collagen. These dense collagen matrices, independent of stromal cellularity, are associated with increased matrix stiffness that results in proliferation and invasion by cells with a malignant phenotype. Increased matrix stiffness is associated with increased adhesion signaling and chronically elevated activation of a FA-RhoGTPase-MAPK network.

Finding repressed CD36 expression (CD36 is expressed 30 to 100 fold less in aggressive cancer cells). The importance of the platelet integral membrane glycoprotein (CD36), which acts as a receptor for TSP-1 (thrombospondin-1), has been reported in the literature. CD36 functions as a transmembrane receptor modulating multiple pro-tumorigenic phenotypes that include adipocyte differentiation, angiogenesis, cell-ECM interactions, and immune signaling. It is greatly repressed in high MD. Sulforaphane has been shown to enhance CD36 expression, and increase release of molecules by stromal fibroblasts such as proteases (MMP-9) and TSP-1 (expression of TSP-1 was approximately 50-fold higher in the aggressive cancer cell line) which promote motility, cell proliferation, TGF-β activation, and angiogenesis. TSP-1 increase leads to TGF-β switching on tumorigenic cell functions such as EMT. Varying the matrix rigidity with increased collagen deposition produced by fibroblast also activates EMT. ROS (reactive oxygen species generated by chronic inflammation) increase MMP, which break down tissue and activate EMT. The orthomolecular ingredients in the topical formulation block multiple inflammatory pathways reducing the generation of ROS.

The combination of at least five phytoactive groups included in the disclosed topical anti-inflammatory formulations results in blockage of aberrant pathways that are present in the ECM and cellular components of high MD. These nutraceuticals act to stabilize the ECM and to interrupt cell pathways (activated by matrix stiffness) that lead to uncontrolled proliferation and metastasis. In particular, sulforaphane inhibits the epithelial-to-mesenchymal transition (EMT) process that underlies tumor cell invasion and migration mediated by E-cadherin induction through reducing transcriptional repressors, such as ZEB1 and Snail. Sulforaphane induces Nrf2 (but not PPARγ ligands) for enhanced CD36 expression (in contrast to Tamoxifen, which decreases CD36 expression); decreases MMP-9 and TNF-α expression (matrix destabilizers); and inhibits NF-κB, phosphoinositide-3-kinase (PI3K)/AKT, and mitogen-activated protein kinase (MAPK)/ERK kinase (MEK) activation pathways. Likewise, EGCG, curcumin, and *Boswellia* have been shown to inhibit Ras/MAPK and various other pathways as noted herein. Both EGCG and curcumin inhibit TGF-β-induced EMT. Resveratrol acts via a Ras-MAPK kinase-MAPK signal transduction pathway to increase p53 expression, serine phosphorylation, and p53 apoptosis; it also inhibits TGF-β-induced EMT.

Example 8

Anti-Inflammatory Properties of Topical Cream Formulations Clinical Correlation of Two Cases Case Presentation 1

Clinical case correlation using topical anti-inflammatory formulations of the present invention (including ingredients from each of the five families of nutraceuticals) in women with dense breast was established with two human patients.

In the first case, referring to the discussion concerning pre-invasive lesions and high MD, Patient "CK" had ALH and ADH that were noted to regress after using the topical nutraceutical formulation. Patient "CK" had extremely dense noted on her mammogram readings. She had several radiographic procedures over the next two years including an MRI in July 2010, which was read as negative. This was followed by mammograms in 2010 and in December 2011. In the first mammogram, recorded in December 2010, History:

Established patient. Follow-up benign biopsies in both breasts yielding atypical hyperplasia according to the patient. No current clinical complaint.

CAD:

This mammogram was interpreted with the assistance of computer-aided detection, R2 version Cenova 1.0.

Breast Composition:

Extremely dense.

Finding:

Full-field digital mammography was performed. Standard views of both breasts were obtained and compared with prior studies. Postsurgical changes are present. No suspicious findings were observed.

Impression:

No suspicious imaging findings.

Plan:

Routine follow-up mammogram in accordance with the guidelines of the American Cancer Society is recommended.

Patient "CK" obtained a follow-up mammogram. The report, prepared several months after her biopsies, revealing bilateral breast hyperplasia, and "extremely dense" breast.

History:

Established patient. No significant problems reported.

CAD:

The mammogram was interpreted with the assistance of computer-aided detection. R2 version Cenova 1.0.

Breast Composition:

Grade 4: The breast tissue is extremely dense. This may lower the sensitivity of the mammography (>75% glandular).

Impression:

Full-field digital mammographic views were obtained. No evidence of malignancy or other significant abnormality. No interval change when compared with previous mammograms.

Plan:

Routine screening under guidelines of the American Cancer Society.

BI-RADS 1:

Negative.

A mammogram was also read as "negative" with extremely dense breast. Approximately ten months after her mammogram, the patient, while performing a self-examination, noted a mass in the left breast which upon biopsy was noted to be a 6-cm malignant tumor. High MD delays diagnosis of tumors because of the inability to detect using conventional radiographic modalities.

Patient "CK"'s case revealed the greater risk of being diagnosed with breast cancer for those with high MD, the high false negative rate mammogram results associated with extremely dense breast, and the effective use of a transdermal orthomolecular formulation which re-stabilizes the ECM, inhibits the excess release of growth factors into the ECM, and prevents the activation of proliferative pathways induced by increased matrix stiffness.

Case Presentation 2

Case correlation 2 involves a menopausal woman (Patient "HB") who was hormone replacement therapy for several years and had dense breast tissue reported by screening mammogram. Mammograms in 2010 and 2011 both revealed heterogeneous densities.

History:

No significant problems reported. Screening mammogram.

CAD:

Full-field digital mammography was performed. This mammogram was interpreted with the assistance of computer-aided detection, iCAD version 7.2.

Impression:

The breast tissue is heterogeneously dense, which limits a mammographic sensitivity. No evidence of malignancy or other significant abnormality. No Interval change when compared with previous mammograms.

Plan: Routine screening under guidelines of the American Cancer Society.

Patient "HB" was instructed to apply the topical cream formulation (standard composition) daily to each breast. After almost 18 months, a repeat mammogram was performed, and no evidence of dense breast tissue was observed.

A resolution of dense breast allows for improved radiologic monitoring and indicates curtailing of abnormal proliferating cell patterns. It takes at least one year of routine cream use to mammographically-appreciate a decrease in MD, which is similar to Tamoxifen. While the ability of the topical formulation to decrease the MD is mainly limited to cases involving heterogeneously dense breast, the ability to favorably modulate potential neoplastic pathways involved (angiogenic switch, MVD) in high MD are still observed regardless of density resolution (see thermographic studies).

High mammographic density is associated with pathologic processes occurring within the ECM, and in the interior of the cell (by means of cell-matrix communication). At the molecular level, the following were observed: 1) ECM remodeling with increased production of collagen by stromal fibroblast; 2) the release of growth factors, pro-angiogenic factors, and proteases (MMP-9) into the matrix which influence the growth of cells with pre or overt malignant phenotypes; and 3) changes in mechano-signaling that lead to increased matrix stiffness, allowing for cell proliferation and metastasis.

The observation-based clinical outcomes seen in this example confirmed that use of a transdermal orthomolecular formulation applied to the breast was able to down-regulate molecular paths that are attributed to aberrant proliferation and metastasis of cells with pre- or overt malignant phenotype. Resolution of atypical hyperplasia has been documented along with confining tumor metastasis in high MD tissue. A clinical approach to high MD could therefore be accomplished with long-term topical usage of the disclosed formulations. Clinical observations suggest that prevention of high MD is also possible with moderate persistent use beginning in a woman's reproductive years and extending through the post-menopause.

Example 9

Extracellular Matrix Intervention—Clinical Correlation of Two Cases

Case Presentation 1

Patient "CZ" was diagnosed in 2005 with multicentric invasive intraductal carcinoma of the left breast after undergoing a needle biopsy. The location of the biopsy was at the 4 o'clock region and approximately 6 cm from the nipple. In spite of her physician's advice, she decided not to receive any further medical treatment at that time. Instead, she opted for observation, and change of her lifestyle habits.

Her breast thermograms or infrared vascular mammograms (IVM) continued over a period of 6 years while a subsequent PET scan in the seventh year revealed no areas of recurrent or metastatic disease.

A PET scan was positive with uptake noted in the left lateral breast (same location as previous tumor). The focal uptake was slightly speculated and a follow up biopsy confirmed a recurrence of the original tumor. An ultrasound of the left breast in late December 2011 was read as:

Left digital mammogram showed a spiculated area consistent with residual malignancy, prior positive diagnosis without interval surgery.

Ultrasound of an area of prominence left breast shows what is thought to represent the primary malignancy left breast 4 o'clock, 6 cm from the nipple somewhat difficult to measure but measuring at least 2.2×1.7×2.4 cm.

Prior reports described a lesion left breast 2 o'clock, 7-8 cm from the nipple. In that area, a definite identifiable lesion cannot be identified, but there is a focal area of shadowing with hypervascularity, probably representing a second focus of malignancy measuring approximately 1 cm in diameter though difficult to measure accurately.

Two lesions were noted on the sonogram report. The largest lesion was 2.2×1.7×2.4 cm (at the primary cancer site) while a smaller irregularity was a 2 o'clock but 7 cm from the nipple. She was advised once again to see a cancer specialist. Until medical treatment began, Patient "CZ"

agreed to start treatment using the transdermal orthomolecular formulation twice daily (a total of 2 cc/day) to the left breast and once daily to the right breast. ΔT(C)=Avg T of Area 3–neutral body T (because of upper chest involvement, the back of the neck was used).

A series of thermograms were performed in 2006, 2007, and 2012. From the initial 2006 thermogram, it appeared that a significant MVD pattern still existed in the previous tumor site along with a prominent vascular component formed by the upper medial mammary branches of the internal thoracic artery. One would expect that residual tumor remained since the patient refused standardized cancer treatment. In spite of her attempts at adequate oral ingestion of foods containing cancer-fighting elements, the 2007 thermogram showed an increased ΔT(C), from 0.4 to 1.8, which indicated an increased blood flow in the region of the left breast contained within the oval area (3). As previously discussed, oral intake of orthomolecular ECM stabilizers are diluted by at least one-millionth of their original strength, as opposed to topicals, which suffer a dilution of less than one-thousandth. At one-millionth the original strength, orally-ingested nutrients are not as biologically active, and are not present in sufficient dose to effect clinical improvement.

As noted in a prior thermogram, a marked decline in ΔT(C) (from 1.8 to 1.01) was observed, approximately thirty days after starting the topical formulation. A reduction in blood flow suggests a curtailing of metabolic fuel to the tumors and a reduction of inflammation. Re-stabilization of the ECM, should not only slow the growth of the tumor, but also encourage partial regression based on transdermal strength, duration of application, and tumor markers. As with the other clinical examples, a standardized formulation (Table 11) of the matrix cream formulation was employed.

A repeat sonogram was performed and compared with one previously taken. The following clinical observations were noted: Ultrasound of the region at 4 o'clock 6 cm from the nipple demonstrates a hypoechoic solid irregular mass, which was the biopsy-proven cancer. There was a biopsy clip seen in place. The mass had decreased in size compared with the study in 2011. Comparable measurements to what were obtained on the old study give a measurement of 2×2×1.6 cm.

Ultrasound at the 2 o'clock position, 7 to 8 cm from the nipple still demonstrated an area of slightly hypoechoic echotexture not a clearly defined mass with some vascularity associated with that. It is difficult to give precise measurements on this area but does appear slightly less prominent than on the oil study.

After use of the transdermal nutraceutical preparation for 4 months, both lesions had decreased in size. Upon comparison of tumor volume change, a 29% reduction in volume occurred after 4 months use of the topical cream formulation.

Case Presentation 2

Patient "CN" was seen in December 2012 after being diagnosed with a primary left-sided breast cancer-grade 2 invasive ductal carcinoma with DCIS. The tumor was located at 1 to 2 o'clock 3.5 cm from the nipple. Radiographic ultrasound measurements performed in December 2012 reported the tumor size to be 2*1.5*1.2 cm. A mammogram performed during this workup had noted heterogeneous breast tissue.

Examination:
Bilateral Breast and Nodal Basin (Extremity) Ultrasound
Clinical History: A 60-year-old female with newly diagnosed left-breast, invasive ductal carcinoma and DCIS, Grade 2.
Indication:
Staging.
Comparison:
None. A prior bilateral diagnostic mammogram was available for correlation. Real-time evaluation of the bilateral breasts and nodal basins were performed.
Findings:
RIGHT BREAST: No suspicious finding was seen in the right breast. No malignant-appearing axillary, infraclavicular, or internal mammary adenopathy was seen.
LEFT BREAST: At the 1 to 2 o'clock position, an irregular vascular 2×1.5×1.2 cm mass with an associated biopsy clip was compatible with the known invasive carcinoma. This was 3.5 cm from the nipple. The clip was at the superficial margin of the mass. No suspicious findings were seen in the rest of the left breast. The axillary lymph nodes had benign appearance. No infraclavicular or internal mammary adenopathy was detected.

After being referred to the oncologist, the patient began the use of one of the topical formulations described herein (standard dosing Table 11) daily on both breasts. A repeat MRI noted the dimensions to be 18×12×11, which represented a 34% reduction in tumor volume.

Comparison:
Mammograms and Ultrasound from December 2012 were examined:
The exams were of excellent technical quality.
Findings:
LEFT BREAST: The biopsy-proven cancer was identified in the left breast one o'clock position 3.5-cm from the nipple with the patient prone. The measurements of the irregularly marginated avidly enhancing steliate mass were 18 mm craniocaudal height by 12 mm, width by 11 mm AP dimension. There was metallic susceptibility artifact from a biopsy clip within the superior lateral aspect of the mass. There were no additional areas of abnormal enhancement within the left breast. The left chest wall, axilla, skin, and nipple areolar complex were unremarkable.
RIGHT BREAST: There were no areas of abnormal mass-like or nodular enhancement. No abnormal skin thickening was identified. The chest wall was intact. No axillary adenopathy was seen.

Serial thermography indicated prominent vascularity arising from the left internal thoracic (mammary) artery and crossing over the upper half of the breast ending in the tumor location. A vessel originating from the left lateral thoracic artery joined the medial branch of the left internal thoracic artery.

Area 1 measured average temperature of approximately ⅓ of the upper medial branch of the left internal thoracic artery. Area 2 measured average temperature, which included a portion of the lower ⅓ of the left internal medial branch and a lateral branch of the left lateral thoracic artery. Area 3 included the entire medial branch of the left internal and left lateral thoracic arteries which are the primary vessels supplying the tumor. Comparison of average temperatures (in ° C.) was made and calculated by both year and area location. ΔT represented the temperature difference by subtracting the area denoted in the thermogram from the temperature of the skin below the neckline (post-thoracic spine):

$$\Delta T(° C.) = Temp_{Avg.\ Area} - Temp_{Ref\ Area}$$

The reasons for using a temperature-stable skin point not affected by tumor VEGF have been explained supra. Std. Dev. was calculated in the manner as previously described.

Area 1 is exposed to the least amount of transdermal formulation as the majority is massaged into breast tissue proper. Also being located near the sternum and superior to the left breast, this section of skin occupies a point furthest from the tumor-induced release of VEGF. In addition to the reported average temperature that was used to calculate ΔT, a temperature Std. Dev. was reported. The wider the Std. Dev., the greater difference or less uniformity there is in tissue vascularity. Less uniformity would translate into thermo image sections with increased metabolism and higher MVD derived from a destabilized ECM and increased levels of growth molecules such VEGF.

Comparison of the standard deviation noted in Area 1 from a 45-day period following application of the topical formulation) revealed a 20% decline. This indicates an improved uniformity or temperatures within Area 1, as a result of transdermal cream application. Area 2 had a marked 33% decrease in Std. Dev., which was expected, since the maximum cream dose would be directed not only to the tumor, but also to the area of greatest vascularity and MVD. The ΔT change for area 2 was 0.1 in December, and declined to −0.1 in February, which parallels the change in Std. Dev. By reducing the blood flow through inhibition of VEGF, decreasing inflammatory markers, and re-stabilizing the extracellular matrix, tumor size would be expected to decrease which is confirmed by radiographic measurements.

Two cases of active breast cancer (Patients "CZ" and "CN") have been presented with similar first response to application of one particularly preferred transdermal formulation according to the present invention (see Table 11 for composition). Tumor size reduction, decline of average temperature at the tumor site, and decline in the std. temperature deviation were noted in both cases. Since the dosing of the current formulation was not tumoricidal, reduction of size would eventually be expected to plateau. Both of these cases had mammograms, which were read as heterogeneously-dense breast tissue.

These cases illustrated that the transdermal orthomolecular formulation as described herein can: a) encourage ECM stabilization; b) reduce both tumor vascularity and the MVD; and c) act as both a chemoprotective and a chemopreventative. In the case of Patient "CZ", pre-exiting tumors continued to grow until their discovery in 2011. As previously noted, the topical formulation (Table 11) did not have cytotoxic dosing capability but instead by means of matrix stabilization, restricting tumor metabolic fuel, and reducing chronic inflammation was able to halt and cause a significant reduction in tumor size. Patient "CN" had a primary, well-established tumor that initially responded to cream application, but as noted in the following discussion, more aggressive dosing of the five-family nutraceutical formulations would ultimately be required for containment. These results also demonstrated that oral supplementation's dilution factor renders it inferior to transdermals—both as a chemopreventative and as a chemoprotective. These results also verified the need for concomitant standard medical cancer treatment.

Example 10

Assessment of Isothiocyanate Stability in Long-Term Stored Formulations of Anti-Inflammatory Topical Preparations To determine the effects of aging of the topical cream formulations on the potency of the included bioactives, a study was performed as described in Table 12. Shown is a 12-month aging of the orthomolecular transdermal formulation as described in Table 11. HPLC determined concentrations based on the cream formula shown in Table 11. Bio-encapsulation of the isothiocyanates, such as cyclodextrin R-sulforaphane, is not commonly available, and can suffer instability depending on the cream base used. Since topical formulations are applied to the skin, consideration of noxious volatile sulfur emissions and dermal irritation, especially from broccoli, wasabi, and mustard extracts, limit their amount and source. Table 12 illustrates that stabilization of orthomolecular ingredients such as isothiocyanates can be accomplished in a topical formulation.

TABLE 12

| Isothiocyanate | Original Mg/gm | 4 months | 8 months | 12 months |
|---|---|---|---|---|
| 6 MITC | 0.123 | 0.341 | 0.614 | 0.571 |
| L-Sulforaphane | 0.606 | 0.358 | 1.105 | 1.841 |
| Sulforaphene | 0.551 | 1.729 | 0.308 | 0.233 |

REFERENCES

The following references, to the extent that they provide exemplary procedural or other details supplementary to those set forth herein, are specifically incorporated herein by reference:

AGER, E I, et al., "The renin-angiotensin system and malignancy," *Carcinogenesis*, 29(9):1675-1684 (2008).

ALKHALAF, M et al., "Resveratrol-induced apoptosis in human breast cancer cells is mediated primarily through the caspase-3-dependent pathway," *Arch. Med. Res.*, 39(2):162-168 (2008).

ALOSI, J A et al., "Pterostilbene inhibits breast cancer in vitro through mitochondrial depolarization and induction of caspase-dependent apoptosis," *J. Surg. Res.*, 161(2):195-201 (2010).

ALTMANN, A et al., "Coupling of boswellic acid-induced $Ca^{2+}$ mobilisation and MAPK activation to lipid metabolism and peroxide formation in human leucocytes," *Br. J. Pharmacol.*, 141(2):223-232 (2004).

AMMON, H P et al., "Mechanism of anti-inflammatory actions of curcumine and boswellic acids," *J. Ethnopharmacol.*, 38(2-3):113-119 (1993).

AMMON, H P, "Boswellic acids (components of frankincense) as the active principle in treatment of chronic inflammatory diseases," *Wien Med. Wochenschr.*, 152(15-16):373-378 (2002).

AMMON, H P, "Boswellic acids in chronic inflammatory diseases," *Planta Med.*, 72(12):1100-1116 (2006).

AMMON, H P, "Modulation of the immune system by *Boswellia serrata* extracts and boswellic acids," *Phytomedicine*, 17(11):862-867 (2010) [Erratum in: *Phytomedicine*, 18(4):334 (2011)].

ATHAR, M et al., "Multiple molecular targets of resveratrol: Anti-carcinogenic mechanisms," *Arch Biochem Biophys.* 486(2):95-102 (2009).

AZARENKO, O et al., "Suppression of microtubule dynamic instability and turnover in MCF7 breast cancer cells by sulforaphane," *Carcinogenesis*, 29(12):2360-2368 (2008).

BAKER et al., "Research on early-stage carcinogenesis: Are we approaching paradigm instability?" *J. Clin. Oncol.*, 28(20):3215-3218 (2010).

BANNING, A et al., "The GI-GPx gene is a target for Nrf2," *Mol Cell Biol.*, 25(12):4914-4923 (2005).

BRANDENBURG, L O et al., "Sulforaphane suppresses LPS-induced inflammation in primary rat microglia," *Inflamm. Res.*, 59(6):443-450 (2010).

BRANDT, K D, "Effects of non-steroidal anti-inflammatory drugs on chondrocytes metabolism in vitro and in vivo," *Am. J. Med.*, 83(5A):29-34 (1987).

BRASKY, T M et al., "Non-steroidal anti-inflammatory drug (NSAID) use and breast cancer risk in the western New York exposures and breast cancer (WEB) study," *Cancer Causes Control.*, 21(9):1503-1512 (2010).

BUKOVSKÁ, A et al., "Effects of a combination of thyme and oregano essential oils on TNBS-induced colitis in mice," *Mediators Inflamm.*, 2007:23296 (2007).

BURNETT, B P et al., "A medicinal extract of *Scutellaria baicalensis* and *Acacia catechu* acts as a dual inhibitor of cyclooxygenase and 5-lipoxygenase to reduce inflammation," *J. Med. Food.*, 10(3):442-451 (2007).

BUTT, M S and SULTAN, M T, "Green tea: nature's defense against malignancies," *Crit. Rev. Food Sci. Nutr.*, 49(5):463-473 (2009).

CALIXTO, J B et al., "Anti-inflammatory compounds of plant origin. Part II. modulation of pro-inflammatory cytokines, chemokines and adhesion molecules," *Planta Med.*, 70(2):93-103 (2004).

CHAKRABORTY, A et al., "In vitro evaluation of the cytotoxic, anti-proliferative and anti-oxidant properties of pterostilbene isolated from *Pterocarpus marsupium*," *Toxicol. In Vitro*, 24(4):1215-1228 (2010).

CHAN, M M et al., "Effects of three dietary phytochemicals from tea, rosemary and turmeric on inflammation-induced nitrite production," *Cancer Lett.*, 96(1):23-29 (1995).

CHANG C H et al., "Increased risk of stroke associated with nonsteroidal anti-inflammatory drugs: a nationwide case-crossover study," *Stroke*, 41(9):1884-1890 (2010).

CHEUNG, K L and Kong, A N, "Molecular targets of dietary phenethyl isothiocyanate and sulforaphane for cancer chemoprevention," *AAPS J.*, 12(1):87-97 (2010).

CHEUNG, K L et al., "Synergistic effect of combination of phenethyl isothiocyanate and sulforaphane or curcumin and sulforaphane in the inhibition of inflammation," *Pharm Res.*, 26(1):224-231 (2009).

CHEUNG, S and TAI, J, "Anti-proliferative and antioxidant properties of rosemary, *Rosmarinus officinalis*," *Oncol. Rep.*, 17(6):1525-1531 (2007).

CHUNG, S et al., "Regulation of SIRT1 in cellular functions: role of polyphenols," *Arch. Biochem. Biophys.*, 501(1):79-90 (2010).

CLARKE, J D et al., "Multi-targeted prevention of cancer by sulforaphane," *Cancer Lett.*, 269(2):291-304 (2008).

COOK, K L et al., "Angiotensin-(1-7) reduces fibrosis in orthotopic breast tumors," *Cancer Res.*, 70:8319-8328 (2010).

DEGNER, S C et al., "Targeting of aryl hydrocarbon receptor-mediated activation of cyclooxygenase-2 expression by the indole-3-carbinol metabolite 3,3'-diindolylmethane in breast cancer cells," *J. Nutr.*, 139(1):26-32 (2009).

DIGBY, T et al., "Effect of NQO1 induction on the antitumor activity of RH1 in human tumors in vitro and in vivo," *Cancer Chemother. Pharmacol.*, 56(3):307-316 (2005).

DOU, Q P et al., "Green tea polyphenols as a natural tumour cell proteasome inhibitor," *Inflammopharmacology*, 16(5):208-12 (2008).

DOU, Q P, "Molecular mechanisms of green tea polyphenols," *Nutr. Cancer.*, 61(6):827-835 (2009).

DULAK, J, "Nutraceuticals as anti-angiogenic agents: hopes and reality," *J. Physiol. Pharmacol.*, 56(Suppl 1):51-69 (2005).

EJAZ et al., "NSAIDs and Kidney" *J. Assoc. Physicians India*, 52:632-640 (2004).

EMERY, L A et al., "Early dysregulation of cell adhesion and extracellular matrix pathways in breast cancer progression," *Am. J. Pathol.*, 175(3):1292-1301 (2009).

FAROMBI, E O et al., "Curcumin attenuates dimethylnitrosamine-induced liver injury in rats through Nrf2-mediated induction of heme oxygenase-1," *Food Chem. Toxicol.*, 46(4):1279-1287 (2008).

FILOMENI, G et al., "trans-Resveratrol induces apoptosis in human breast cancer cells MCF-7 by the activation of MAP kinases pathways," *Genes Nutr.* 2(3):295-305 (2007).

FUKUI, M et al., "Resveratrol attenuates the anticancer efficacy of paclitaxel in human breast cancer cells in vitro and in vivo," *Eur. J. Cancer*, 46(10):1882-91 (2010).

FUNK, J L et al., "Turmeric extracts containing curcuminoids prevent experimental rheumatoid arthritis," *J. Nat. Prod.*, 69(3):351-355 (2010).

GAUTAM, R and JACHAK, S M, "Recent developments in anti-inflammatory natural products," *Med. Res. Rev.*, 29(5):767-820 (2009).

GOEL, A et al., "3-Acetyl-11-keto-β-boswellic acid loaded-polymeric nanomicelles for topical anti-inflammatory and anti-arthritic activity," *J Pharm. Pharmacol.*, 62(2):273-278 (2010).

GUPTA, I et al., "Effects of *Boswellia serrata* gum resin in patients with bronchial asthma: results of a double-blind, placebo-controlled, 6-week clinical study," *Eur. J. Med. Res.*, 3(11):511-514 (1998).

GUTIERREZ-OROZCO, F et al., "Green and black tea inhibit cytokine-induced IL-8 production and secretion in AGS gastric cancer cells via inhibition of NF-κB activity," *Planta Med.*, 76(15):1659-1665 (2010).

HARDY, M M et al., "Cyclooxygenase 2-dependent prostaglandin E2 modulates cartilage proteoglycan degradation in human osteoarthritis explants," *Arthritis Rheum.*, 46(7):1789-1803 (2002).

HARPER, C E et al., "Epigallocatechin-3-gallate suppresses early stage, but not late stage prostate cancer in TRAMP mice: mechanisms of action," *Prostate*, 67(14):1576-1589 (2007).

HAUSER, P J et al., "Sensitivity of bladder cancer cells to curcumin and its derivatives depends on the extracellular matrix," *Anticancer Res.*, 27(2):737-740 (2007).

HOJILLA, C V et al., "Metalloproteinases as common effectors of inflammation and extracellular matrix breakdown in breast cancer," *Breast Cancer Res.*, 10:205 (2008).

HOLMES, M D et al., "Aspirin intake and survival after breast cancer," *J. Clin. Oncol.*, 28(9):1467-1472 (2010).

HONG, J et al., "Modulation of arachidonic acid metabolism by curcumin and related β-diketone derivatives: effects on cytosolic phospholipase A(2), cyclooxygenases and 5-lipoxygenase," *Carcinogenesis*, 25(9):1671-1679 (2004).

HOTTA, M et al., "Carvacrol, a component of thyme oil, activates PPAR alpha and gamma and suppresses COX-2 expression," *J. Lipid Res.*, 51(1):132-139 (2010).

HSIEH, T C and Wu, J M, "Suppression of cell proliferation and gene expression by combinatorial synergy of EGCG, resveratrol and γ-tocotrienol in estrogen receptor-positive MCF-7 breast cancer cells," *Int. J. Oncol.*, 33(4):851-859 (2008).

HSU, S et al., "Green tea polyphenol induces caspase 14 in epidermal keratinocytes via MAPK pathways and reduces psoriasiform lesions in the flaky skin mouse model," *Exp. Dermatol.*, 16(8): 678-684 (2007).

HU, L et al., "Putative chemopreventive molecules can increase Nrf2-regulated cell defense in some human cancer cell lines, resulting in resistance to common cytotoxic therapies," *Cancer Chemother. Pharmacol.*, 66(3):467-474 (2010).

HUA, M et al., "Role of COX-2 in epithelial-stromal cell interactions and progression of ductal carcinoma in situ of the breast," *Proc. Natl. Acad. Sci. USA*, 106(9):3372-3377 (2009).

HUANG, G S et al., "Effects of (−)-epigallocatechin-3-gallate on cyclooxygenase 2, PGE(2), and IL-8 expression induced by IL-1β in human synovial fibroblasts," *Rheumatol. Int.*, 30(9):1197-1203 (2010).

HUANG, M T et al., "Effects of curcumin, demethoxycurcumin, bisdemethoxycurcumin and tetrahydrocurcumin on 12-O-tetradecanoylphorbol-13-acetate-induced tumor promotion," *Carcinogenesis*, 16(10):2493-2497 (1995).

HUANG, M T et al., "Inhibition of skin tumorigenesis by rosemary and its constituents carnosol and ursolic acid," *Cancer Res.*, 54(3):701-708 (1994).

HUANG, S C et al., "Carnosol inhibits the invasion of B16/F10 mouse melanoma cells by suppressing metalloproteinase-9 through down-regulating nuclear factor-κB and c-Jun," *Biochem. Pharmacol.*, 69(2):221-232 (2005).

HUEGEL, R et al., "Novel anti-inflammatory properties of the angiogenesis inhibitor vasostatin," *J. Invest. Dermatol.*, 127:65-74 (2007).

HUNAKOVA, L et al., "Modulation of markers associated with aggressive phenotype in MDA-MB-231 breast carcinoma cells by sulforaphane," *Neoplasma*, 56(6):548-556 (2009).

JACKSON, S J et al., "Sulforaphane suppresses angiogenesis and disrupts endothelial mitotic progression and microtubule polymerization," *Vascul. Pharmacol.*, 46(2):77-84 (2006).

JO, E H et al., "Efficacy of sulforaphane is mediated by p38 MAP kinase and caspase-7 activations in ER-positive and COX-2-expressed human breast cancer cells," *Eur. J. Cancer Prev.*, 16(6):505-510 (2007).

JUGE, N et al., "Molecular basis for chemoprevention by sulforaphane: a comprehensive review," *Cell. Mol. Life Sci.*, 64(9):1105-1127 (2007).

JURENKA, J S, "Anti-inflammatory properties of curcumin, a major constituent of *Curcuma longa*: a review of preclinical and clinical research," *Altern. Med. Rev.*, 14(2):141-153 (2009) [Erratum in *Altern. Med. Rev.*, 14(3):277 (2009).

KAOULLA, N et al., "Investigation of *Brassica oleracea* and *Nasturtium officinale* seeds for the presence of epithiospecifier protein," *J. Phytochem.*, 19(6):1053-1056 (1980).

KIM, H A et al., "Phase 2 enzyme inducer sulphoraphane blocks matrix metalloproteinase production in articular chondrocytes," *Rheumatology*, 48(8):932-938 (2009).

KIM, J E et al., "LYR71, a derivative of trimeric resveratrol, inhibits tumorigenesis by blocking STAT3-mediated matrix metalloproteinase 9 expression," *Exp. Mol. Med.*, 40(5):514-522 (2008).

KOBAYASHI, Y et al., "Possible involvement of matrix metalloproteinase-9 in Langerhans cell migration and maturation," *J. Immunol.*, 163(11):5989-5993 (1999).

KOEBERLE, A et al., "Green tea epigallocatechin-3-gallate inhibits microsomal prostaglandin E(2) synthase-1," *Biochem. Biophys. Res. Commun.*, 388(2):350-354 (2009).

KOLATA, G, "Old ideas spur new approaches in cancer fight," *N.Y. Times* (Dec. 29, 2009).

KWON, S J et al., "Unnatural polyketide analogues selectively target the HER signaling pathway in human breast cancer cells," *Chembiochem.*, 11(4):573-580 (2010).

LAPPANO, R et al., "Structure-activity relationships of resveratrol and derivatives in breast cancer cells," *Mol. Nutr. Food Res.*, 53(7):845-858 (2009).

LASZCZYK, M N, "Pentacyclic triterpenes of the lupane, oleanane, and ursane group as tools in cancer therapy," *Planta Med.*, 75(15):1549-1560 (2009).

LE CORRE, L et al., "Resveratrol and breast cancer chemoprevention: molecular mechanisms," *Mol. Nutr. Food Res.*, 49(5):462-471 (2005).

LI, Y et al., "Sulforaphane, a dietary component of broccoli/broccoli sprouts, inhibits breast cancer stem cells," *Clin. Cancer Res.*, 16(9):2580-2590 (2010).

LIM, C B et al., "*Curcuma wenyujin* extract induces apoptosis and inhibits proliferation of human cervical cancer cells in vitro and in vivo," *Integr. Cancer Ther.*, 9(1):36-49 (2010).

LIN, J K and LIN-SHIAU, S Y, "Mechanisms of cancer chemoprevention by curcumin." *Proc. Natl. Sci. Counc. Repub. China B.*, 25(2):59-66 (2001).

LIN, J K et al., "Recent studies on the biofunctions and biotransformations of curcumin," *Biofactors*, 13(I-4): 153-158 (2000).

LIN, J K, "Suppression of protein kinase C and nuclear oncogene expression as possible action mechanisms of cancer chemoprevention by curcumin," *Arch. Pharm. Res.*, 27(7):683-692 (2004).

LIN, J N et al., "Resveratrol modulates tumor cell proliferation and protein translation via SIRT1-dependent AMPK activation," *J. Agric. Food Chem.*, 58(3):1584-1592 (2010).

LIU, D et al., "Piceatannol inhibits phorbol ester-induced NF-κB activation and COX-2 expression in cultured human mammary epithelial cells," *Nutr. Cancer*, 61(6): 855-863 (2009).

LIU, J J et al., "Boswellic acids trigger apoptosis via a pathway dependent on caspase-8 activation but independent on Fas/Fas ligand interaction in colon cancer HT-29 cells," *Carcinogenesis*, 23(12):2087-2093 (2002).

LIU, J J et al., "Keto- and acetyl-keto-boswellic acids inhibit proliferation and induce apoptosis in Hep G2 cells via a caspase-8 dependent pathway," *Int. J. Mol. Med.*, 10(4): 501-505 (2002).

LO, A H et al., "Carnosol, an antioxidant in rosemary, suppresses inducible nitric oxide synthase through down-regulating nuclear factor-κB in mouse macrophages," *Carcinogenesis*, 23(6):983-991 (2002).

LU, F et al., "Resveratrol prevents estrogen-DNA adduct formation and neoplastic transformation in MCF-10F cells," *Cancer Prev. Res. (Phila)*, 1(2):135-145 (2008).

MAGDALENA, A et al., "Microenvironmental influences that drive progression from benign breast disease to invasive breast cancer," *J. Mammary Gland Biol. Neoplasia*, 15:389-397 (2010).

MALLER, O et al., "Extracellular matrix composition reveals complex and dynamic stromal-epithelial interactions in the mammary gland," *J. Mammary Gland Biol. Neoplasia*, 15(3):301-318 (2010).

MANSON, M M et al., "Innovative agents in cancer prevention," Recent Results Cancer Res., 166:257-275 (2005).

MARKS et al., "Tumor promotion as a target of cancer prevention," Recent Results Cancer Res., 174:37-47 (2007).

MATIĆ, I et al., "Cytotoxic effect of wine polyphenolic extracts and resveratrol against human carcinoma cells and normal peripheral blood mononuclear cells," J. Med. Food, 13(4):851-862 (2010).

MCCORMACK, D and MCFADDEN, D, "A review of pterostilbene antioxidant activity and disease modification," Oxidative Med. Cell. Longevity, 2013:575482 (2013).

MIKSITS, M et al., "Antitumor activity of resveratrol and its sulfated metabolites against human breast cancer cells," Planta Med., 75(11):1227-1230 (2009).

MÜHLBAUER, R C et al., "Common herbs, essential oils, and monoterpenes potently modulate bone metabolism," Bone, 32(4):372-380 (2003).

MUKERJEE, A and VISHWANATHA, J, "Formulation, characterization and evaluation of curcumin-loaded PLGA nanospheres for cancer therapy," Anticancer Res., 29(10):3867-3875 (2009).

MURAKAMI, Y et al., "Comparative anti-inflammatory activities of curcumin and tetrahydrocurcumin based on the phenolic O—H bond dissociation enthalpy, ionization potential and quantum chemical descriptor," Anticancer Res., 28(2A):699-707 (2008).

MURIAS, M et al., "Cytotoxic activity of 3,3',4,4',5,5'-hexahydroxystilbene against breast cancer cells is mediated by induction of p53 and downregulation of mitochondrial superoxide dismutase," Toxicol. In Vitro, 22(5): 1361-1370 (2008).

MURIAS, M et al., "Metabolism of resveratrol in breast cancer cell lines: impact of sulfotransferase 1A1 expression on cell growth inhibition," Cancer Lett., 261(2):172-182 (2008).

MYZAK, M C and DASHWOOD, R H, "Chemoprotection by sulforaphane: keep one eye beyond Keap1," Cancer Lett., 233(2):208-218 (2006).

NAGAI, M et al., "The effect of isosaponarin isolated from wasabi leaf on collagen synthesis in human fibroblasts and its underlying mechanism," J. Nat. Med., 64(3):305-312 (2010).

NAKAMURA, Y et al., "Inhibitory effects of curcumin and tetrahydrocurcuminoids on the tumor promoter-induced reactive oxygen species generation in leukocytes in vitro and in vivo," Jpn. J. Cancer Res., 89(4):361-370 (1998).

NAVARRO-PERÁN, E et al., "The anti-inflammatory and anti-cancer properties of epigallocatechin-3-gallate are mediated by folate cycle disruption, adenosine release and NF-κB suppression," Inflamm. Res., 57(10):472-478 (2008).

NGUYEN, T H et al., "ERK1/2 activation is required for resveratrol-induced apoptosis in MDA-MB-231 cells," Int. J. Oncol., 33(1):81-92 (2008).

NIAN, H et al., "Modulation of histone deacetylase activity by dietary isothiocyanates and allyl sulfides: studies with sulforaphane and garlic organosulfur compounds," Environ. Mol. Mutagen., 50(3):213-221 (2009).

NIEDERBERGER, E and GEISSLINGER, G, "The IKK-NF-κB pathway: a source for novel molecular drug targets in pain therapy?" FASEB J., 22:3432-3442 (2008).

NISHIDA, M et al., "Monoacetylcurcumin strongly regulates inflammatory responses through inhibition of NF-κB activation," Int. J. Mol. Med., 25(5):761-767 (2010).

NOMURA, T et al., "Selective sensitivity to wasabi-derived 6-(methylsulfinyl)hexyl isothiocyanate of human breast cancer and melanoma cell lines studied in vitro," Cancer Detect. Prev., 29(2): 155-160 (2005).

NOONAN, D M et al., "Angiogenesis and cancer prevention: a vision," Recent Results Cancer Res., 174:219-224 (2007).

O'BYRNE, K J and DALGLEISH, A G, "Chronic immune activation and inflammation as the cause of malignancy," Brit. J. Cancer, 85(4):473-483 (2001).

OLESKI A et al., "Screening of selected Arabian medicinal plant extracts for inhibitory activity against peptidases," Pharmazie, 61(4):359-361 (2006).

PAN, M H et al., "Comparative studies on the suppression of nitric oxide synthase by curcumin and its hydrogenated metabolites through down-regulation of IκB kinase and NFκB activation in macrophages," Biochem. Pharmacol., 60(11):1665-1676 (2000).

PAN, M H et al., "Suppression of heregulin-β1/HER2-modulated invasive and aggressive phenotype of breast carcinoma by pterostilbene via inhibition of matrix metalloproteinase-9, p38 kinase cascade and Akt activation," Evid.-Based Complement. Alternat. Med., 2011:562187 (2011).

PATTACINI, L et al., "Angiotensin II protects fibroblast-like synoviocytes from apoptosis via the AT1-NF-B pathway," Rheumatology, 46:1252-1257 (2007).

PAUR, I et al., "Extract of oregano, coffee, thyme, clove, and walnuts inhibits NF-kappaB in monocytes and in transgenic reporter mice," Cancer Prev. Res. (Phila), 3(5):653-663 (2010).

PAVLAKIS, K et al., "The assessment of angiogenesis and fibroblastic stromagenesis in hyperplastic and pre-invasive breast lesions," BMC Cancer, 8:88 (2008).

PEAIRS, A et al., "Epigallocatechin-3-gallate (EGCG) attenuates inflammation in MRL/lpr mouse mesangial cells," Cell Mol. Immunol., 7(2):123-132 (2010).

PENG, C H et al., "Supercritical fluid extracts of rosemary leaves exhibit potent anti-inflammation and anti-tumor effects," Biosci. Biotechnol. Biochem., 71(9):2223-2232 (2007).

PERRONE, E et al., "COX-2 expression in DCIS: correlation with VEGF, HER-2/neu, prognostic molecular markers and clinicopathological features," Histopathol., 46(5): 561-568 (2005).

PEZZATO, E et al., "Proteinase-3 directly activates MMP-2 and degrades gelatin and Matrigel; differential inhibition by (−)epigallocatechin-3-gallate," J. Leukoc. Biol., 74(1): 88-94 (2003).

PIASTOWSKA-CIESIELSKA, A W et al., "Angiotensin modulates human mammary epithelial cell motility," J. Renin-Angiotensin Aldosterone Syst., 15(4):419-429 (December 2014).

PLEDGIE-TRACY, A et al., "Sulforaphane induces cell type-specific apoptosis in human breast cancer cell lines," Mol. Cancer Ther., 6(3):1013-1021 (2007).

POECKEL, D et al., "3-O-acetyl-11-keto-boswellic acid decreases basal intracellular $Ca2+$ levels and inhibits agonist-induced $Ca^{2+}$ mobilization and mitogen-activated protein kinase activation in human monocytic cells," J. Pharmacol. Exp. Ther., 316(1):224-232 (2005).

POECKEL, D et al., "Boswellic acids stimulate arachidonic acid release and 12-lipoxygenase activity in human platelets independent of $Ca^{2+}$ and differentially interact with platelet-type 12-lipoxygenase," Mol. Pharmacol., 70(3): 1071-1078 (2006).

PUDDEFOOT, J R et al., "The role of angiotensin II in the regulation of breast cancer cell adhesion and invasion," *Endocrine-Related Cancer*, 13:895-903 (2006).

RAMIREZ, M C and SINGLETARY, K, "Regulation of estrogen receptor alpha expression in human breast cancer cells by sulforaphane," *J. Nutr. Biochem.*, 20(3):195-201 (2009).

RAN, Z H et al., "Epigallocatechin-3-gallate ameliorates rats colitis induced by acetic acid," *Biomed. Pharmacother.*, 62(3):189-196 (2008).

RECAREANU, F et al., "Current research on breast carcinogenesis," *Curr. Health Sci. J.*, 36(1):5-7 (2010).

RODRIGUES-FERREIRA, S et al., "Angiotensin II facilitates breast cancer cell migration and metastasis," *PLoS ONE*, 7(4):35667 (2012).

ROSE, P et al., "Broccoli and watercress suppress matrix metalloproteinase-9 activity and invasiveness of human MDA-MB-231 breast cancer cells." *Toxicol. Appl. Pharmacol.*, 209(2): 105-113 (2005).

ROY, P et al., "Inhibitory effects of tea polyphenols by targeting cyclooxygenase-2 through regulation of nuclear factor κB, Akt and p53 in rat mammary tumors," *Invest. New Drugs*, 29(2):225-231 (2011).

ROY, S et al., "Human genome screen to identify the genetic basis of the anti-inflammatory effects of *Boswellia* in microvascular endothelial cells," *DNA Cell Biol.*, 24(4): 244-255 (2005).

RÜEGG, C et al., "Endothelial cell integrins and COX-2: mediators and therapeutic targets of tumor angiogenesis," *Biochim. Biophys. Acta*, 1654(1):51-67 (2004).

SANDUR, S K et al., "Curcumin, demethoxycurcumin, bisdemethoxycurcumin, tetrahydrocurcumin and turmerones differentially regulate anti-inflammatory and antiproliferative responses through a ROS-independent mechanism," *Carcinogenesis*, 28(8):1765-1773 (2007).

SCARLATTI, F et al., "Role of non-canonical beclin 1-independent autophagy in cell death induced by resveratrol in human breast cancer cells," *Cell Death Differ.*, 15(8): 1318-1329 (2008).

SCHECKEL, K A et al., "Rosmarinic acid antagonizes activator protein-1-dependent activation of cyclooxygenase-2 expression in human cancer and nonmalignant cell lines," *J. Nutr.*, 138(11):2098-2105 (2008).

SEN, T et al., "Epigallocatechin-3-gallate (EGCG) downregulates gelatinase-B (MMP-9) by involvement of FAK/ERK/NFκB and AP-1 in the human breast cancer cell line MDA-MB-231," *Anticancer Drugs*, 21(6): 632-644 (2010).

SHAN, D et al., "EGCG reducing the susceptibility to cholesterol gallstone formation through the regulation of inflammation," *Biomed. Pharmacother.*, 62(10):677-83 (2008).

SHANNON, J et al., "Sulforaphane supplementation in women newly diagnosed with DCIS: A biomarker study," *J. Clin. Oncol.*, 28:15s (Suppl; Abstr TPS143) (2010).

SIEMONEIT, U et al., "Identification and functional analysis of cyclooxygenase-1 as a molecular target of boswellic acids," *Biochem. Pharmacol.*, 75(2):503-513 (2008).

SIEMONEIT, U et al., "Inhibition of microsomal prostaglandin E2 synthase-1 as a molecular basis for the anti-inflammatory actions of Boswellic acids from frankincense," *Br. J. Pharmacol.*, 162(1):147-162 (2011).

SINGH, S et al., "Boswellic acids and glucosamine show synergistic effect in preclinical anti-inflammatory study in rats," *Bioorg. Med. Chem. Lett.*, 17(13):3706-3711 (2007).

SINGH, S et al., "Boswellic acids: A leukotriene inhibitor also effective through topical application in inflammatory disorders," *Phytomedicine*, 15(6-7):400-407 (2008).

SINGH, S K et al., "Effect of acetyl 11-keto β-boswellic acid on metastatic growth factor responsible for angiogenesis," *Vascul. Pharmacol.*, 46(5):333-337 (2007).

SINGH, S K et al., "Precursor IGF-II (proIGF-II) and mature IGF-II (mIGF-II) induce Bcl-2 and Bcl-X L expression through different signaling pathways in breast cancer cells," *Growth Factors*, 26(2):92-103 (2008).

SKUPINSKA, K et al., "The effect of isothiocyanates on CYP1A1 and CYP1A2 activities induced by polycyclic aromatic hydrocarbons in Mcf7 cells," *Toxicol. In Vitro*, 23(5):763-771 (2009).

SNYDER, R M et al., "Vitamin E analog α-TEA, methylseleninic acid, and trans-resveratrol in combination synergistically inhibit human breast cancer cell growth," *Nutr. Cancer*, 60(3):401-411 (2008).

SOBOLEWSKI, C et al., "The role of cyclooxygenase-2 in cell proliferation and cell death in human malignancies," *Int. J. Cell Biol.*, 2010:215158 (2010).

SONNENSCHEIN, C and SOTO, A M, "Theories of carcinogenesis: an emerging perspective," *Semin. Cancer Biol.*, 18(5):372-377 (2008).

STEFANSKA, B et al., "Hypomethylation and induction of retinoic acid receptor beta 2 by concurrent action of adenosine analogues and natural compounds in breast cancer cells," *Eur. J. Pharmacol.*, 638(1-3):47-53 (2010).

STONER, G D and MUKHTAR, H, "Polyphenols as cancer chemopreventive agents," *J. Cell Biochem.*, 22:169-180 (Suppl.) (1995).

SUBBARAMAIAH, K et al., "Resveratrol inhibits cyclooxygenase-2 transcription and activity in phorbol ester-treated human mammary epithelial cells," *J. Biol. Chem.*, 273(34):21875-21882 (1998).

SUN, X Y et al., "Potential anti-cancer activities of furanodiene, a sesquiterpene from *Curcuma wenyujin*," *Am. J. Chin. Med.*, 37(3):589-596 (2009).

SUNAGAWA, Y et al., "A natural p300-specific histone acetyltransferase inhibitor, curcumin, in Addition to angiotensin-converting enzyme inhibitor, exerts beneficial effects on left ventricular systolic function after myocardial infarction in rats," *Circ. J.*, 75(9):2151-2159 (2011).

SYROVETS, T et al., "Inhibition of IκB kinase activity by acetyl-boswellic acids promotes apoptosis in androgen-independent PC-3 prostate cancer cells in vitro and in vivo," *J. Biol. Chem.*, 280(7):6170-6180 (2005).

TAHMASEBI, M et al., "Localisation of renin-angiotensin system (RAS) components in breast," *Brit. J. Cancer*, 95:67-74 (2006).

TAKAKI, I et al., "Anti-inflammatory and antinociceptive effects of *Rosmarinus officinalis* L. essential oil in experimental animal models," *J. Med. Food*, 11(4):741-746 (2008).

TANG, F Y et al., "Resveratrol inhibits migration and invasion of human breast-cancer cells," *Mol. Nutr. Food Res.*, 52(6):683-691 (2008).

TELANG, U et al., "Comparison of the effects of phenethyl isothiocyanate and sulforaphane on gene expression in breast cancer and normal mammary epithelial cells," *Exp. Biol. Med. (Maywood)*, 234(3):287-295 (2009).

TRAN, P L et al., "Epigallocatechin-3-gallate suppresses the expression of HSP70 and HSP90 and exhibits anti-tumor activity in vitro and in vivo," *BMC Cancer*, 10:276 (2010).

TROMPEZINSKI, S et al., "*Gingko biloba* extract reduces VEGF and CXCL-8/IL-8 levels in keratinocytes with cumulative effect with epigallocatechin-3-gallate," *Arch. Dermatol. Res.*, 302(3):183-189 (2010).

TSENG, E et al., "Dietary organic isothiocyanates are cytotoxic in human breast cancer MCF-7 and mammary epithelial MCF-12A cell lines," *Exp. Biol. Med. (Maywood)*, 229(8):835-842 (2004).

UTO, T et al., "Effects of 6-(methylsulfinyl)hexyl isothiocyanate on cyclooxygenase-2 expression induced by lipopolysaccharide, interferon-gamma and 12-O-tetradecanoylphorbol-13-acetate," *Oncol. Rep.*, 17(1):233-238 (2007).

UTO, T et al., "Inhibition of lipopolysaccharide-induced cyclooxygenase-2 transcription by 6-(methylsulfinyl) hexyl isothiocyanate, a chemopreventive compound from *Wasabia japonica* (Miq.) Matsumura, in mouse macrophages," *Biochem. Pharmacol.*, 70(12): 1772-1784 (2005).

VAN DEN BERG, W B, "Osteoarthritis year 2010 in review: pathomechanisms," *Osteoarth. Cartil.*, 19(4): 338-341 (2011).

VAN DER VEEN, J W et al., "Keratinocytes, innate immunity and allergic contact dermatitis—opportunities for the development of in vitro assays to predict the sensitizing potential of chemicals," in *Contact Dermatitis*, Dr. Young Suck Ro (Ed.), pp. 39-57, ISBN: 978-953-307-577-578, InTech.

VARKI, A et al., (Eds), *Essentials of Glycobiology*, Cold Spring Harbor Laboratory Press, Cold Spring Harbor, N.Y. (1999).

VINSON, G P et al., "The renin-angiotensin system in the breast and breast cancer," *Endocrine-Related Cancer*, 19:R1-R19 (2012).

WANG, C-J et al., "(−)-epigallocatechin gallate inhibits endothelin-1-induced C-reactive protein production in vascular smooth muscle cells," *Basic Clin. Pharmacol. Toxicol.*, 107(2):669-675 (2010).

WANG, H et al., "Targeting NF-kappa B with a natural triterpenoid alleviates skin inflammation in a mouse model of psoriasis," *J. Immunol.*, 183(7):4755-4763 (2009).

WANG, R-H et al., "Interplay among BRCA1, SIRT1, and Survivin during BRCA1-associated tumorigenesis," *Molec. Cell*, 32(1):11-20 (2008).

WANG, W et al., "Sulforaphane, erucin, and iberin up-regulate thioredoxin reductase 1 expression in human MCF-7 cells." *J. Agric. Food Chem.*, 53(5):1417-1421 (2005).

WATANABE, M et al., "Identification of 6-methylsulfinyl-hexyl isothiocyanate as an apoptosis-inducing component in wasabi," *Phytochemistry*, 62(5):733-739 (2003).

WEAVER, V M et al., "The importance of the microenvironment in breast cancer progression: recapitulation of mammary tumorigenesis using a unique human mammary epithelial cell model and a three-dimensional culture assay," *Biochem. Cell Biol.*, 74(6): 833-851 (1996).

WEBB, E F et al., "Intralesional cytokines in chronic oxazolone-induced contact sensitivity suggest roles for tumor necrosis factor α and interleukin-4," *J. Invest. Dermatol.*, 111(1):86-92 (1998).

WEIL, M J et al., "Tumor cell proliferation and cyclooxygenase inhibitory constituents in horseradish (*Armorica rusticana*) and Wasabi (*Wasabia japonica*)," *J. Agric. Food Chem.*, 53(5): 1440-1444 (2005).

WIDLANSKY, M E et al., "Acute EGCG supplementation reverses endothelial dysfunction in patients with coronary artery disease," *J. Am. Coll. Nutr.*, 26(2):95-102 (2007).

WOO, K J and KWON, T K. "Sulforaphane suppresses lipopolysaccharide-induced cyclooxygenase-2 (COX-2) expression through the modulation of multiple targets in COX-2 gene promoter," *Int. Immunopharmacol.*, 7(13): 1776-1783 (2007).

XIAO, Y et al., "Furanodiene induces G2/M cell cycle arrest and apoptosis through MAPK signaling and mitochondria-caspase pathway in human hepatocellular carcinoma cells," *Cancer Biol. Ther.*, 6(7):1044-1050 (2007).

YAMAKUCHI, M et al., "Epigallocatechin gallate inhibits endothelial exocytosis," *Biol. Chem.*, 389(7):935-941 (2008).

YASUMARU, M et al., "Inhibition of angiotensin II activity enhanced the antitumor effect of cyclooxygenase-2 inhibitors via insulin-like growth factor I receptor pathway," *Cancer Res.*, 63:6726-6734 (2003).

YESIL-CELIKTAS, O et al., "Inhibitory effects of rosemary extracts, carnosic acid and rosmarinic acid on the growth of various human cancer cell lines," *Plant Foods Hum. Nutr.*, 65(2):158-163 (2010).

YODKEEREE, S et al., "Tetrahydrocurcumin inhibits HT1080 cell migration and invasion via downregulation of MMPs and uPA," *Acta Pharmacol. Sin.*, 29(7):853-860 (2008).

YOSHINO, K et al., "Preventive effects of (−)-epigallocatechin-3-O-gallate on mouse type IV allergy induced by oxazolone and its antiinflammatory activities," *J. Technol. Education*, 17(2):57-65 (2010).

YOUN, H S et al., "Sulforaphane suppresses oligomerization of TLR4 in a thiol-dependent manner," *J. Immunol.*, 184(1):411-419 (2010).

YOYSUNGNOEN, P et al., "Anti-cancer and anti-angiogenic effects of curcumin and tetrahydrocurcumin on implanted hepatocellular carcinoma in nude mice," *World J. Gastroenterol.*, 14(13):2003-2009 (2008).

ZAKKAR, M et al., "Activation of Nrf2 in endothelial cells protects arteries from exhibiting a proinflammatory state," *Arterioscler. Thromb. Vasc. Biol.*, 29(11):1851-1857 (2009).

ZHANG, D D et al., "Keap1 is a redox-regulated substrate adaptor protein for a Cul3-dependent ubiquitin ligase complex," *Mol. Cell Biol.*, 24(24):10941-10953 (2004).

ZHANG, Y and CALLAWAY, E C, "High cellular accumulation of sulphoraphane, a dietary anticarcinogen, is followed by rapid transporter-mediated export as a glutathione conjugate," *Biochem. J.*, 364(Pt 1):301-307 (2002).

ZU, Y et al., "Activities of ten essential oils towards *Propionibacterium acnes* and PC-3, A-549 and MCF-7 cancer cells," *Molecules*, 15(5):3200-3210 (2010).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are specifically incorporated herein by reference to the same extent as if each reference was individually and specifically indicated to be incorporated by reference, and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising," "having," "including," or "containing," with reference to an element or elements is intended to provide support for a similar aspect or embodiment of the invention that "consists of," "consists essentially of," or "substantially comprises" the particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of ordinary skill in the art that variations may be applied to the compositions and methods and in the steps or in the sequence of steps of the method described herein without departing from the concept, spirit and scope of the invention. More specifically, it will be apparent that certain agents that are chemically- or physiologically-related may be substituted for the agents described herein while the same or similar results would be achieved. All such similar substitutes and modifications apparent to those ordinarily skilled in the art are deemed to be within the spirit, scope, and concept of the invention as defined by the appended claims.

What is claimed is:

1. A method for reducing inflammation in a mammalian tissue, or ameliorating at least one symptom thereof, the method comprising: directly administering to the mammalian tissue, an effective amount of an aqueous composition comprising a) one or more catechins, catechin derivatives, or catechin analogs, agonists, or antagonists thereof; b) one or more curcuminoids, curcuminoid derivatives, or curcuminoid analogs, agonists, or antagonists thereof; c) one or more isothiocyanates, isothiocyanate derivatives, or isothiocyanate analogs, agonists, or antagonists thereof; d) one or more stilbenoids, stilbenoid derivatives, or stilbenoid analogs, agonists, or antagonists thereof; e) at least one therapeutic essential oil; f) tetrahydropiperine; and g) at least one compound selected from the group consisting of broccoli seed oil, mustard seed oil, wintercress oil, watercress oil, wintercress seed, watercress seed, and broccoli seed powder, for a time sufficient to reduce inflammation in the mammalian tissue, or to ameliorate the at least one symptom thereof.

2. The method of claim 1, wherein the at least one symptom thereof includes pain, swelling, redness, edema, aching, tenderness, soreness, or any combination thereof.

3. The method of claim 1, wherein the inflammation is caused by, results in, or contributes to, injury, strain, sprain, trauma, soreness, ache, fatigue, cancer, prostatitis, infection, or any combination thereof, in an affected mammal.

4. The method of claim 1, wherein the composition is formulated as an emollient; a cream; an ointment; a lotion; a gel; a salve; a controlled-release matrix; a suppository; a transdermal delivery system; a liposomal or a lipid particle preparation; a microcapsule; a nanocapsules; or any combination thereof.

5. The method of claim 1, wherein the mammalian tissue is comprised within a human.

6. The method of claim 5, wherein the human exhibits one or more indicia of a disease, a disorder, or a dysfunction that is selected from the group consisting of a pre-menstrual pain, a mammary gland inflammation, a fibroid cyst, a lipid cyst, a post-menopausal estrogen insufficiency; a cyclic mastalgia, a benign breast pain, a premenstrual breast pain, a breast tenderness, ache or swelling, a fibrocystic disease or disorder, a mammary nodule or cyst, a fibroadenoma, a mammary carcinoma, a vascular or a neuropathic complication of diabetes, an impairment of fertility, a low production of breast milk, an elevated blood pressure, a restriction of blood flow in the vasculature or microvasculature of an adipose tissue, a menopausal hot flash, a skin or mucous membrane complication of Sjogren's autoimmune syndrome, rosacea, psoriasis, eczema, actinic keratosis, a dermal or peripheral neuropathic complication of shingles, and any combination thereof.

7. The method of claim 1, wherein the mammalian tissue comprises human prostate tissue, human breast tissue, human muscle tissue, or human joint tissue.

8. The method of claim 1, wherein the composition is administered to the mammalian tissue in one or more daily doses, each in an amount from about 0.1 cc to about 5 cc.

9. The method of claim 1, wherein the composition is administered to the mammalian tissue substantially for a period of about 21 to about 90 days.

10. The method of claim 1, wherein the effectiveness of the composition is quantitated, measured, or monitored by thermography, or by comparison of two or more thermographic images of a first tissue of the mammal, at least one of which images is taken pre-treatment, and at least one of which images is obtained either during- or post-treatment.

11. The method of claim 1, wherein the aqueous composition further comprises one or more cyclodextrins, lipophilic bases, liposomal formulations, polyacrylamide based emulsions, rheology modifiers, transdermal compounding bases or gels, lipoic acid, xanthan gums, cetearyl alcohol, ceteareth-20, isopropyl palmitate, isopropyl myristate, preservatives, or any combination thereof.

12. The method of claim 1, wherein the aqueous composition further comprises a compound selected from the group consisting of one or more vitamins, N-methyl-2-pyrrolidone, melatonin, and combinations thereof.

13. The method of claim 12, wherein the one or more vitamins is selected from the group consisting of cholecalciferol, α-tocopherol, β-tocopherol, δ-tocopherol, γ-tocopherol, α-tocotrienol, β-tocotrienol, δ-tocotrienol, γ-tocotrienol, and combinations thereof.

14. The method of claim 1, wherein the one or more catechins is epigallocatechin gallatyl glucoside, or wherein the one or more stilbenoids is selected from the group consisting of 3,5,4'-trihydroxy-trans-stilbene, 4-[(E)-2-(3,5-dimethoxyphenyl)ethenyl]phenol, and combinations thereof.

15. The method of claim 1, wherein the one or more curcuminoids is selected from the group consisting of curcumin, tetrahydrocurcumin, tetrahydrocurcuminoid, tetrahydrodiferuloylmethane, tetrahydro-demethoxydiferuloylmethane, tetrahydrobis-demethoxydiferuloylmethane, and combinations thereof.

16. The method of claim 1, wherein the one or more isothiocyanates is selected from the group consisting of R-sulforaphane, L-sulforaphane, sulforaphene, β-phenylethyl isothiocyanate, 7-methylsulfinylheptyl isothiocyanate, 8-methylsulfinyloctyl isothiocyanate, benzyl isothiocyanate, 6-(methylsulfinyl)hexyl isothiocyanate, tetrahydrodiferuloylmethane, broccoli seed oil, daikon oil, broccoli seed powder, mustard seed oil, and combinations thereof.

17. The method of claim 1, wherein the at least one essential oil is rosemary essential oil, birch essential oil, balsam fir essential oil, peppermint essential oil, marjoram essential oil, helichrysum essential oil, thyme essential oil, frankincense essential, clove essential oil, turmeric essential oil, orange essential oil, or any combination thereof.

18. The method of claim 1, wherein:
   a) the one or more catechins is each present in the composition in an amount from about 0.0000001% to about 25%, by weight;
   b) the one or more curcuminoids is each present in the composition in an amount from about 0.0000001% to about 25%, by weight;
   c) the one or more isothiocyanates is each present in the composition in an amount from about 0.0000001% to about 25%, by weight;
   d) the one or more stilbenoids is each present in the composition in an amount from about 0.0000001% to about 25%, by weight;
   e) the at least one essential oil is present in the composition in an amount from 0.0003% to about 50%, by weight;
   f) the tetrahydropiperine is present in the composition in an amount from about 0.01% to about 1%, by weight; and
   g) the at least one compound is present in an amount from about 0.01% to about 1%, by weight.

19. The method of claim 18, wherein
   a) the one or more catechins is each present in the composition in an amount from about 0.00001% to about 2.5%, by weight;
   b) the one or more curcuminoids is each present in the composition in an amount from about 0.00001% to about 2.5%, by weight;
   c) the one or more isothiocyanates is each present in the composition in an amount from about 0.00001% to about 2.5%, by weight;
   d) the one or more stilbenoids is each present in the composition in an amount from about 0.00001% to about 2.5%, by weight;
   e) the at least one essential oil is present in the composition in an amount from about 0.003% to about 5%, by weight;
   f) the tetrahydropiperine is present in the composition in an amount from about 0.01% to about 1%, by weight; and
   g) the broccoli seed oil, the mustard seed oil, the wintercress oil, the watercress oil, the wintercress seed, the watercress seed, and the broccoli seed powder are each present in an amount from about 0.01% to about 1%, by weight.

20. The method of claim 19, wherein
   a) the one or more catechins is each present in the composition in an amount from about 0.01% to about 0.5%, by weight;
   b) the one or more curcuminoids is each present in the composition in an amount from about 0.01% to about 0.5%, by weight;
   c) the one or more isothiocyanates is each present in the composition in an amount from about 0.01% to about 0.5%, by weight;
   d) the one or more stilbenoids is each present in the composition in an amount from about 0.01% to about 0.5%, by weight;
   e) the at least one essential oil is present in the composition in an amount from about 0.01% to about 0.9%, by weight;
   f) the tetrahydropiperine is present in the composition in an amount from about 0.001% to about 1%, by weight; and
   g) the broccoli seed oil, the mustard seed oil, the wintercress oil, the watercress oil, the wintercress seed, the watercress seed, and the broccoli seed powder are each present in an amount from about 0.01% to about 0.1%, by weight.

21. The method of claim 20, wherein
   a) the one or more catechins is each present in the composition in an amount of about 0.10% to about 0.30% by weight;
   b) the one or more curcuminoids is each present in the composition in an amount of about 0.15% to about 0.35%, by weight;
   c) the one or more isothiocyanates is each present in the composition in an amount of about 0.3 to about 2%, by weight;
   d) the one or more stilbenoids is each present in the composition in an amount of about 0.8% to about 1.2%, by weight;
   e) the at least one essential oil is present in the composition in an amount of about 0.3% to about 0.5%, by weight;
   f) the tetrahydropiperine is present in the composition in an amount from about 0.01% to about 1%, by weight; and
   g) the broccoli seed oil, the mustard seed oil, the wintercress oil, the watercress oil, the wintercress seed, the watercress seed, and the broccoli seed powder are each present in an amount from about 0.01% to about 1%, by weight.

22. The method of claim 1, wherein the aqueous composition further comprises a compound selected from the group consisting of isopropyl palmitate, isopropyl myristate, vitamin $D_3$, vitamin E, 3'3-diindolylmethane, and any combination thereof.

23. A method for treating, or ameliorating one or more symptoms of breast microcalcification, extracellular matrix (ECM) damage, ductal carcinoma in situ (DCIS), carcinoma in situ (CIS), a neoplastic disorder, a trauma, or an injury in a mammal, comprising, providing to the breast tissue of a mammal in need thereof, an effective amount of an aqueous composition comprising a) one or more catechins, catechin derivatives, or catechin analogs, agonists, or antagonists thereof; b) one or more curcuminoids, curcuminoid derivatives, or curcuminoid analogs, agonists, or antagonists thereof; c) one or more isothiocyanates, isothiocyanate derivatives, or isothiocyanate analogs, agonists, or antagonists thereof; d) one or more stilbenoids, stilbenoid derivatives, or stilbenoid analogs, agonists, or antagonists thereof; e) at least one therapeutic essential oil; f) tetrahydropiperine; and g) at least one compound selected from the group consisting of broccoli seed oil, mustard seed oil, wintercress oil, watercress oil, wintercress seed, watercress seed, and broccoli seed powder, for a time sufficient to treat, or ameliorate the one or more symptoms of the breast microcalcification, the ECM damage, the DCIS, the CIS, the neoplastic disorder, the trauma, or the injury in the mammal.

24. A method for stabilizing the extracellular matrix of a selected tissue in a mammal in need thereof, comprising, providing to the selected tissue, an effective amount of an aqueous composition comprising a) one or more catechins, catechin derivatives, or catechin analogs, agonists, or antagonists thereof; b) one or more curcuminoids, curcuminoid derivatives, or curcuminoid analogs, agonists, or antagonists thereof; c) one or more isothiocyanates, isothiocyanate derivatives, or isothiocyanate analogs, agonists, or antagonists thereof; d) one or more stilbenoids, stilbenoid derivatives, or stilbenoid analogs, agonists, or antagonists thereof; e) at least one therapeutic essential oil; f) tetrahydropiperine; and g) at least one compound selected from the group consisting of broccoli seed oil, mustard seed oil, wintercress oil, watercress oil, wintercress seed, watercress seed, and broccoli seed powder, for a time sufficient to stabilize the extracellular matrix of the selected tissue in the mammal.

\* \* \* \* \*